US012741954B2

(12) United States Patent
Lee et al.

(10) Patent No.: US 12,741,954 B2
(45) Date of Patent: Sep. 22, 2026

(54) FUSED HETEROARYL HYDROXAMATES AS STING AGONISTS

(71) Applicant: BiSiChem Co., Ltd., Seongnam-si (KR)

(72) Inventors: Jinwoo Lee, Seongnam-si (KR); Sunhwa Jeon, Seongnam-si (KR); Byungnam Kang, Seongnam-si (KR); Jungwoo Lee, Seongnam-si (KR); Seeun Jeon, Seongnam-si (KR); Youngdo Shin, Seongnam-si (KR); Hongjun Kang, Seongnam-si (KR); Sunjoo Kim, Seongnam-si (KR); Inho Yang, Seongnam-si (KR); Cheolhwan Yoon, Seongnam-si (KR); Cheolkyu Han, Seongnam-si (KR); Jeongbeob Seo, Seongnam-si (KR)

(73) Assignee: BiSiChem Co., Ltd., Seongnam-si (KR)

( * ) Notice: Subject to any disclaimer, the term of this patent is extended or adjusted under 35 U.S.C. 154(b) by 356 days.

(21) Appl. No.: 18/095,596

(22) Filed: Jan. 11, 2023

(65) Prior Publication Data

US 2023/0219931 A1 Jul. 13, 2023

Related U.S. Application Data

(60) Provisional application No. 63/298,273, filed on Jan. 11, 2022.

(51) Int. Cl.

| | |
|---|---|
| ***C07D 401/14*** | (2006.01) |
| ***A61K 39/39*** | (2006.01) |
| ***A61K 45/06*** | (2006.01) |
| ***C07D 403/14*** | (2006.01) |
| ***C07D 471/04*** | (2006.01) |

(52) U.S. Cl.

CPC ............ *C07D 401/14* (2013.01); *A61K 39/39* (2013.01); *A61K 45/06* (2013.01); *C07D 403/14* (2013.01); *C07D 471/04* (2013.01)

(58) Field of Classification Search

None

See application file for complete search history.

(56) References Cited

U.S. PATENT DOCUMENTS

2018/0105514 A1* 4/2018 Mehlmann .............. A61P 31/00

OTHER PUBLICATIONS

Tomas Cihlar, Marshall Fordyce, Current status and prospects of HIV treatment, Current Opinion in Virology, vol. 18, 2016, pp. 50-56 ISSN 1879-6257, https://doi.org/10.1016/j.coviro.2016.03.004.*

Rubenstein EB, et al.; Clinical practice guidelines for the prevention and treatment of cancer the prevention and treatment of cancer therapy-induced oral and gastrointestinal mucositis. Cancer. May 1, 2004;100(9 Suppl):2026-46. doi: 10.1002/cncr.20163. PMID: 15108223.*

* cited by examiner

*Primary Examiner* — Samantha L Shterengarts

(74) *Attorney, Agent, or Firm* — United One Law Group LLC; Kongsik Kim; Jhongwoo Peck

(57) ABSTRACT

The invention provides novel substituted heterocyclic compounds represented by the Formulas I, or a pharmaceutically acceptable salt, solvate, polymorph, ester, tautomer or prodrug thereof, and a composition comprising these compounds. The compounds provided can be used as agonists of Stimulator of Interferon Genes (STING) and are useful in the treatment of cancers and certain infectious diseases.

I

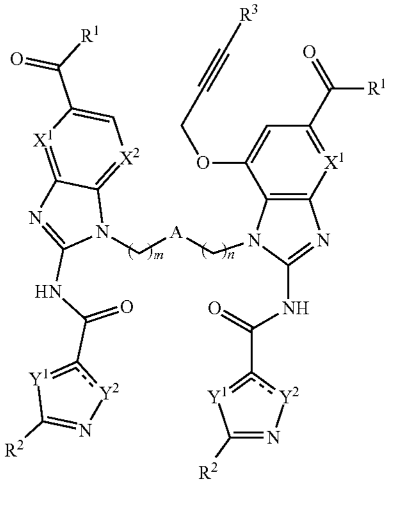

12 Claims, No Drawings

FUSED HETEROARYL HYDROXAMATES AS STING AGONISTS

CROSS-REFERENCE TO RELATED APPLICATION(S)

The present application claims priority from Provisional Application No. 63/298,273 filed on Jan. 11, 2022, which is incorporated herein by reference in its entirety.

FIELD OF THE INVENTION

This invention relates to a series of compounds which are agonist of the stimulator of interferon genes (STING) transforming are useful in the treatment of breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilms tumor, hepatocellular carcinoma, urinary tract cancer, carcinoma of urinary bladder, colorectal cancer, colon cancer, breast cancer, prostate cancer, kidney cancer, hepatocellular carcinoma, thyroid cancer, gallbladder cancer, oophoroma, cervix cancer, stomach cancer, carcinoma of endometrium, head and neck cancer, melanoma, neuroendocrine carcinoma, CNS cancers, brain tumor (for example, glioma, a denaturation oligodendroglioma, adult's glioblastoma multiforme and adult's multiform Property spongioblastoma), osteocarcinoma, soft tissue sarcoma, retinoblastoma, neuroblastoma, seroperitoneum, malignant pleural hydrops, celiothelioma, trophoblastic tumor, hemangiopericytoma, kaposi sarcoma, mucoid carcinoma (myxoid Carcinoma), round cell carcinoma, dermoid cancer, squamous cell carcinoma of esophagus, carcinoma of mouth, adrenocortical carcinoma, an autoimmune condition, atherosclerosis, arthritis (e.g., osteoarthritis or rheumatoid arthritis), an inflammatory bowel disease (e.g., ulcerative colitis or Crohn's disease), a peripheral vascular disease, a cerebral vascular accident (stroke), chronic inflammation, Alzheimer's disease, neurodegenerative disease or disorders, Aicardi-Goutieres syndrome, juvenile arthritis, osteoporosis, amyotrophic lateral sclerosis, multiple sclerosis, cardiac dysfunction, transplantation, or infection.

This invention also relates to a pharmaceutical composition comprising the compound of the invention, use of the compound in the preparation of a medicament, and method of treatment for in mammals, especially humans by administering the compound thereof.

BACKGROUND OF THE INVENTION

The human and other mammals were exposed to germ and threatened by pathogenic and not-pathogenic microbes and have mechanism of immune system. The immune system relies on two major pillars: innate (non-specific), general immune system and adaptive (acquired), specialized immune system. The cell of the innate immune system detect infection through pattern recognition receptors (PRRs) which including the Toll-like receptors (TLRs), the retinoic acid-inducible gene I-like receptors (RLRs), the nucleotide oligomerization domain-like receptors (NLRs, also called NACHT, LRR and PYD domain proteins), AIM2-like receptors (ALRs) and cytosolic DNA sensors (CDS). The PRRs detect the ligand such as pathogen associated molecular patterns (PAMPs) and damage associated molecules patterns (DAMPs) released from damaged cells. The PRR proteins were expressed by dendritic cells, monocytes, epithelial cells, macrophage (Alberts B, et al, Innate immunity. Molecular biology of the cell. 4th ed New York: Gerland Science. (2002); Schroder K, et al, J. Cell. 140(6): 821-32 (2010); Jounai N, et al, Front Cell Infect Microbiol. 2: 168 (2013)). The PRRs was activated by ligand of PAMPs and DAMPs, which triggers signal transduction cascades, result in over expression of genes of pro-inflammatory cytokines and chemokines (Takeuchi O, et al, Cell. 140(6): 805-20 (2010)).

The central signaling of adaptor molecule stimulator of interferon genes (STING), also name as TMEM 173, ERIS, MPYS and MITA is a ubiquitously expressed protein localized on the primarily on the endoplasmic reticulum (ER) membrane. The STING can be recognized and activated by cyclic dinucleotides (CDNs) and aberrant DNA species or in the cytosol of the cell and playing a role in the induction pro-inflammatory cytokines and chemokines, and type I interferons (IFNs) on response (Wu J J, et al, Med Res Rev. (2019); Ishikawa H, et al, Nature. 455(7213): 674-678 (2008)).

The STING was activated by 2',3'-cyclic-GMP-AMP (2', 3'-cGAMP) which was produced from cyclic GMP-AMP (cGAMP) synthase (cGAS), cyclic-di-GMP (CDG) and cyclic-di-AMP(CDA). The CDG and CDA were synthesized by Bacteria such as *Listeria monocytogenes*. Upon binding to CDNs, STING in turn recruit the downstream Tank-binding kinase 1 (TBK1) that subsequently phosphates STING and the transcription factor interferon regulatory factor 3 (IRF3), leading to induction of type I IFNs and proinflammatory cytokines such as tumor necrosis factor $\alpha$ (TNF-$\alpha$) and interleukin 6 (IL-6), resulting in the pathogen eradication and the long-lasting protective innate and adaptive immune system response. Type I interferons plays a crucial role in promoting cross-priming of CD8+T cells and enhance dendritic cell (Woodward J J, et al, Science. 328 (5986):1703-1705 (2010); Chen J, et al, J Clin Invest. 129(10): 4224-4238 (2019)).

A small chemical synthesis and structure modification substitutes the STING agonist of CDNs which has hydrophilicity, unstable and negative charges. In addition, phosphate moiety on CDNs was decreased by phosphoesterase and have drawback to combine with STING. The compound of STING agonist activated in innate immune system and anti-tumor immune response through the upregulation of IFNs. Additionally, STING activation within a tumor microenvironment (TME) drives T lymphocyte priming (Yun L V, et al, Front Microbiol. 10 (2019)).

This type of the Immunomodulation has a useful auto inflammatory disease, cancer, allergic diseases, neurodegenerative diseases, inflammatory diseases, amyotrophic lateral sclerosis, multiple sclerosis, irritable bowel disease (Zitvogel L, et al, Nat Rev Immunol. 15(7): 405-14 (2015); Moisan J, et al, Am J Physiol. Lung Cell Mol. Physiol. 290(5): L987-95 (2006); Cirulli E T, et al, Science. 347(6229): 1436-41 (2015)).

In contrast, type I IFN production increasing is relative with chronic infections such as Mycobacteria, Franciscella, *Chlamydia, Plasmodium* (Sebastian A, et al, J Immunol. 194(6): 2455-2465 (2015); Sebina I, et al, Immunology. 155(2): 176-185 (2018)). In addition, the patients with complex form of autoimmune disease, including systemic lupus erythematous (SLE), Aicadi-Goutieres syndrome (AGS) and STING-associated vasculopathy with onset in infancy (SAVI). Furthermore, the hyper-activation of the STING pathway induced cytokine storm and systemic inflammation. Accordingly, STING inhibitors are cure autoimmune disease and treatment to patient with chronic activation of the STING and pro-inflammatory cytokine production (Barber G N. et al, Nat Rev Immunol. 15(12): 760-70 (2015); Gall A, et al, Immunity. 36(1): 120-31 (2012); Crow Y J, et al, Nat Rev Immunol. 15(7): 429-40 (2015); Rice G I, et al, J Clin Immunol. 35(3): 235-43 (2015)).

The STING agonist compounds treatment of cancer, superficial skin cancers, premalignant actinic keratosis, precancerous syndromes, infectious diseases, asthma, and allergic rhinitis (Mathur V, et al, Neuron. 96(6): 1290-1302 (2017); Huber J P, et al, J Immunol. 185(2): 813-7 (2010)). Accordingly, STING activity from agonist provides a promising therapeutic effect in several diseases.

SUMMARY OF THE INVENTION

This invention provides compounds of the Formulas I, or a pharmaceutically acceptable salt, solvate, polymorph, ester, tautomer or prodrug thereof:

I

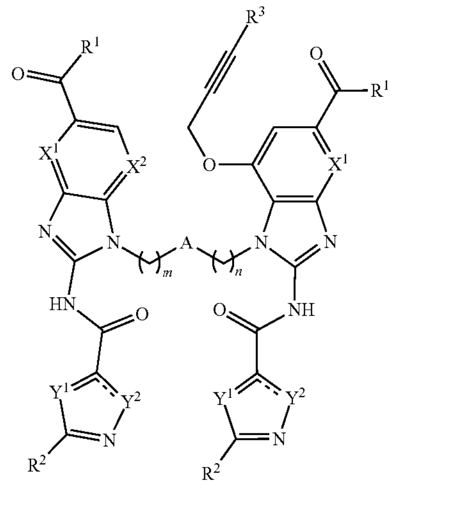

wherein, each $R^1$ is independently $NH_2$, OH, $NHOR^4$ or $NHR^4$;

each $R^2$ is independently hydrogen, halogen, $CF_3$, —($C_1$-$C_6$)alkyl, —O($C_1$-$C_6$)alkyl, acyl, amino, substituted amino, cyano, acyloxy or aryloxy;

$R^3$ is hydrogen, halogen, $CF_3$, acyl, amino, substituted amino, —($C_1$-$C_6$)alkyl, —($C_1$-$C_6$)haloalkyl, —($C_3$-$C_6$)cycloalkyl, —($C_1$-$C_6$)alkoxy, —($C_1$-$C_6$)hydroxyalkyl, hetCyc[1], hetCyc[2], —($C_1$ -$C_3$)alkyl[hetCyc[1]], —($C_1$-$C_3$)alkyl[hetCyc[2]], —($C_1$-$C_3$)alkyl[hetAr[2]], —($C_1$-$C_3$)alkyl[hetAr[3]], cyano, nitro, alkoxy, acyloxy or aryloxy;

$R^4$ is H, trifluoromethyl, —($C_1$-$C_6$)alkyl, —($C_2$-$C_6$)alkenyl, —($C_2$-$C_6$)alkynyl, —($C_1$-$C_3$)alkyl[($C_3$-$C_6$)cycloalkyl], —($C_1$-$C_6$)fluoroalkyl, —($C_1$-$C_6$)difluoroalkyl, —($C_1$-$C_6$)trifluoroalkyl, —($C_1$-$C_6$)alkylamine, —($C_1$-$C_6$)hydroxyalkyl, —($C_2$-$C_6$)dihydroxyalkyl, [($C_1$-$C_6$)alkoxy]($C_1$-$C_6$)alkyl- or [($C_1$-$C_6$)alkoxy]-[($C_1$-$C_6$)alkoxy]-($C_1$-$C_6$)alkyl-;

each $X^1$ and $X^2$ are independently N or $CR^5$;

$R^5$ is hydrogen, halogen, OH, $CF_3$, acyl, amino, substituted amino, —($C_1$-$C_6$)alkyl, substituted ($C_1$-$C_6$)alkyl, —($C_1$-$C_6$)haloalkyl, cyano, nitro, alkoxy, acyloxy, aryloxy, —O($C_1$-$C_6$)alkyl, —O($C_1$-$C_6$)hydroxyalkyl, —O($C_2$-$C_6$)alkenyl[($C_4$-$C_6$)hydoxy], —O($C_2$-$C_6$)alkynyl[($C_4$-$C_6$)hydoxy], —O($C_2$-$C_6$)alkynyl[hetCyc[1]], —O($C_1$-$C_6$)alkyl[($C_1$-$C_6$)alkoxy], —O($C_2$-$C_6$)alkenyl[($C_1$-$C_6$)alkoxy], —O($C_2$-$C_6$)alkynyl[($C_1$-$C_6$)alkoxy], —O($C_1$-$C_6$)alkyl[($C_3$-$C_6$)cycloalkyl], —O($C_1$-$C_3$)alkyl[hetCyc[1]], —O($C_1$-$C_3$)alkyl[hetCyc[2]] or —O($C_2$-$C_6$)alkynyl[hetCyc[1]];

hetCyc[1] is a 4-6 membered heterocyclic ring containing 1-2 heteroatoms selected from nitrogen, oxygen or sulfur, wherein said heterocyclic ring is optionally substituted with a substituent selected from —($C_1$-$C_6$)alkyl, —($C_1$-$C_6$)alkoxy, OH, halogen, —C(O)$R^6$, —$CO_2R^6$, —C(O)$NR^6R^7$, —$S(O)_2NR^6R^7$, or —$S(O)_2R^6$;

hetCyc[2] is a bridged 8-membered heterocyclic ring having a ring nitrogen atom and optionally having a ring oxygen atom;

$R^6$ is H, —($C_1$-$C_6$)alkyl, —($C_1$-$C_6$)fluoroalkyl, —($C_1$-$C_6$)difluoroalkyl, —($C_1$-$C_6$)trifluoroalkyl, —($C_1$-$C_6$ alkyl)-$NR^7R^8$, —($C_1$-$C_6$)hydroxyalkyl, —($C_2$-$C_6$)dihydroxyalkyl, [($C_1$-$C_6$)alkoxy]($C_1$-$C_6$)alkyl-, [($C_1$-$C_6$)alkoxy]-[($C_1$-$C_6$)alkoxy]-($C_1$-$C_6$)alkyl-, hetCyc[1], $Ar^1$, $hetAr^2$ or $hetAr^3$;

$R^7$ is H or —($C_1$-$C_6$)alkyl;

or $NR^6R^7$ forms a 4-6 membered ring with one or more heteroatoms selected from N and O, wherein said ring is optionally substituted with one or more substituents independently selected from —($C_1$-$C_6$)alkyl, OH, $NH_2$, —($C_1$-$C_6$)hydroxyalkyl, —($C_1$-$C_6$)alkylamine, —$CO_2R^8$, and —(C $_1$-$C_3$)alkyl$CO_2R^8$;

$R^8$ is H, —($C_1$-$C_3$)alkyl or —($C_1$-$C_3$)hydroxyalkyl;

$Ar^1$ is phenyl optionally substituted with one or more substituents independently selected from ($C_1$-$C_6$)alkoxy, halogen, ($C_1$-$C_6$)alkyl and $CF_3$;

$hetAr^2$ is pyridyl optionally substituted with one or more substituents independently selected from halogen, $CF_3$, ($C_1$-$C_6$)alkyl and ($C_1$-$C_6$)alkoxy;

$hetAr^3$ is a 5-membered heteroaryl having 2-3 ring heteroatoms independently selected from N, O and S and optionally substituted with ($C_1$-$C_6$)alkyl and OH;

$Y^1$ and $Y^2$ are each independently N, O, S, $CR^9$, $NR^{10}$;

$R^9$ is hydrogen, halogen, $CF_3$, —($C_1$-$C_6$)alkyl or —O($C_1$-$C_6$)alkyl;

$R^{10}$ is hydrogen, —($C_1$-$C_6$)alkyl or acyl;

A is —CH═CH—, —C≡C—, —$CH_2$—, —$CR^{11}R^{12}$—, —C(O)$NR^{13}$—, —C(O)$NHOR^{14}$—, —$NR^{13}$C(O)—, —$NR^{13}CO_2$—, —$NR^{13}$C(O)$NR^{13}$—, —$NR^{13}$—, —($C_3$-$C_7$)cycloalkyl-, —O—, —S—, —S(O)— or —$S(O)_2$—, optionally substituted -phenyl-, optionally substituted -(5-6 membered heteroaryl)- or optionally substituted -(5-6 membered heterocycloalkyl)-;

$R^{11}$ is selected from the group consisting of F, $CF_3$, —($C_1$-$C_6$)alkyl, substituted ($C_1$-$C_6$)alkyl, cyano;

$R^{12}$ is H, F, $CF_3$, —($C_1$-$C_6$)alkyl;

or $R^{11}$ and $R^{12}$ together with the atom to which they are attached form a 3 to 7 membered carbocyclic or heterocyclic ring;

$R^{13}$ is hydrogen, —($C_1$-$C_6$)Calkyl, —($C_1$-$C_6$)Cfluoroalkyl, —($C_1$-$C_6$)difluoroalkyl or —($C_1$-$C_6$)trifluoroalkyl;

$R^{14}$ is —($C_1$-$C_6$)alkyl, —($C_1$-$C_6$)fluoroalkyl, —($C_1$-$C_6$)difluoroalkyl, —($C_1$-$C_6$)trifluoroalkyl or [($C_1$-$C_6$)alkoxy]($C_1$-$C_6$)alkyl-;

m is 0, 1, 2 or 3;

n is 0, 1, 2 or 3;

Compounds of Formula I further include compounds of the Formula II-a, II-b, and II-c II-a

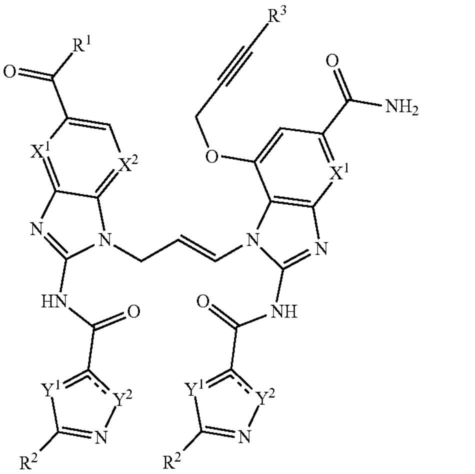

II-b

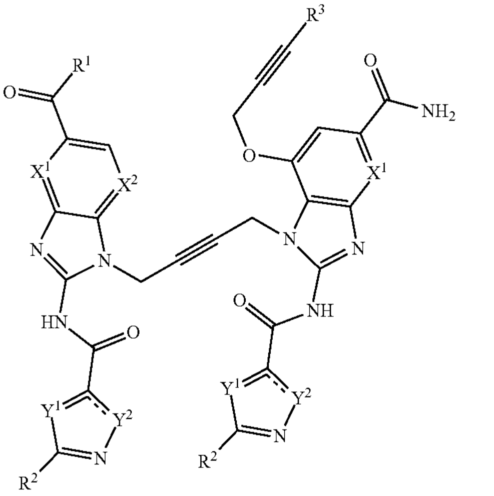

II-c

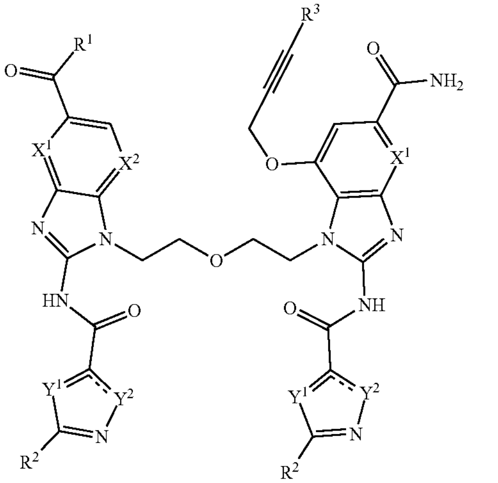

or pharmaceutically acceptable salt thereof, wherein;

each $R^2$ is independently hydrogen, halogen, $CF_3$, —($C_1$-$C_6$)alkyl, —O($C_1$-$C_6$)alkyl, acyl, amino, substituted amino, cyano, acyloxy or aryloxy;

$R^3$ is hydrogen, halogen, $CF_3$, acyl, amino, substituted amino, —($C_1$-$C_6$)alkyl, —($C_1$-$C_6$)haloalkyl, —($C_3$-$C_6$)cycloalkyl, —($C_1$-$C_6$)alkoxy, —($C_1$-$C_6$)hydroxyalkyl, $hetCyc^1$, $hetCyc^2$, —($C_1$-$C_3$)alkyl[$hetCyc^1$], —($C_1$-$C_3$)alkyl[$hetCyc^2$], —($C_1$-$C_3$)alkyl[$hetAr^2$], —($C_1$-$C_3$)alkyl[$hetAr^3$], cyano, nitro, alkoxy, acyloxy or aryloxy;

$hetCyc^1$ is a 4-6 membered heterocyclic ring containing 1-2 heteroatoms selected from nitrogen, oxygen or sulfur, wherein said heterocyclic ring is optionally substituted with a substituent selected from —($C_1$-$C_6$)alkyl, —($C_1$-$C_6$)alkoxy, OH, halogen, —C(O)$R^6$, —$CO_2R^6$, —C(O)$NR^6R^7$, —$S(O)_2NR^6R^7$, or —$S(O)_2R^6$;

$hetCyc^2$ is a bridged 8-membered heterocyclic ring having a ring nitrogen atom and optionally having a ring oxygen atom;

each $X^1$ and $X^2$ are independently N or $CR^5$;

$R^5$ is hydrogen, halogen, OH, $CF_3$, acyl, amino, substituted amino, —($C_1$-$C_6$)alkyl, substituted ($C_1$-$C_6$)alkyl, —($C_1$-$C_6$)haloalkyl, cyano, nitro, alkoxy, acyloxy, aryloxy, —O($C_1$-$C_6$)alkyl, —O($C_1$-$C_6$)hydroxyalkyl, —O($C_2$-$C_6$)alkenyl[($C_4$-$C_6$)hydoxy], —O($C_2$-$C_6$)alkynyl[($C_4$-$C_6$)hydoxy], —O($C_2$-$C_6$)alkynyl[$hetCyc^1$], —O($C_1$-$C_6$)alkyl[($C_1$-$C_6$)alkoxy], —O($C_2$-$C_6$)alkenyl[($C_1$-$C_6$)alkoxy], —O($C_2$-$C_6$)alkynyl[($C_1$-$C_6$)alkoxy], —O($C_1$-$C_6$)alkyl[($C_3$-$C_6$)cycloalkyl], —O($C_1$-$C_3$)alkyl[$hetCyc^1$], —O($C_1$-$C_3$)alkyl[$hetCyc^2$] or —O($C_2$-$C_6$)alkynyl[$hetCyc^1$];

$R^6$ is H, —($C_1$-$C_6$)alkyl, —($C_1$-$C_6$)fluoroalkyl, —($C_1$-$C_6$)difluoroalkyl, —($C_1$-$C_6$)trifluoroalkyl, —($C_1$-$C_6$ alkyl)-$NR^7R^8$, —($C_1$-$C_6$)hydroxyalkyl, —($C_2$-$C_6$)dihydroxyalkyl, [($C_1$-$C_6$)alkoxy]($C_1$-$C_6$)alkyl-, [($C_1$-$C_6$)alkoxy]-[($C_1$-$C_6$)alkoxy]-($C_1$-$C_6$)alkyl-, $hetCyc^1$, $Ar^1$, $hetAr^2$ or $hetAr^3$;

$R^7$ is H or —($C_1$-$C_6$)alkyl;

or $NR^6R^7$ forms a 4-6 membered ring with one or more heteroatoms selected from N and O, wherein said ring is optionally substituted with one or more substituents independently selected from —($C_1$-$C_6$)alkyl, OH, $NH_2$, —($C_1$-$C_6$)hydroxyalkyl, —($C_1$-$C_6$)alkylamine, —$CO_2R^8$, and —($C_1$-$C_3$)alkyl$CO_2R^8$;

$R^8$ is H, —($C_1$-$C_3$)alkyl or —($C_1$-$C_3$)hydroxyalkyl;

$Ar^1$ is phenyl optionally substituted with one or more substituents independently selected from ($C_1$-$C_6$)alkoxy, halogen, ($C_1$-$C_6$)alkyl and $CF_3$;

$hetAr^2$ is pyridyl optionally substituted with one or more substituents independently selected from halogen, $CF_3$, ($C_1$-$C_6$)alkyl and ($C_1$-$C_6$)alkoxy;

$hetAr^3$ is a 5-membered heteroaryl having 2-3 ring heteroatoms independently selected from N, O and S and optionally substituted with ($C_1$-$C_6$)alkyl and OH;

$Y^1$ and $Y^2$ are each independently N, O, S, $CR^9$, $NR^{10}$;

$R^9$ is hydrogen, halogen, $CF_3$, —($C_1$-$C_6$)alkyl or —O($C_1$-$C_6$)alkyl;

$R^{10}$ is hydrogen, —($C_1$-$C_6$)alkyl or acyl;

Compounds of Formula I further include compounds of the Formula III-a, III-b, III-c, and III-d III-a

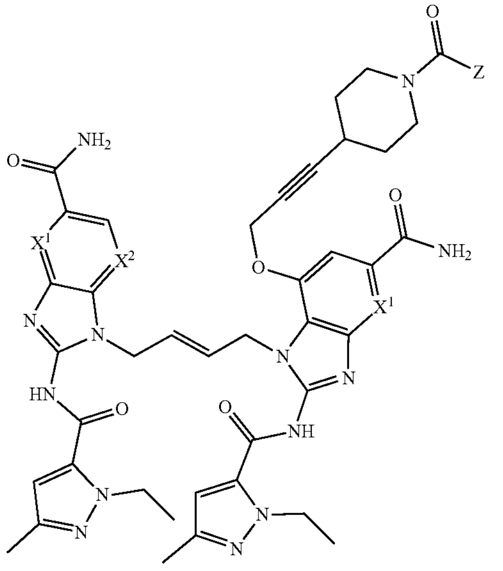

III-b

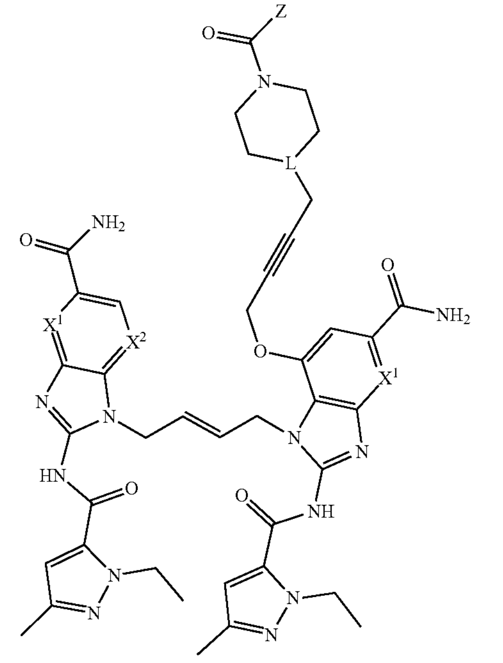

-continued

III-c

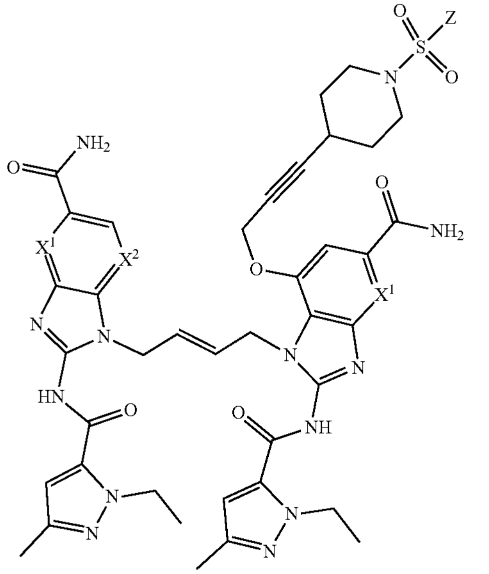

III-d

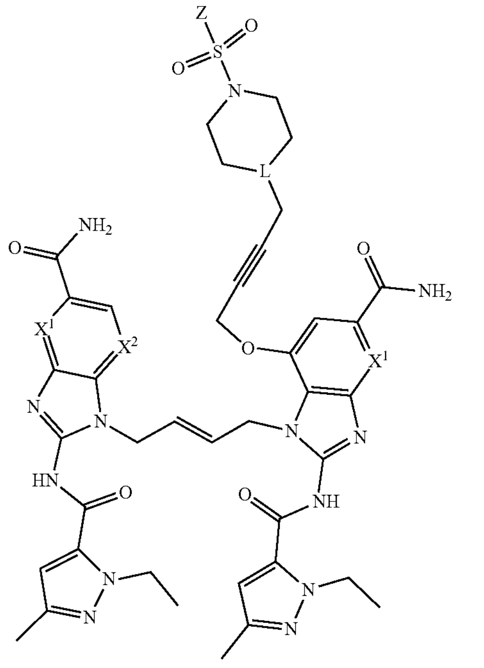

or pharmaceutically acceptable salt thereof, wherein;

Z is —$R^6$, —$OR^6$, —$NR^6R^7$, —$(C_1\text{-}C_6)$alkyl, —$(C_1\text{-}C_6)$fluoroalkyl, —$(C_1\text{-}C_6)$difluoroalkyl, —$(C_1\text{-}C_6)$trifluoroalkyl, —$(C_1\text{-}C_6$ alkyl)-$NR^7R^8$, —$(C_1\text{-}C_6)$hydroxyalkyl, —$(C_2\text{-}C_6)$dihydroxyalkyl, $[(C_1\text{-}C_6)$alkoxy$](C_1\text{-}C_6)$alkyl- or $[(C_1\text{-}C_6)$alkoxy$]\text{-}[(C_1\text{-}C_6)$alkoxy$]\text{-}(C_1\text{-}C_6)$ alkyl-;

L is CH or N;

each $X^1$ and $X^2$ are independently N or $CR^5$;

$R^5$ is hydrogen, halogen, OH, $CF_3$, acyl, amino, substituted amino, —$(C_1\text{-}C_6)$alkyl, substituted $(C_1\text{-}C_6)$alkyl, —$(C_1\text{-}C_6)$haloalkyl, cyano, nitro, alkoxy, acyloxy, aryloxy, —$O(C_1\text{-}C_6)$alkyl, —$O(C_1\text{-}C_6)$hydroxyalkyl, —$O(C_2\text{-}C_6)$alkenyl$[(C_4\text{-}C_6)$hydoxy$]$, —$O(C_2\text{-}C_6)$alkynyl$[(C_4\text{-}C_6)$hydoxy$]$, —$O(C_2\text{-}C_6)$alkynyl[hetCyc$^1$], —$O(C_1\text{-}C_6)$alkyl$[(C_1\text{-}C_6)$alkoxy$]$, —$O(C_2\text{-}C_6)$alkenyl $[(C_1\text{-}C_6)$alkoxy], —$O(C_2\text{-}C_6)$alkynyl$[(C_1\text{-}C_6)$alkoxy], —$O(C_1\text{-}C_6)$alkyl$[(C_3\text{-}C_6)$cycloalkyl], —$O(C_1\text{-}C_3)$alkyl[hetCyc$^1$], —$O(C_1\text{-}C_3)$alkyl[hetCyc$^2$] or —$O(C_2\text{-}C_6)$alkynyl[hetCyc$^1$];

$R^6$ is H, —$(C_1\text{-}C_6)$alkyl, —$(C_1\text{-}C_6)$fluoroalkyl, —$(C_1\text{-}C_6)$ difluoroalkyl, —$(C_1\text{-}C_6)$trifluoroalkyl, —$(C_1\text{-}C_6$ alkyl)-$NR^7R^8$, —$(C_1\text{-}C_6)$hydroxyalkyl, —$(C_2\text{-}C_6)$dihydroxyalkyl, $[(C_1\text{-}C_6)$alkoxy]$(C_1\text{-}C_6)$alkyl-, $[(C_1\text{-}C_6)$ alkoxy]-$[(C_1\text{-}C_6)$alkoxy]—$(C_1\text{-}C_6)$alkyl-, hetCyc$^1$, $Ar^1$, hetAr$^2$ or hetAr$^3$;

$R^7$ is H or —$(C_1\text{-}C_6)$alkyl;

or $NR^6R^7$ forms a 4-6 membered ring with one or more heteroatoms selected from N and O, wherein said ring is optionally substituted with one or more substituents independently selected from —$(C_1\text{-}C_6)$alkyl, OH, $NH_2$, —$(C_1\text{-}C_6)$hydroxyalkyl, —$(C_1\text{-}C_6)$alkylamine, —$CO_2R^8$, and —$(C_1\text{-}C_3)$alkyl$CO_2R^8$;

$R^8$ is H, —$(C_1\text{-}C_3)$alkyl or —$(C_1\text{-}C_3)$hydroxyalkyl;

hetCyc$^1$ is a 4-6 membered heterocyclic ring containing 1-2 heteroatoms selected from nitrogen, oxygen or sulfur, wherein said heterocyclic ring is optionally substituted with a substituent selected from —$(C_1\text{-}C_6)$ alkyl, —$(C_1\text{-}C_6)$alkoxy, OH, halogen, —$C(O)R^6$, —$CO_2R^6$, —$C(O)NR^6R^7$, —$S(O)_2NR^6R^7$, or —$S(O)_2R^6$;

hetCyc$^2$ is a bridged 8-membered heterocyclic ring having a ring nitrogen atom and optionally having a ring oxygen atom;

$Ar^1$ is phenyl optionally substituted with one or more substituents independently selected from $(C_1\text{-}C_6)$ alkoxy, halogen, $(C_1\text{-}C_6)$alkyl and $CF_3$;

hetAr$^2$ is pyridyl optionally substituted with one or more substituents independently selected from halogen, $CF_3$, $(C_1\text{-}C_6)$alkyl and $(C_1\text{-}C_6)$alkoxy;

hetAr$^3$ is a 5-membered heteroaryl having 2-3 ring heteroatoms independently selected from N, O and S and optionally substituted with $(C_1\text{-}C_6)$alkyl and OH;

Compounds of present invention are agonist of the stimulator of interferon genes (STING) transforming and, consequently, are useful for treating breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilms tumor, hepatocellular carcinoma, urinary tract cancer, carcinoma of urinary bladder, colorectal cancer, colon cancer, breast cancer, prostate cancer, kidney cancer, hepatocellular carcinoma, thyroid cancer, gallbladder cancer, oophoroma, cervix cancer, stomach cancer, carcinoma of endometrium, head and neck cancer, melanoma, neuroendocrine carcinoma, CNS cancers, brain tumor (for example, glioma, a denaturation oligodendroglioma, adult's glioblastoma multiforme and adult's multiform Property spongioblastoma), osteocarcinoma, soft tissue sarcoma, retinoblastoma, neuroblastoma, seroperitoneum, malignant pleural hydrops, celiothelioma, trophoblastic tumor, hemangiopericytoma, kaposi sarcoma, mucoid carcinoma (myxoid Carcinoma), round cell carcinoma, dermoid cancer, squamous cell carcinoma of esophagus, carcinoma of mouth, adrenocortical carcinoma, an autoimmune condition, atherosclerosis, arthritis (e.g., osteoarthritis or rheumatoid arthritis), an inflammatory bowel disease (e.g., ulcerative colitis or Crohn's disease), a peripheral vascular disease, a cerebral vascular accident (stroke), chronic inflammation, Alzheimer's disease, neurodegenerative disease or disorders, Aicardi-Goutieres syndrome, juvenile arthritis, osteoporosis, amyotrophic lateral sclerosis, multiple sclerosis, cardiac dysfunction, transplantation, or infection.

In other aspects, the present invention is directed to a pharmaceutical composition comprising an effective amount of compounds of formula I or a pharmaceutically acceptable salt, solvate, polymorph, ester, tautomer or prodrug thereof. In some embodiments, the pharmaceutical composition further comprises a pharmaceutically acceptable carrier, adjuvants and/or excipients. In some embodiments, such a composition may contain at least one of preservatives, agents for delaying absorption, fillers, binders, adsorbents, buffers, disintegrating agents, solubilizing agents, and other carriers, adjuvants and/or excipients as inert ingredients. The composition may be formulated with a method well-known in the art.

In some aspects, the present invention is directed to a method of treating a disease in an individual suffering from said disease comprising administering to said individual a therapeutically effective amount of a composition comprising compounds of formula I or a pharmaceutically acceptable salt, solvate, polymorph, ester, tautomer or prodrug thereof.

In other aspects, the present invention is directed to a method of treating a disorder in a mammal, comprising administering to said mammal a therapeutically effective amount of compounds of formula I or a pharmaceutically acceptable salt, solvate, polymorph, ester, tautomer or prodrug thereof.

In other aspects, the present invention is directed to a method of treating a disorder in a human, comprising administering to said human a therapeutically effective amount of compounds of formula I or a pharmaceutically acceptable salt, solvate, polymorph, ester, tautomer or prodrug thereof.

In other aspects, the present invention is directed to a method of treating breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilms tumor, hepatocellular carcinoma, urinary tract cancer, carcinoma of urinary bladder, colorectal cancer, colon cancer, breast cancer, prostate cancer, kidney cancer, hepatocellular carcinoma, thyroid cancer, gallbladder cancer, oophoroma, cervix cancer, stomach cancer, carcinoma of endometrium, head and neck cancer, melanoma, neuroendocrine carcinoma, CNS cancers, brain tumor (for example, glioma, a denaturation oligodendroglioma, adult's glioblastoma multiforme and adult's multiform Property spongioblastoma), osteocarcinoma, soft tissue sarcoma, retinoblastoma, neuroblastoma, seroperitoneum, malignant pleural hydrops, celiothelioma, trophoblastic tumor, hemangiopericytoma, kaposi sarcoma, mucoid carcinoma (myxoid Carcinoma), round cell carcinoma, dermoid cancer, squamous cell carcinoma of esophagus, carcinoma of mouth, adrenocortical carcinoma, an autoimmune condition, atherosclerosis, arthritis (e.g., osteoarthritis or rheumatoid arthritis), an inflammatory bowel disease (e.g., ulcerative colitis or Crohn's disease), a peripheral vascular disease, a cerebral vascular accident (stroke), chronic inflammation, Alzheimer's disease, neurodegenerative disease or disorders, Aicardi-Goutieres syndrome, juvenile arthritis, osteoporosis, amyotrophic lateral sclerosis, multiple sclerosis, cardiac dysfunction, transplantation, infection diseases, condition, or disorder in a mammal, including a human, comprising administering to said mammal a therapeutically effective amount of compounds of formula I, or a pharmaceutically acceptable salt, ester, prodrug, solvate, such as hydrate, polymorph or tautomer thereof.

In other aspects, the present invention is directed to a method of treating a disorder or condition which is modulated by the stimulator of interferon genes (STING) transforming in a mammal, including a human, comprising administering to said mammal an amount of compounds of the formula I, or a pharmaceutically acceptable salt, ester, prodrug, solvate, such as hydrate, polymorph or tautomer thereof, effective to modulate said cascade. The appropriate dosage for a particular patient can be determined, according to known methods, by those skilled in the art.

In other aspects, the present invention is directed to use of compounds of the formula I or a pharmaceutically acceptable salt, ester, prodrug, solvate, such as hydrate, polymorph or tautomer thereof in the preparation of a pharmaceutical composition. The pharmaceutical composition can be used for treating a disorder or condition which is modulated by the stimulator of interferon genes (STING) transforming in a mammal, including a human. The pharmaceutical composition is useful for treating cancers and other inflammation.

In other aspects, the present invention is directed to a pharmaceutical composition comprising compounds of formula I or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution and suspension. In some embodiments, the pharmaceutical composition is in a form suitable for parenteral injection, such as a sterile solution, suspension or emulsion; for topical administration as an ointment or cream or for rectal administration as a suppository. In further or additional embodiments, the pharmaceutical composition is in unit dosage forms suitable for single administration of precise dosages. In further or additional embodiments, the amount of compounds of formula I is in the range of about 0.001 to about 1000 mg/kg body weight/day. In further or additional embodiments, the amount of compounds of formula I is in the range of about 0.5 to about 50 mg/kg body weight/day.

In other aspects, the present invention is directed to a process for preparing compounds of formula I or a pharmaceutically acceptable salt, solvate, polymorph, ester, tautomer or prodrug thereof.

DETAILED DESCRIPTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., $CH_2CH_3$), fully substituted (e.g., $CF_2CF_3$), mono-substituted (e.g., $CH_2CH_2F$) or substituted at a level anywhere in-between fully substituted and mono-substituted (e.g., $CH_2CHF_2$, $CF_2CH_3$, $CFHCHF_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 Daltons, and more typically, up to about 500 Daltons (except in those instances where macromolecular substituents are clearly intended, e.g., polypeptides, polysaccharides, polyethylene glycols, DNA, RNA and the like).

As used herein, $C_1$-Cn, includes $C_1$-$C_2$, $C_1$-$C_3$, . . . $C_1$-Cn. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, isobutyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The terms "heteroatom" or "hetero" as used herein, alone or in combination, refer to an atom other than carbon and hydrogen. Heteroatoms are independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl).

A non-limiting example of "cycloalkyl" includes aziridinyl, azetidinyl, oxetanyl, thietanyl, homopiperidinyl, oxepanyl, thiepanyl, oxazepinyl, diazepinyl, thiazepinyl, 1,2,3,6- tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl and quinolizinyl and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized at-electron system containing 4n+2 n electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

Certain Pharmaceutical Terminology

The term "subject", "patient" or "individual" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, a therapeutically effective amount of compounds of the Formula I, or a pharmaceutically acceptable salt thereof, is a quantity of an inventive agent that, when administered to a human in need thereof, is sufficient to modulate the activity of STING such that a disease condition which is mediated by that activity is reduced, alleviated or prevented. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., *J. Pharm. Sci.* 1977, 66, 1-19). Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "solvate" as used herein refers to a combination of a compound of this invention with a solvent molecule formed by solvation. In some situations, the solvate refers to a hydrate, i.e., the solvent molecule is a water molecule, the combination of a compound of this invention and water forms a hydrate.

The term "polymorph" or "polymorphism" as used herein refers to a compound of this invention present in different crystal lattice forms.

The term "ester" as used herein refers to a derivative of a compound of this invention derived from an oxoacid group and a hydroxyl group, either one of which can be present at the compound of this invention.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elsevier, 1985 and Method in Enzymology, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review,* 1992, 8, 1-38, each of which is incorporated herein by reference. The prodrugs described herein include, but are not limited to, the following groups and combinations of these groups; amine derived prodrugs: Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Further information on metabolism may be obtained from *The Pharmacological Basis of Therapeutics*, 9th Edition, McGraw-Hill (1996).

EXPERIMENTAL PART

NMR spectra were recorded in DMSO-$d_6$, MeOH-$d_4$, $CDCl_3$ solution in 5-mm o.d. tubes (Norell, Inc. 507-HP) at 30° C. and collected on JEOL at 400 MHz for $^1$H. The chemical shifts (δ) are relative to tetramethylsilane (TMS=0.00 ppm) and expressed in ppm. LC/MS was taken on Ion-trap Mass Spectrometer on ISQ EM, Thermo Fisher Vanquish Flex (Column: hypersil Gold (C18, Ø2.1×50 mm, 1.9 μm, 120 Å, 30° C.) operating in ESI(+) ionization mode; flow rate=0.5 mL/min. Mobile phase=0.01% heptafluorobutyric acid (HFBA) and 1.0% isopropyl alcohol (IPA) in water or $CH_3CN$.

Intermediate 1: methyl (E)-4-((4-aminobut-2-en-1-yl)amino)-3-methoxy-5-nitrobenzoate hydrochloride

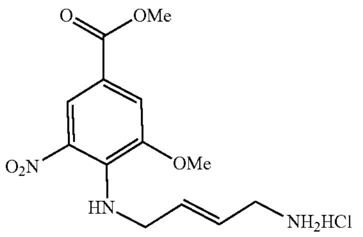

Step A: methyl (E)-4-((4-((tert-butoxycarbonyl)amino)but-2-en-1-yl)amino)-3-methoxy-5-nitrobenzoate To a solution of methyl 4-chloro-3-methoxy-5-nitrobenzoate (5.00 g, 20.4 mmol) in n-BuOH (50 mL) was added tert-butyl N-[(2E)-4-aminobut-2-en-1-yl]carbamate hydrochloride (4.53 g, 20.4 mmol) and DIPEA (17.7 mL, 102 mmol) at room temperature. The reaction mixture was heated at 120° C. for 12 hours. After concentration in vacuo, the residue was dissolved in EtOAc and washed with saturated aq. $NaHCO_3$ solution. The separated aqueous layer was extracted with EtOAc twice. The combined organic layers were washed with brine, dried over $Na_2SO_4$, filtered, and concentrated in vacuo. The residue was purified by recrystallization from MeOH to give the title compound (5.56 g, 66%) as a yellow solid. $^1$H NMR (400 MHz, DMSO-$d_6$): δ 8.17 (1H, d, J=1.9 Hz), 8.02 (1H, t, J=6.2 Hz), 7.43 (1H, d, J=1.9 Hz), 6.94 (1H, t, J=5.9 Hz), 5.52 (2H, t, J=3.0 Hz), 4.12 (2H, dd, J=6.1, 3.0 Hz), 3.89 (3H, s), 3.83 (3H, s), 3.50-3.43 (2H, m), 1.35 (9H, s). LC-MS: m/z=396.10 $[M+H]^+$.

Step B: methyl (E)-4-((4-aminobut-2-en-1-yl)amino)-3-methoxy-5-nitrobenzoate hydro-chloride To a solution of methyl (E)-4-((4-((tert-butoxycarbonyl)amino)but-2-en-1-yl)amino)-3-methoxy-5-nitrobenzoate (1.00 g, 2.53 mmol) in MeOH (6.8 mL) was added HCl (4 M in dioxane, 6.3 mL, 25 mmol) at room temperature. The reaction mixture was stirred at room temperature overnight. After concentration in vacuo, the residual solid was suspended in $Et_2O$, collected by filtration, washed with $Et_2O$, and then dried under vacuum to give the title compound (827 mg, 99%) as an orange solid. $^1$H NMR (400 MHz, DMSO-$d_6$): δ 8.19 (1H, d, J=1.6 Hz), 8.14 (1H, t, J=7.2 Hz), 7.81 (3H, brs), 7.46 (1H, d, J=2.0 Hz), 5.87-5.82 (1H, m), 5.63-5.58 (1H, m), 4.21 (2H, t, J=6.0 Hz), 3.90 (3H, s), 3.84 (3H, s), 3.40 (2H, brs).

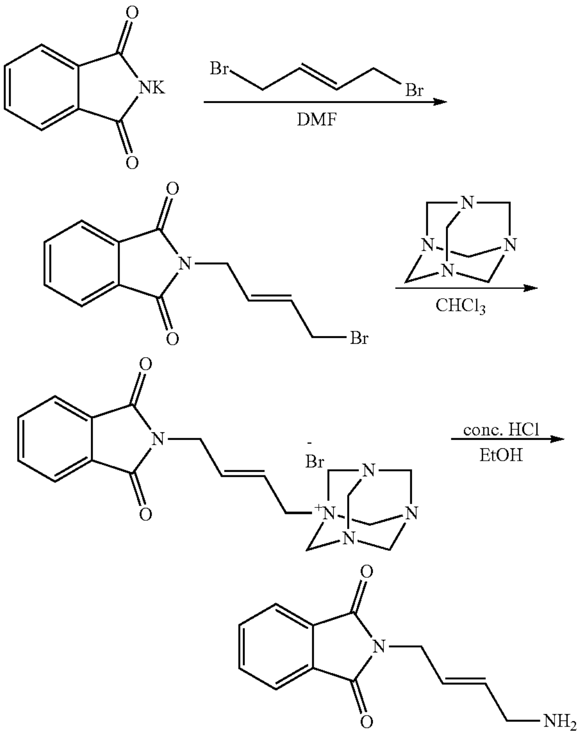

Intermediate 2: (E)-2-(4-aminobut-2-en-1-yl)isoindoline-1,3-dione

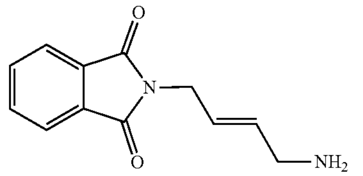 [SMILES: NC/C=C/CN1C(=O)c2ccccc2C1=O]

Step A: (E)-2-(4-bromobut-2-en-1-yl)isoindoline-1,3-dione

To a solution of potassium phthalimide (10.0 g, 54.0 mmol) in DMF (56 mL) was added (E)-1,4-dibromobut-2-ene (34.6 g, 162 mmol) at room temperature. The reaction mixture was stirred at room temperature for 22 hours. After addition of cold water, a precipitated solid was collected by filtration. The solid was purified by column chromatography on $SiO_2$ (Hexanes:EtOAc=4:1 to 1:1) to give the title compound (9.86 g, 65%) as a white solid. $^1H$ NMR (400 MHz, $CDCl_3$): δ 7.88-7.83 (2H, m), 7.75-7.70 (2H, m), 5.98-5.80 (1H, m), 5.86-5.79 (1H, m), 4.30 (2H, dd, J=0.8, 6.0 Hz), 3.90 (2H, d, J=7.6 Hz).

Step B: (1s,3R,5S)-1-((E)-4-(1,3-dioxoisoindolin-2-yl)but-2-en-1-yl)-1,3,5,7-tetraaza-adamantan-1-ium bromide To a solution of (E)-2-(4-bromobut-2-en-1-yl)isoindoline-1,3-dione (9.86 g, 35.2 mmol) in $CHCl_3$ (98 mL) was added hexamethylenetetraamine (7.40 g, 52.8 mmol) at room temperature. The reaction mixture was stirred at room temperature for 26 hours. A precipitated solid was collected by filtration, washed with $CHCl_3$, and dried under vacuum to give title compound (14.4 g, 97%) as a white powder. $^1H$ NMR (400 MHz, $CD_3OD$): δ 7.90-7.82 (4H, m), 6.19-6.12 (1H, m), 5.93-5.85 (1H, m), 5.06 (6H, s), 4.73-4.70 (3H, m), 4.55-4.52 (3H, m), 4.41 (2H, d, J=5.6 Hz), 3.47 (2H, d, J=7.6 Hz).

Step C: (E)-2-(4-aminobut-2-en-1-yl)isoindoline-1,3-dione

To a solution of (1s,3R,5S)-1-((E)-4-(1,3-dioxoisoindolin-2-yl)but-2-en-1-yl)-1,3,5,7-tetraaza-adamantan-1-ium bromide (9.80 g, 23.3 mmol) in EtOH (192 mL) was added conc. HCl (9.80 mL, 118 mmol) at 0° C. The reaction mixture was refluxed for 2 hours. After concentration in vacuo, the residue was purified by crystallization from $Et_2O$/MeOH to give HCl salt form of title compound (5.89 g, quant.) as a white solid. The salt compound (5.89 g, 23.2 mmol) was dissolved in DCM/MeOH and then basified with 1 N aq. NaOH solution and saturated aq. $NaHCO_3$ solution until pH 8. The separated organic layer was washed with brine, dried over $Na_2SO_4$, filtered, and concentrated in vacuo. The residue was concentrated in vacuo to give the title compound (3.17 g, 63%) as a yellow solid. $^1H$ NMR (400 MHz, DMSO-$d_6$): δ 7.91-7.85 (4H, m), 5.91-5.59 (2H, m), 4.20 (1H, dd, J=5.6, 1.2 Hz), 3.43-3.38 (2H, m).

Intermediate 3: 1-ethyl-3-methyl-1H-pyrazole-5-carbonyl isothiocyanate

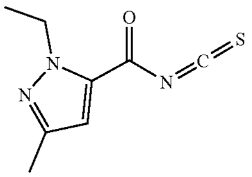

To a solution of 1-ethyl-3-methyl-1H-pyrazole-5-carboxylic acid (2.00 g, 13.0 mmol) in DCM (40 mL) was added DMF (1-2 drops) followed by oxalyl chloride (3.50 mL, 40.8 mmol) at 0° C. The reaction mixture was stirred at room temperature for 2 hours. After concentration in vacuo, the residue was dissolved in acetone (12 mL). The solution was added to a solution of potassium thiocyanate (1.64 g, 16.9 mmol) in acetone (28 mL) at 0° C. The reaction mixture was stirred at room temperature for 1 hour. After treatment of hexanes (20 mL), the mixture was concentrated in vacuo. The impurity was solidified from hexanes and DCM. The solid was filtered off and the filtrated was concentrated in vacuo. The residue was purified by column chromatography on $SiO_2$ (Hexanes:EtOAc=3:1 to 2:1) to give the title compound (1.83 g, 72% for 2 steps) as a yellow oil. $^1H$ NMR (400 MHz, $CDCl_3$): δ 6.72 (1H, s), 4.49 (2H, q, J=7.2 Hz), 2.28 (3H, s), 1.39 (3H, t, J=7.2 Hz).

Intermediate 4: tert-butyl 4-(chlorosulfonyl)piperazine-1-carboxylate

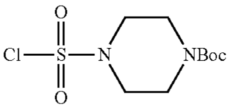 [SMILES: CC(C)(C)OC(=O)N1CCN(S(=O)(=O)Cl)CC1]

To a solution of sulfuryl chloride (0.0520 mL, 0.644 mmol) in DCM (2.0 mL) was added a mixture of tert-butyl piperazine-1-carboxylate (0.100 g, 0.537 mmol) and pyridine (0.0650 mL, 0.805 mmol) in DCM (0.250 mL) at 0° C. The reaction mixture was stirred at room temperature for 1 hour. After treatment with 1 N aq. HCl solution, the separated organic layer was washed with brine, dried over $Na_2SO_4$, concentrated in vacuo to give the title compound (54 mg, 35%). $^1H$ NMR (400 MHz, DMSO-$d_6$): δ 3.55 (4H, brs), 3.27 (4H, brs), 1.42 (9H, s).

Intermediate 5: 4-nitrophenyl cyclopropylcarbamate

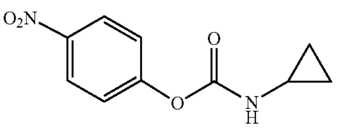 [SMILES: O=C(NC1CC1)Oc1ccc([N+](=O)[O-])cc1]

To a solution of 4-nitrophenyl carbonochloridate (1.77 g, 8.76 mmol) in THF (25 mL) was added cyclopropanamine (0.610 mL, 8.76 mmol) followed by DIPEA (3.06 mL, 17.5 mmol) at room temperature. The reaction mixture was stirred at room temperature for 1 hour. After quenched with water, the mixture was extracted with EtOAc twice. The combined organic layers were washed with brine, dried over $Na_2SO_4$, filtered, and concentrated in vacuo. The residue was purified by column chromatography on $SiO_2$ (Hexanes: EtOAc=3:1) to give the title compound (758 mg, 39%) as a pale yellow solid. $^1H$ NMR (400 MHz, DMSO-$d_6$): δ 8.27-8.23 (3H, m), 7.42-7.38 (2H, m), 2.60-2.56 (1H, m), 0.68-0.63 (2H, m), 0.54-0.50 (2H, m).

Intermediate 6: 1-(tert-butyl) 4-(4-nitrophenyl) piperazine-1,4-dicarboxylate

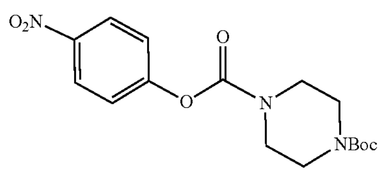 [SMILES: CC(C)(C)OC(=O)N1CCN(C(=O)Oc2ccc([N+](=O)[O-])cc2)CC1]

To a solution of 4-nitrophenyl chloroformate (0.541 g, 2.68 mmol) and TEA (0.561 mL, 4.03 mmol) in DCM (5.4 mL) was added tert-butyl piperazine-1-carboxylate (0.500 g, 2.68 mmol). The reaction mixture was stirred at room temperature for 3 hours. After quenched with water, the mixture was extracted with DCM twice. The combined organic layers were washed with brine, dried over $Na_2SO_4$, filtered, and concentrated in vacuo to afford the title compound (0.788 g, 84%) as a white solid. $^1H$ NMR (400 MHz, DMSO-$d_6$): δ 8.28 (2H, dd, J=6.8, 2.4 Hz), 7.45 (2H, dd, J=7.0, 2.2 Hz), 3.59 (1H, d, J=4.0 Hz), 3.41 (6H, brs), 1.42 (9H, s).

Intermediate 7: cyclopropyl (4-nitrophenyl) carbonate

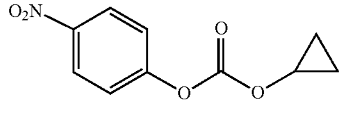 [SMILES: O=C(Oc1ccc([N+](=O)[O-])cc1)OC1CC1]

A mixture of cyclopropanol (0.545 mL, 8.61 mmol) and pyridine (2.79 mL, 34.4 mmol) in DCM (86 mL) was stirred at room temperature for 10 min and cooled to 0° C. After addition of 4-nitrophenyl carbonochloridate (3.47 g, 17.2 mmol), the reaction mixture was stirred at room temperature for 19 hours. After concentration in vacuo, the residue was suspended in a mixture of EtOAc and hexanes (v/v=1:1) and then stirred at room temperature for 10 minutes. The organic solvent was carefully decanted. (3 times repeated). The combined organic layers were concentrated in vacuo. The residue was purified by column chromatography on $SiO_2$ (Hexanes only to Hexanes:EtOAc=8:1) to give the title compound (0.700 g, 36%) as a white solid. $^1H$ NMR (400 MHz, $CDCl_3$): δ 8.31-8.26 (2H, m), 7.41-7.37 (2H m), 4.31-4.26 (1H, m), 0.91-0.89 (2H, m), 0.84-0.82 (2H, m).

Intermediate 8: tert-butyl 4-(((4-nitrophenoxy)carbonyl)oxy)piperidine-1-carboxylate

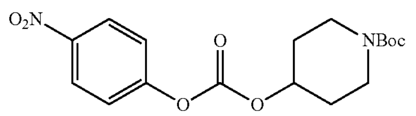 [SMILES: CC(C)(C)OC(=O)N1CCC(OC(=O)Oc2ccc([N+](=O)[O-])cc2)CC1]

To a solution of tert-butyl 4-hydroxypiperidine-1-carboxylate (0.100 g, 0.497 mmol) and TEA (0.104 mL, 0.745 mmol) in DCM (0.66 mL) was added 4-nitrophenyl carbonochloridate (0.110 g, 0.547 mmol). The reaction mixture was stirred at room temperature for 2 hours. After concentration in vacuo, the residue was purified by column chromatography on $SiO_2$ (Hexanes:EtOAc=4:1) to afford the title compound (98 mg, 54%). $^1H$ NMR (400 MHz, DMSO-$d_6$): δ 8.32 (2H, d, J=9.2 Hz), 7.58 (2H, d, J=12.4 Hz), 4.91-4.87 (1H, m), 3.63-3.57 (2H, m), 3.22 (2H, t, J=9.5 Hz), 1.96-1.91 (2H, m), 1.63-1.61 (2H, m), 1.41 (9H, s).

Intermediate 9: cyclopentyl (4-nitrophenyl) carbonate

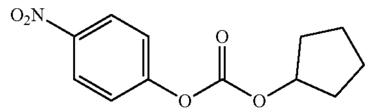 [SMILES: O=C(Oc1ccc([N+](=O)[O-])cc1)OC1CCCC1]

To a solution of cyclopentanol (0.527 mL, 5.80 mmol) in pyridine (1.8 mL) was added 4-nitrophenyl chloroformate (2.34 g, 11.6 mmol) at 0° C. The reaction mixture was stirred at room temperature for 3 hours. A precipitated solid was suspended in DCM and filtered off. The filtrate was concentrated in vacuo. The residue was purified by column chromatography on $SiO_2$ (Hexanes:EtOAc=20:1 to 9:1) to afford the title compound (1.22 g, 84%) as a colorless oil. $^1H$ NMR (400 MHz, DMSO-$d_6$): δ 8.30 (2H, td, J=6.2, 3.7 Hz), 7.55 (2H, td, J=6.2, 3.7 Hz), 5.16-5.13 (1H, m), 1.92-1.78 (4H, m), 1.72-1.58 (4H, m).

Intermediate 10: 2-((tert-butyldimethylsilyl)oxy)ethyl (4-nitrophenyl) carbonate

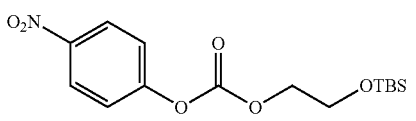 [SMILES: CC(C)(C)[Si](C)(C)OCCOC(=O)Oc1ccc([N+](=O)[O-])cc1]

To a stirred solution of ethylene glycol (0.0900 mL, 1.61 mmol) in DCM (5.3 mL) was added pyridine (0.391 mL, 4.83 mmol) followed by TBS-Cl (0.292 mL, 1.69 mmol) at room temperature. The mixture was stirred at room temperature for 2 hours. After addition of 4-nitrophenyl-chloroformate (0.325 g, 1.61 mmol), the reaction mixture was stirred at room temperature for 2 hours. After concentration in vacuo, the residue was purified by column chromatography on $SiO_2$ (Hexanes:EtOAc=99:1 to 10:1) to give the title compound (0.158 g, 28%) as a colorless oil. $^1H$ NMR (400

MHz, $CDCl_3$): δ 8.28 (2H, dt, J=8.8, 2.6 Hz), 7.38 (2H, dt, J=8.4, 2.8 Hz), 4.36 (2H, t, J=4.8 Hz), 3.91 (2H, t, J=4.8 Hz), 0.91 (9H, s), 0.10 (6H, s).

Intermediate 11: 4-nitrophenyl 4-((tert-butyldimethylsilyl)oxy)piperidine-1-carboxylate

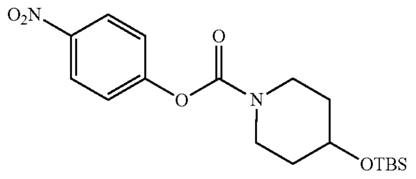 [SMILES: CC(C)(C)[Si](C)(C)OC1CCN(C(=O)Oc2ccc([N+](=O)[O-])cc2)CC1]

Step A: 4-((tert-butyldimethylsilyl)oxy)piperidine

To a solution of piperidin-4-ol (0.197 mL, 1.98 mmol) in DCM (4.0 mL) was added 1H-imidazole (0.538 g, 7.91 mmol) followed by TBS-Cl (0.715 g, 4.75 mmol) at room temperature. The reaction mixture was stirred at room temperature for 1 hour. After quenched with water, the mixture was extracted with DCM twice. The combined organic layers were dried over $Na_2SO_4$, filtered, and concentrated in vacuo. The residue was purified by column chromatography on $SiO_2$ (DCM:MeOH:$NH_4OH$=100:10:1) to afford the title compound (0.436 g, quant.) as a colorless oil. $^1H$ NMR (400 MHz, $CDCl_3$): δ 3.77-3.71 (1H, m), 3.09-3.03 (2H, m), 2.65-2.58 (2H, m), 1.80-1.74 (2H, m), 1.43 (2H, tt, J=12.9, 4.6 Hz), 0.88 (9H, s), 0.05 (6H, s).

Step B: 4-nitrophenyl 4-((tert-butyldimethylsilyl)oxy)piperidine-1-carboxylate To a solution of 4-((tert-butyldimethylsilyl)oxy)piperidine (0.426 g, 1.98 mmol) in DCM (6.6 mL) was added pyridine (0.322 mL, 3.96 mmol) followed by 4-nitrophenyl carbonochloridate (0.399 g, 1.98 mmol) at room temperature. The reaction mixture was stirred at room temperature overnight and then concentrated in vacuo. The residue was purified by column chromatography on $SiO_2$ (Hexanes: EtOAc=10:1) to afford the title compound (0.169 g, 23% for 2 steps) as a colorless oil. $^1H$ NMR (400 MHz, $CDCl_3$): δ 8.25 (2H, dt, J=8.2, 2.8 Hz), 7.29 (2H, dt, J=7.2, 2.8 Hz), 4.03-3.99 (1H, m), 3.80-3.74 (1H, m), 3.71-3.59 (2H, m), 3.58-3.52 (1H, m), 1.84-1.76 (2H, m), 1.65-1.59 (2H, m), 0.91 (9H, s), 0.08 (6H, s).

General Procedure for Alkynyloxy Intermediates

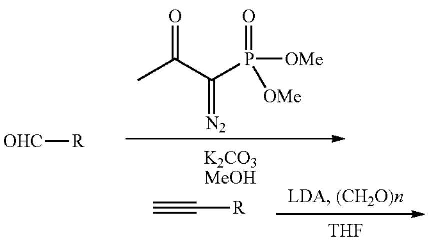

-continued

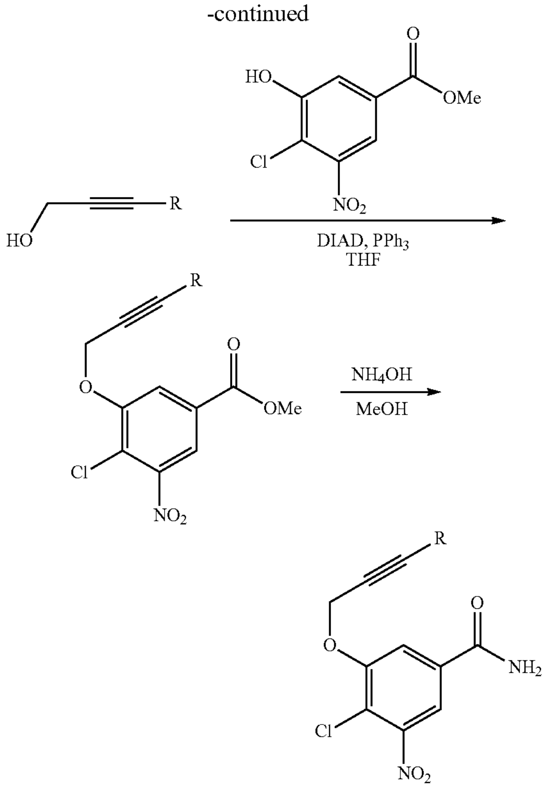

Intermediate 12: tert-butyl 3-(3-(5-carbamoyl-2-chloro-3-nitrophenoxy)prop-1-yn-1-yl)azetidine-1-carboxylate

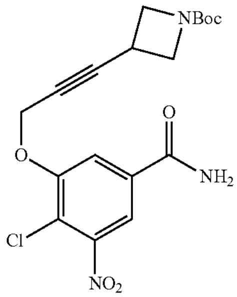 [SMILES: CC(C)(C)OC(=O)N1CC(C#CCOc2cc(C(N)=O)cc([N+](=O)[O-])c2Cl)C1]

Step A: tert-butyl 3-formylazetidine-1-carboxylate

To a solution of tert-butyl 3-(hydroxymethyl)azetidine-1-carboxylate (20.0 g, 107 mmol) in DCM (300 mL) was added Dess-Martin periodinane (90.6 g, 214 mmol) at 0° C. The reaction mixture was stirred at room temperature for 3 hours. After addition of 2 M aq. $Na_2S_2O_3$ solution at 0° C., the mixture was stirred for an additional 30 min at 0° C. After dilution with water, the mixture was extracted with DCM twice. The combined organic layers were washed with brine, dried over $Na_2SO_4$, filtered, and concentrated in vacuo. The residue was purified by column chromatography on $SiO_2$ (pet.Ether:EtOAc=1:1) to give the title compound (13.9 g, 42%) as a colorless oil. $^1H$ NMR (400 MHz, $CDCl_3$): δ 9.85 (1H, d, J=2.1 Hz), 4.16-4.06 (4H, m), 1.44 (1H, s), 1.44 (9H, s). LC-MS: m/z=257.01 [M−56]$^+$ Step B: tert-butyl 3-ethynylazetidine-1-carboxylate To a mixture of tert-butyl 3-formylazetidine-1-carboxylate (12.9 g, 69.6 mmol) and $K_2CO_3$ (28.9 g, 209 mmol) in MeOH (150 mL) was added dimethyl (1-diazo-2-oxopropyl) phosphonate (14.9 g, 83.6 mmol) at 0° C. The reaction mixture was stirred at room temperature overnight. After concentration in vacuo, the residue was dissolved in water and then extracted with $Et_2O$ twice. The combined organic layers were washed with brine, dried over $Na_2SO_4$, filtered, and concentrated in vacuo. The residue was purified by column chromatography on $SiO_2$ (pet.Ether:EtOAc=10:1) to give the title compound (8.80 g, 70%) as a yellow oil. $^1$H NMR (400 MHz, $CDCl_3$): δ 4.14 (2H, t, J=8.6 Hz), 3.94 (2H, dd, J=8.3, 6.4 Hz), 3.30 (1H, ttd, J=8.8, 6.3, 2.5 Hz), 2.28 (1H, d, J=2.5 Hz), 1.44 (9H, s). LC-MS: m/z=126.0 [M−56]$^+$ Step C: tert-butyl 3-(3-hydroxyprop-1-yn-1-yl)azetidine-1-carboxylate To a solution of tert-butyl 3-ethynylazetidine-1-carboxylate (8.10 g, 44.7 mmol) in THF (150 mL) was added dropwise LDA (2 M in THF, 14.4 g, 134 mmol) at −78° C. The mixture was stirred at −78° C. for 30 minutes. After addition of paraformaldehyde (21.1 g, 134 mmol) at −78° C., the reaction mixture was stirred at room temperature for 1.5 hours. After quenched with saturated aq. $NH_4Cl$ solution, the mixture was extracted with EtOAc twice. The combined organic layers were washed with brine, dried over $Na_2SO_4$ and filtered and concentrated in vacuo. The residue was purified by column chromatography on $SiO_2$ (DCM: EtOAc=2:1) to give the title compound (5.37 g, 55%) as a yellow oil. $^1$H NMR (400 MHz, $CDCl_3$): δ 4.29 (2H, d, J=2.0 Hz), 4.13 (2H, t, J=8.5 Hz), 3.92 (2H, dd, J=8.2, 6.3 Hz), 3.34 (1H, ttt, J=8.4, 6.3, 2.0 Hz), 1.44 (9H, s). LC-MS: m/z=156.0 [M−56]$^+$ Step D: tert-butyl 3-(3-(2-chloro-5-(methoxycarbonyl)-3-nitrophenoxy)prop-1-yn-1-yl)azetidine-1-carboxylate To a solution of methyl 4-chloro-3-hydroxy-5-nitrobenzoate (1.20 g, 5.21 mmol) in THF (23 mL) was successively added tert-butyl 3-(3-hydroxyprop-1-yn-1-yl)azetidine-1-carboxylate (1.00 g, 4.73 mmol), DIAD (1.10 mL, 5.68 mmol) and $PPh_3$ (1.49 g, 5.68 mmol) at 0° C. The reaction mixture was stirred at room temperature overnight. After quenched with water, the mixture was extracted with EtOAc twice. The combined organic layers were dried over $Na_2SO_4$, filtered and concentrated in vacuo. The residue was purified by column chromatography on $SiO_2$ (Hexanes: EtOAc=3:1) to afford the title compound (3.26 g, >99%) as a colorless oil. $^1$H NMR (400 MHz, DMSO-$d_6$): □□ 8.14 (1H, d, J=2.0 Hz), 8.00 (1H, d, J=2.0 Hz), 5.20 (2H, d, J=2.0 Hz), 4.09 (2H, t, J=9.4 Hz), 3.92 (3H, s), 3.69 (2H, t, J=6.8 Hz), 3.50-3.48 (1H, m), 1.36 (9H, s).

Step E: tert-butyl 3-(3-(5-carbamoyl-2-chloro-3-nitrophenoxy)prop-1-yn-1-yl)azetidine-1-carboxylate To a solution of tert-butyl 3-(3-(2-chloro-5-(methoxycarbonyl)-3-nitrophenoxy)prop-1-yn-1-yl)azetidine-1-carboxylate (1.94 g, 4.57 mmol) was added $NH_4OH$ (21.3 mL, 137 mmol) at room temperature. The reaction mixture was stirred at 50° C. for 3 hours. After dilution with water, the mixture was extracted with DCM, dried over $Na_2SO_4$, filtered, and concentrated in vacuo. The residue was purified by column chromatography on $SiO_2$ (DCM only to DCM: MeOH=98:2) to afford the title compound (0.977 g, 52% for 2 steps) as a yellow oil. $^1$H NMR (400 MHz, DMSO-$d_6$): □□ 8.27 (1H, s), 8.12 (1H, d, J=2.0 Hz), 7.98 (1H, d, J=1.6 Hz), 7.81 (1H, s), 5.14 (2H, d, J=1.6 Hz), 4.07 (2H, t, J=8.4 Hz), 3.70 (2H, t, J=6.8 Hz), 3.51-3.47 (1H, m), 1.36 (9H, s).

Intermediate 13: tert-butyl 3-(3-(5-carbamoyl-2-chloro-3-nitrophenoxy)prop-1-yn-1-yl)pyrrolidine-1-carboxylate

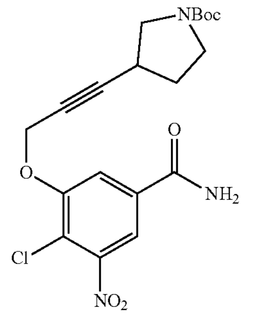 [SMILES: CC(C)(C)OC(=O)N1CCC(C#CCOc2cc(C(N)=O)cc([N+](=O)[O-])c2Cl)C1]

Step A: tert-butyl 3-ethynylpyrrolidine-1-carboxylate

The title compound was prepared in a similar fashion to Intermediate 12 (Step B) with tert-butyl 3-formylpyrrolidine-1-carboxylate. The crude product was used for the next reaction without purification. $^1$H NMR (400 MHz, $CDCl_3$): δ 3.72-3.42 (2H, m), 3.30 (2H, d, J=17.8 Hz), 2.94 (1H, s), 2.20-2.11 (1H, m), 2.11 (1H, d, J=2.3 Hz), 2.01-1.87 (1H, m), 1.46 (9H, s).

LC-MS: m/z=140.0 [M−56]$^+$

Step B: tert-butyl 3-(3-hydroxyprop-1-yn-1-yl)pyrrolidine-1-carboxylate

The title compound was prepared in a similar fashion to Intermediate 12 (Step C) with tert-butyl 3-ethynylpyrrolidine-1-carboxylate. The crude product was purified by column chromatography on $SiO_2$ (DCM:EtOAc=10:1) to afford the title compound (73%) as a yellow oil. $^1$H NMR (400 MHz, $CDCl_3$): δ 4.26 (2H, d, J=2.0 Hz), 3.61 (1H, dd, J=10.6, 7.3 Hz, 1H), 3.49 (1H, ddd, J=12.2, 7.9, 4.6 Hz), 3.39-3.20 (2H, m), 3.06-2.92 (1H, m), 2.13 (1H, dtd, J=11.7, 6.8, 4.7 Hz), 1.91 (1H, dq, J=12.3, 8.0 Hz), 1.46 (9H, s). LC-MS: m/z=170.0 [M+H]$^+$ Step C: tert-butyl 3-(3-(2-chloro-5-(methoxycarbonyl)-3-nitrophenoxy)prop-1-yn-1-yl)pyrrolidine-1-carboxylate The title compound was prepared in a similar fashion to Intermediate 12 (Step D) with methyl 4-chloro-3-hydroxy-5-nitrobenzoate and tert-butyl 3-(3-hydroxyprop-1-yn-1-yl) pyrrolidine-1-carboxylate. The crude product was purified by column chromatography on $SiO_2$ (Hexanes:EtOAc=3:1)

to afford the title compound (>99%) as a colorless oil. $^1H$ NMR (400 MHz, DMSO-$d_6$): δ 8.11 (1H, d, J=1.2 Hz), 7.98 (1H, d, J=1.6 Hz), 5.13 (2H, s), 3.91 (3H, s), 3.28-3.16 (2H, m), 3.10 (2H, s), 1.79-1.77 (1H, m), 1.38-1.35 (11H, m).

Step D: tert-butyl 3-(3-(5-carbamoyl-2-chloro-3-nitrophenoxy)prop-1-yn-1-yl)pyrrolidine-1-carboxylate The title compound was prepared in a similar fashion to Intermediate 12 (Step E) with tert-butyl 3-(3-(2-chloro-5-(methoxycarbonyl)-3-nitrophenoxy)prop-1-yn-1-yl)pyrrolidine-1-carboxylate. The crude product was purified by column chromatography on NH—$SiO_2$ (DCM:MeOH=95:5) to afford the title compound (37%) as a pale yellow solid. $^1H$ NMR (400 MHz, DMSO-$d_6$): δ 8.25 (1H, s), 8.11 (1H, d, J=1.2 Hz), 7.98 (1H, s), 7.78 (1H, s), 5.09 (2H, s), 3.47 (1H, d, J=4.4 Hz), 3.20 (1H, t, J=7.4 Hz), 3.11-3.08 (2H, m), 2.08-2.06 (1H, m), 1.81-1.75 (1H, m), 1.39-1.37 (10H, m).

Intermediate 14: tert-butyl 3-(3-hydroxyprop-1-yn-1-yl)piperidine-1-carboxylate

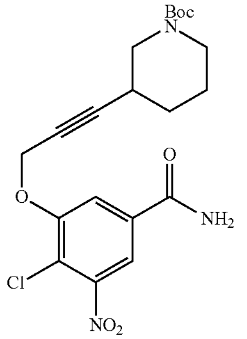 [SMILES: CC(C)(C)OC(=O)N1CCCC(C#CCOc2cc(C(N)=O)cc([N+](=O)[O-])c2Cl)C1]

Step A: tert-butyl 3-ethynylpiperidine-1-carboxylate

The title compound was prepared in a similar fashion to Intermediate 12 (Step B) with tert-butyl 3-formylpiperidine-1-carboxylate. The crude product was used for the next reaction without purification. $^1H$ NMR (400 MHz, $CDCl_3$): δ 3.92 (1H, d, J=13.8 Hz), 3.78-3.69 (1H, m), 3.07-2.93 (2H, m), 2.49-2.39 (1H, m), 2.06 (1H, d, J=2.4 Hz), 2.03-1.93 (1H, m), 1.71 (1H, dtt, J=13.8, 5.1, 3.4 Hz), 1.62-1.52 (1H, m), 1.46 (9H, s), 1.45-1.37 (1H, m). LC-MS: m/z=154.0 $[M-56]^+$.

Step B: tert-butyl 3-(3-hydroxyprop-1-yn-1-yl)piperidine-1-carboxylate

The title compound was prepared in a similar fashion to Intermediate 12 (Step C) with tert-butyl 3-ethynylpiperidine-1-carboxylate. The crude product was purified by column chromatography on $SiO_2$ (DCM:EtOAc=10:1) to afford the title compound (66%) as a yellow oil. $^1H$ NMR (400 MHz, $CDCl_3$) δ 4.25 (2H, d, J=2.0 Hz), 3.88 (1H, ddt, J=13.2, 4.0, 1.3 Hz), 3.72 (1H, dt, J=13.3, 4.6 Hz), 3.05-2.92 (2H, m), 2.47 (1H, ttt, J=9.4, 3.7, 1.9 Hz), 2.01-1.89 (1H, m), 1.75-1.67 (1H, m), 1.60-1.49 (1H, m), 1.46 (9H, s), 1.45-1.37 (1H, m). LC-MS: m/z=184.0 $[M-56]^+$.

Step C: tert-butyl 3-(3-(2-chloro-5-(methoxycarbonyl)-3-nitrophenoxy)prop-1-yn-1-yl)piperidine-1-carboxylate The title compound was prepared in a similar fashion to Intermediate 12 (Step D) with methyl 4-chloro-3-hydroxy-5-nitrobenzoate and tert-butyl 3-(3-hydroxyprop-1-yn-1-yl)piperidine-1-carboxylate. The crude product was purified by column chromatography on $SiO_2$ (Hexanes:EtOAc=3:1) to afford title compound (>99%) as a colorless oil. $^1H$ NMR (400 MHz, DMSO-$d_6$): □□ 8.14 (1H, d, J=2.0 Hz), 8.00 (1H, d, J=1.2 Hz), 5.14 (2H, d, J=1.2 Hz), 3.92 (3H, s), 3.07 (2H, s), 2.55-2.50 (2H, m), 1.82-1.80 (1H, m), 1.57-1.48 (2H, m), 1.38-1.30 (11H, m).

Step D: tert-butyl 3-(3-(5-carbamoyl-2-chloro-3-nitrophenoxy)prop-1-yn-1-yl)piperidine-1-carboxylate The title compound was prepared in a similar fashion to Intermediate 12 (Step E) with tert-butyl 3-(3-(2-chloro-5-(methoxycarbonyl)-3-nitrophenoxy)prop-1-yn-1-yl)piperidine-1-carboxylate. The crude product was purified by column chromatography on $SiO_2$ (DCM only to DCM:MeOH=9:1) to afford the title compound (68%) as a yellow oil. $^1H$ NMR (400 MHz, DMSO-$d_6$): □□ 8.26 (1H, s), 8.11 (1H, d, J=2.0 Hz), 7.98 (1H, d, J=1.6 Hz), 7.79 (1H, s), 5.08 (2H, d, J=2.0 Hz), 3.59 (2H, s), 3.04 (2H, s), 1.81 (1H, s), 1.59-1.47 (2H, m), 1.35 (9H, s), 1.34-1.29 (2H, m)

Intermediate 15: tert-butyl 4-(3-(5-carbamoyl-2-chloro-3-nitrophenoxy)prop-1-yn-1-yl)piperidine-1-carboxylate

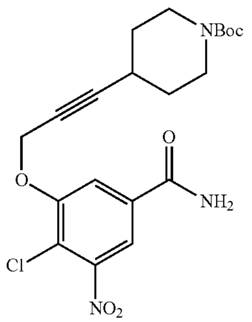 [SMILES: CC(C)(C)OC(=O)N1CCC(C#CCOc2cc(C(N)=O)cc([N+](=O)[O-])c2Cl)CC1]

Step A: tert-butyl 4-(3-hydroxyprop-1-yn-1-yl)piperidine-1-carboxylate

The title compound was prepared in a similar fashion to Intermediate 12 (Step C) with tert-butyl 4-ethynylpiperidine-1-carboxylate. The crude product was purified by column chromatography on $SiO_2$ (pet.Ether:EtOAc=2:1) to afford the title compound (85%) as a yellow oil. $^1H$ NMR (400 MHz, DMSO-$d_6$): δ 4.34-4.24 (2H, m), 3.71 (2H, ddd, J=13.4, 6.5, 3.8 Hz), 3.14 (2H, ddd, J=13.5, 8.7, 3.4 Hz), 2.60 (1H, dddt, J=8.2, 6.0, 3.9, 1.9 Hz), 1.77 (2H, ddt, J=13.6, 7.1, 3.7 Hz), 1.56 (2H, dtd, J=12.7, 8.6, 3.8 Hz), 1.45 (9H, s). LC-MS: m/z=240.3 $[M+H]^+$.

Step B: tert-butyl 4-(3-(2-chloro-5-(methoxycarbonyl)-3-nitrophenoxy)prop-1-yn-1-yl)piperidine-1-carboxylate The title compound was prepared in a similar fashion to Intermediate 12 (Step D) with methyl 4-chloro-3-hydroxy- 5-nitrobenzoate and tert-butyl 4-(3-hydroxyprop-1-yn-1-yl) piperidine-1-carboxylate. The crude product was purified by column chromatography on $SiO_2$ (Hexanes:EtOAc=3:1) to give the title compound (47%) as a colorless oil. $^1H$ NMR (400 MHz, $CDCl_3$): δ 8.06 (1H, d, J=1.2 Hz), 7.96 (1H, d, J=1.6 Hz), 4.91 (2H, d, J=1.6 Hz), 3.96 (3H, s), 3.61-3.59 (2H, m), 3.20-3.13 (2H, m), 2.62 (1H, m), 1.76-1.72 (2H, m), 1.57-1.49 (2H, m), 1.44 (9H, s).

Step C: tert-butyl 4-(3-(5-carbamoyl-2-chloro-3-nitrophenoxy)prop-1-yn-1-yl)piperidine-1-carboxylate The title compound was prepared in a similar fashion to Intermediate 12 (Step D) with tert-butyl 4-(3-(2-chloro-5-(methoxycarbonyl)-3-nitrophenoxy)prop-1-yn-1-yl)piperidine-1-carboxylate. The crude product was purified by column chromatography on NH—$SiO_2$ (DCM:MeOH=95:5) to afford the title compound (32%) as a white solid. $^1H$ NMR (400 MHz, $CDCl_3$): δ 8.25 (1H, s), 8.11 (1H, d, J=1.2 Hz), 8.01 (1H, d, J=2.0 Hz), 7.78 (1H, s), 5.10 (2H, d, J=1.2 Hz), 3.46 (2H, m), 3.09-3.05 (2H, m), 2.76-2.64 (1H, m), 1.70-1.65 (2H, m), 1.38 (11H, s).

Intermediate 16: methyl 4-chloro-3-((4-hydroxy-4-methylpent-2-yn-1-yl)oxy)-5-nitrobenzamide

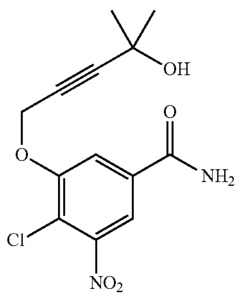 [SMILES: CC(C)(O)C#CCOc1cc(C(N)=O)cc([N+](=O)[O-])c1Cl]

Step A: 5-chloro-2-methylpent-3-yn-2-ol

To a solution of 3-chloroprop-1-yne (9.2 M in toluene, 4.38 mL, 40.3 mmol) in dry THF (134 mL) was added dropwise n-BuLi (2.5 M in hexanes, 16.1 mL, 40.3 mmol) at −78° C. The mixture was stirred at −78° C. for 30 min. After addition of dry acetone (2.96 mL, 40.3 mmol) over 5 minutes, the reaction mixture was stirred at −78° C. for 3 hours and warmed to 0° C. After quenched with 1 M aq. $NH_4Cl$ solution, the mixture was extracted with $Et_2O$ twice. The combined organic layers were washed with brine, dried over $Na_2SO_4$, filtered, and concentrated in vacuo. The residue was purified by column chromatography on $SiO_2$ (Hexanes:EtOAc=4:1) to give the title compound (4.39 g, 82%) as a colorless oil. $^1H$ NMR (400 MHz, $CDCl_3$): δ 4.12 (2H, s), 2.78 (1H, s), 1.48 (6H, s).

Step B: methyl 4-chloro-3-((4-hydroxy-4-methylpent-2-yn-1-yl)oxy)-5 -nitrobenzoate A mixture of methyl 4-chloro-3-hydroxy-5-nitrobenzoate (500 mg, 2.16 mmol) and $K_2CO_3$ (358 mg, 2.59 mmol) in DMF (2.2 mL) was stirred at room temperature for 30 min. After addition of 5-chloro-2-methylpent-3-yn-2-ol (315 mg, 2.38 mmol) at room temperature, the reaction mixture was stirred at 70° C. overnight. After filtration through a Celite pad while washing with EtOAc, the filtrate was washed with water and brine, dried over $Na_2SO_4$, filtered, and concentrated in vacuo. The residue was purified by column chromatography on $SiO_2$ (Hexanes:EtOAc=3:1 to 1:1) to afford the title compound (578 mg, 82%) as a yellow oil. $^1H$ NMR (400 MHz, $CDCl_3$): 7.98 (1H, d, J=1.2 Hz), 7.91 (1H, d, J=1.6 Hz), 4.88 (2H, s), 3.92 (3H, s), 2.84 (1H, s), 1.45 (6H, s).

Step C: methyl 4-chloro-3-((4-hydroxy-4-methylpent-2-yn-1-yl)oxy)-5-nitrobenzamide The title compound was prepared in a similar fashion to Intermediate 12 (Step E) with methyl 4-chloro-3-((4-hydroxy-4-methylpent-2-yn-1-yl)oxy)-5-nitrobenzoate (1.05 g, 3.20 mmol). The crude product was purified by column chromatography on NH—$SiO_2$ (DCM:MeOH=95:5) to afford the title compound (62%) as a yellow solid. $^1H$ NMR (400 MHz, DMSO-$d_6$): δ 8.26 (1H, s), 8.10 (1H, d, J=2.0 Hz), 7.97 (1H, d, J=1.2 Hz), 7.80 (1H, s), 5.44 (1H, s), 5.10 (2H, s), 1.33 (6H, s).

Intermediate 17: 2-(dimethylamino)ethyl (4-nitrophenyl) carbonate hydrochloride

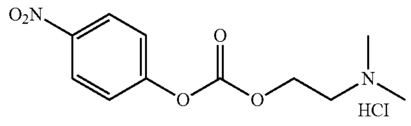

To a solution of 2-(dimethylamino)ethan-1-ol (0.562 mL, 5.61 mmol) in THF (19 mL) was added 4-nitrophenyl carbonochloridate (1.13 g, 5.61 mmol) at 0° C. The reaction mixture was stirred at room temperature for 3 hours. After treatment of EtOAc, a precipitated solid was collected by filtration, washed with EtOAc and dried under vacuum to afford the title compound (1.34 g, 82%) as a white solid. $^1H$ NMR (400 MHz, DMSO-$d_6$): δ 8.13-8.09 (2H, m), 6.98-6.94 (2H, m), 5.33 (1H, brs), 3.72 (2H, s), 3.10-3.13 (2H, m), 2.76 (6H, s).

Intermediate 18: tert-butyl 4-(4-(5-carbamoyl-2-chloro-3-nitrophenoxy)but-2-yn-1-yl)piperazine-1-carboxylate

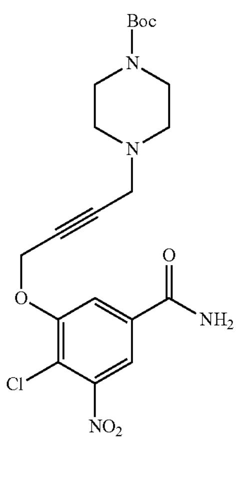 [SMILES: CC(C)(C)OC(=O)N1CCN(CC#CCOc2cc(C(N)=O)cc([N+](=O)[O-])c2Cl)CC1]

Step A: tert-butyl 4-(4-hydroxybut-2-yn-1-yl) piperazine-1-carboxylate

To a solution of tert-butyl piperazine-1-carboxylate (6.20 g, 33.3 mmol) and $K_2CO_3$ (4.60 g, 33.3 mmol) in DMF (80 mL) was added 4-[(4-methylbenzenesulfonyl)oxy]but-2-yn-1-ol (4.00 g, 16.6 mmol) at room temperature. The reaction mixture was stirred at room temperature for 2 hours. After partitioned between EtOAc and water, the separated aqueous layer was extracted with EtOAc. The combined organic layers were washed with brine, dried over $Na_2SO_4$, filtered, and concentrated in vacuo. The residue was purified by column chromatography on $SiO_2$ (pet. Ether:EtOAc=1:1) to afford the title compound (2.30 g, 54%) as a pale yellow oil. $^1$H NMR (400 MHz, $CDCl_3$): δ 4.28 (2H, t, J=1.9 Hz), 3.47 (4H, t, J=5.1 Hz), 3.33 (2H, t, J=2.0 Hz), 2.99 (1H, s), 2.51 (4H, t, J=5.1 Hz), 1.46 (9H, s). LC-MS: m/z=255 $[M+H]^+$.

Step B: tert-butyl 4-(4-(2-chloro-5-(methoxycarbonyl)-3-nitrophenoxy)but-2-yn-1-yl)piperazine-1-carboxylate The title compound was prepared in a similar fashion to Intermediate 12 (Step D) with methyl 4-chloro-3-hydroxy-5-nitrobenzoate and tert-butyl 4-(4-hydroxybut-2-yn-1-yl) piperazine-1-carboxylate. The crude product was purified by column chromatography on $SiO_2$ (Hexanes:EtOAc=1/1 to DCM:MeOH=98/2) to afford the title compound (quant.) as a colorless oil. $^1$H NMR (400 MHz, $CDCl_3$): δ 8.07 (1H, d, J=1.2 Hz), 7.92 (1H, d, J=1.2 Hz), 4.94 (2H, t, J=1.6 Hz), 3.97 (3H, s), 3.43 (4H, t, J=4.8 Hz), 3.34 (2H, t, J=1.6 Hz), 2.45 (4H, s), 1.46 (9H, s). LC-MS: m/z=468.1 $[M+H]^+$.

Step C: tert-butyl 4-(4-(5-carbamoyl-2-chloro-3-nitrophenoxy)but-2-yn-1-yl)piperazine-1-carboxylate The title compound was prepared in a similar fashion to Intermediate 12 (Step E) with tert-butyl 4-(4-(2-chloro-5-(methoxycarbonyl)-3-nitrophenoxy)but-2-yn-1-yl)piperazine-1-carboxylate. The crude product was purified by column chromatography on $SiO_2$ (DCM only to DCM:MeOH=9:1) to afford the title compound (36%) as a yellow solid. $^1$H NMR (400 MHz, DMSO-$d_6$): □□ 8.26 (1H, s), 8.11 (1H, d, J=1.6 Hz), 7.99 (1H, d, J=2.0 Hz), 7.79 (1H, s), 5.15 (2H, s), 3.29-3.26 (4H, m), 2.32 (4H, t, J=4.4 Hz), 1.38 (9H, s). LC-MS: m/z=453.1 $[M+H]^+$.

Intermediate 19: isopropyl 4-(4-(5-carbamoyl-2-chloro-3-nitrophenoxy)but-2-yn-1-yl)piperazine-1-carboxylate

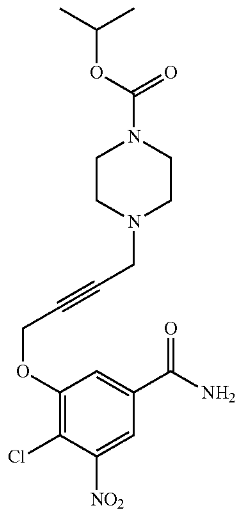 [SMILES: CC(C)OC(=O)N1CCN(CC#CCOc2cc(C(N)=O)cc([N+](=O)[O-])c2Cl)CC1]

Step A: isopropyl 4-(4-(2-chloro-5-(methoxycarbonyl)-3-nitrophenoxy)but-2-yn-1-yl)piperazine-1-carboxylate The title compound was prepared in a similar fashion to Intermediate 12 (Step D) with isopropyl 4-(4-hydroxybut-2-yn-1-yl)piperazine-1-carboxylate and methyl 4-chloro-3-hydroxy-5-nitrobenzoate. The crude product was purified by column chromatography on NH—$SiO_2$ (Hexanes: EtOAc=2:1 to 1:1) followed by on $SiO_2$ (Hexanes: EtOAc=1:1 to EtOAc:MeOH=10:1) to give the title compound (93%) as a yellow oil. $^1$H NMR (400 MHz, $CDCl_3$): δ 8.06 (1H, d, J=1.6 Hz), 7.91 (1H, d, J=1.6 Hz), 4.94 (2H, t, J=2.0 Hz), 4.92-4.86 (1H, m), 3.97 (3H, s), 3.48-3.46 (4H, m), 3.35 (2H, t, J=2.0 Hz), 2.45 (4H, brs), 1.24 (6H, d, J=6.0 Hz).

Step B: isopropyl 4-(4-(5-carbamoyl-2-chloro-3-itrophenoxy)but-2-yn-1-yl)piperazine-1-carboxylate The title compound was prepared in a similar fashion to Intermediate 12 (Step E) with isopropyl 4-(4-(2-chloro-5-(methoxycarbonyl)-3-nitrophenoxy)but-2-yn-1-yl)piperazine-1-carboxylate. The crude product was purified by column chromatography on NH—$SiO_2$ (DCM:EtOAc=7:3 to DCM:MeOH=20:1) to give the title compound (50%) as a pale yellow solid. $^1$H NMR (400 MHz, $CDCl_3$): δ 8.42 (1H, s), 8.13 (1H, s), 7.59 (1H, s), 7.43 (1H, s), 5.74 (2H, brs), 4.89 (1H, t, J=6.0 Hz), 4.78 (2H, s), 4.26 (3H, s), 3.91 (2H, s), 3.85 (2H, s), 3.44 (4H, s), 3.34 (2H, s), 2.40 (4H, s), 1.23 (6H, d, J=6.0 Hz).

Intermediate 20: 4-chloro-3-((4-(4-isobutyrylpiperazin-1-yl)but-2-yn-1-yl)oxy)-5-nitrobenzamide

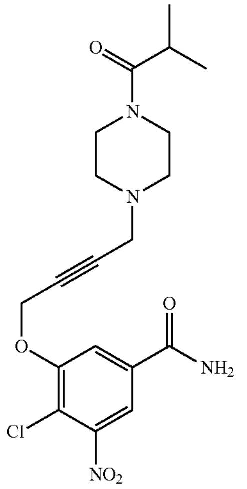 [SMILES: CC(C)C(=O)N1CCN(CC#CCOc2cc(C(N)=O)cc([N+](=O)[O-])c2Cl)CC1]

Step A: 2-methyl-1-(piperazin-1-yl) propan-1-one

To a solution of piperazine (20.2 g, 235 mmol) in AcOH (50 mL) was slowly added isobutyryl chloride (5.00 g, 46.9 mmol) at room temperature. The reaction mixture was stirred at room temperature for 2 hours. After basified until pH 9 with 1 N aq. NaOH, the mixture was extracted with DCM twice. The combined organic layers were washed with brine, dried over $Na_2SO_4$, filtered, and concentrated in vacuo. The residue was purified by column chromatography on $SiO_2$ (pet.Ether:EtOAc=9:1) to afford the title compound (6.00 g, 82%) as a colorless oil. LC-MS: m/z=157 $[M+H]^+$.

Step B: 1-[4-(4-hydroxybut-2-yn-1-yl) piperazin-1-yl]-2-methylpropan-1-one

The title compound was prepared in a similar fashion to Intermediate 18 (Step A) with 2-methyl-1-(piperazin-1-yl) propan-1-one and 4-[(4-methylbenzenesulfonyl) oxy]but-2-yn-1-ol. The crude product was purified by column chromatography on $SiO_2$ (EtOAc:MeOH=10:1) to give the title compound (15%) as a pale yellow oil. $^1$H NMR (400 MHz, $CDCl_3$): δ 4.30 (2H, d, J=1.9 Hz), 3.68 (2H, q, J=14.9, 10.1 Hz), 3.57 (2H, t, J=5.1 Hz), 3.37 (2H, d, J=2.0 Hz), 2.80 (1H, hept, J=6.7 Hz), 2.57 (4H, dt, J=11.1, 4.9 Hz), 2.23 (1H, s), 1.14 (6H, d, J=6.7 Hz). LC-MS: m/z=225 $[M+H]^+$.

Step C: methyl 4-chloro-3-((4-(4-isobutyrylpiperazin-1-yl)but-2-yn-1-yl)oxy)-5-nitrobenzoate The title compound was prepared in a similar fashion to Intermediate 12 (Step D) with methyl 4-chloro-3-hydroxy-5-nitrobenzoate and 1-(4-(4-hydroxybut-2-yn-1-yl)piperazin-1-yl)-2-methylpropan-1-one. The crude product was purified by column chromatography on $SiO_2$ (Hexanes: EtOAc=3:1) to afford the title compound (>99%) as a colorless oil. $^1$H NMR (400 MHz, $CDCl_3$): δ 8.14 (1H, d, J=1.6 Hz), 7.99 (1H, d, J=2.0 Hz), 5.22 (2H, s), 3.92 (3H, s), 3.40 (6H, m), 2.84-2.77 (1H, m), 2.35-2.34 (4H, m), 0.95 (6H, d, J=6.8 Hz). LC-MS: m/z=438.1 $[M+H]^+$.

Step D: 4-chloro-3-((4-(4-isobutyrylpiperazin-1-yl) but-2-yn-1-yl)oxy)-5-nitrobenzamide The title compound was prepared in a similar fashion to Intermediate 12 (Step E) with methyl 4-chloro-3-((4-(4-isobutyrylpiperazin-1-yl)but-2-yn-1-yl)oxy)-5-nitrobenzoate. The crude product was purified by column chromatography on $SiO_2$ (DCM only to DCM:MeOH=98:2) to afford the title compound (29% for 2 steps) as a yellow solid. $^1$H NMR (400 MHz, DMSO-$d_6$): □□ 8.25 (1H, s), 8.11 (1H, d, J=2.0 Hz), 7.99 (1H, d, J=2.0 Hz), 7.79 (1H, s), 5.15 (2H, s), 3.42 (4H, s), 3.36 (2H, s), 2.82 (1H, t, J=7.2 Hz), 2.38 (2H, s), 2.33 (2H, s), 0.96 (6H, d, J=6.4 Hz). LC-MS: m/z=423.1 $[M+H]^+$.

Intermediate 21: 4-chloro-3-((4-morpholinobut-2-yn-1-yl)oxy)-5-nitrobenzamide

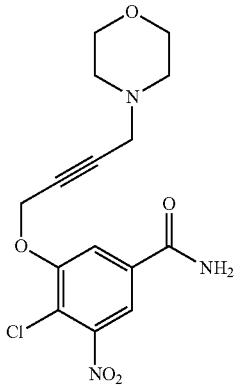 [SMILES: NC(=O)c1cc(OCC#CCN2CCOCC2)c(Cl)c([N+](=O)[O-])c1]

Step A: 4-(morpholin-4-yl) but-2-yn-1-ol

The title compound was prepared in a similar fashion to Intermediate 18 (Step A) with morpholine and 4-[(4-methylbenzenesulfonyl) oxy]but-2-yn-1-ol. The crude product was purified by column chromatography on $SiO_2$ (pet.Ether: EtOAc=9:1) to afford the title compound (93%) as a pale yellow oil. $^1$H NMR (400 MHz, $CDCl_3$): δ 4.28 (2H, t, J=2.0 Hz), 3.78-3.71 (4H, m), 3.67 (1H, s), 3.31 (2H, t, J=2.0 Hz), 2.58 (4H, dd, J=5.7, 3.8 Hz). LC-MS: m/z=156.0 $[M+H]^+$.

Step B: methyl 4-chloro-3-((4-morpholinobut-2-yn-1-yl)oxy)-5-nitrobenzoate

The title compound was prepared in a similar fashion to Intermediate 12 (Step D) with methyl 4-chloro-3-hydroxy-5-nitrobenzoate and 4-morpholinobut-2-yn-1-ol. The crude product was purified by column chromatography on $SiO_2$ (Hexanes:EtOAc=3:1) to afford the title compound (quant.) as a colorless oil. $^1$H NMR (400 MHz, DMSO-$d_6$): δ 8.15 (1H, d, J=1.6 Hz), 8.01 (1H, d, J=2.0 Hz), 5.23 (2H, s), 3.91 (3H, s), 3.51 (4H, t, J=4.4 Hz), 3.33 (2H, d, J=1.6 Hz), 2.34 (4H, t, J=4.8 Hz).

Step C: 4-chloro-3-((4-morpholinobut-2-yn-1-yl) oxy)-5-nitrobenzamide

The title compound was prepared in a similar fashion to Intermediate 12 (Step E) with methyl 4-chloro-3-((4-morpholinobut-2-yn-1-yl)oxy)-5-nitrobenzoate. The crude product was purified by column chromatography on NH—$SiO_2$ (DCM:MeOH=95:5) to afford the title compound (60%) as a yellow solid. $^1$H NMR (400 MHz, DMSO-$d_6$): δ 8.25 (1H, s), 8.11 (1H, d, J=2.0 Hz), 8.01 (1H, d, J=2.0 Hz), 7.80 (1H, s), 5.16 (2H, s), 3.52 (4H, t, J=4.8 Hz), 3.31 (2H, d, J=2.0 Hz), 2.35 (4H, t, J=4.8 Hz).

Intermediate 22: tert-butyl 4-(5-(5-carbamoyl-2-chloro-3-nitrophenoxy)-2-methylpent-3-yn-2-yl) piperazine-1-carboxylate

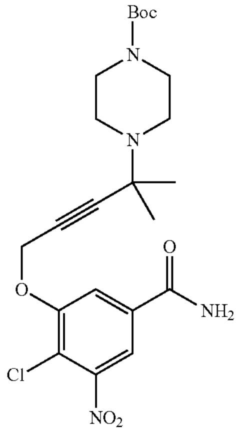 [SMILES: CC(C)(C)OC(=O)N1CCN(C(C)(C)C#CCOc2cc(C(N)=O)cc([N+](=O)[O-])c2Cl)CC1]

Step A: tert-butyl 4-(2-methylbut-3-yn-2-yl) piperazine-1-carboxylate

To a mixture of tert-butyl piperazine-1-carboxylate (6.00 g, 32.2 mmol), CuCl (0.320 g, 3.22 mmol) and TEA (6.52 g, 64.4 mmol) in THF (60 mL) was added 3-chloro-3-methylbuty-1-yne (3.63 g, 35.4 mmol) at 0° C. The reaction mixture was stirred at room temperature for 5 hours. After quenched with iced water, the mixture was extracted with EtOAc twice. The combined organic layers were washed with brine, dried over $Na_2SO_4$, filtered, and concentrated in vacuo. The residue was purified by column chromatography on $SiO_2$ (pet.Ether:EtOAc=6:1) to afford the title compound (7.00 g, 86%) as a colorless oil. $^1$H NMR (400 MHz, DMSO-$d_6$): δ 3.31 (4H, t, J=5.0 Hz), 3.18 (1H, s), 2.45 (4H, t, J=5.1 Hz), 1.39 (9H, s), 1.30 (6H, s).

Step B: tert-butyl 4-(5-hydroxy-2-methylpent-3-yn-2-yl) piperazine-1-carboxylate The title compound was prepared in a similar fashion to Intermediate 12 (Step C) with tert-butyl 4-(2-methylbut-3-yn-2-yl) piperazine-1-carboxylate. The crude product was purified by column chromatography on $SiO_2$ (DCM: EtOAc=1:1) to afford the title compound (31%) as a pale yellow oil. $^1$H NMR (400 MHz, DMSO-$d_6$): δ 5.08 (1H, t, J=5.9 Hz), 4.07 (2H, d, J=5.9 Hz), 3.30 (4H, d, J=4.9 Hz), 2.47 (4H, t, J=5.1 Hz), 1.40 (9H, s), 1.29 (6H, s). LC-MS: m/z=283 $[M+H]^+$.

Step C: tert-butyl 4-(5-(2-chloro-5-(methoxycarbonyl)-3-nitrophenoxy)-2-methylpent-3-yn-2-yl)piperazine-1-carboxylate The title compound was prepared in a similar fashion to Intermediate 12 (Step D) with methyl 4-chloro-3-hydroxy-5-nitrobenzoate and tert-butyl 4-(5-hydroxy-2-methylpent-3-yn-2-yl)piperazine-1-carboxylate. The crude product was purified by column chromatography on $SiO_2$ (Hexanes: EtOAc=3:1) to afford the title compound (quant.) as a colorless oil. LC-MS: m/z=496.1 $[M+H]^+$.

Step D: tert-butyl 4-(5-(5-carbamoyl-2-chloro-3-nitrophenoxy)-2-methylpent-3-yn-2-yl)piperazine-1-carboxylate The title compound was prepared in a similar fashion to Intermediate 12 (Step E) with tert-butyl 4-(5-(2-chloro-5-(methoxycarbonyl)-3-nitrophenoxy)-2-methylpent-3-yn-2-yl)piperazine-1-carboxylate. The crude product was purified by column chromatography on NH—$SiO_2$ (DCM: MeOH=95:5) to afford the title compound (30% for 2 steps) as a pale yellow solid. $^1$H NMR (400 MHz, DMSO-$d_6$): δ 8.24 (1H, s), 8.11 (1H, d, J=1.6 Hz), 8.03 (1H, d, J=2.0 Hz), 7.76 (1H, s), 5.13 (2H, s), 3.24 (4H, t, J=4.6 Hz), 2.35 (4H, s), 1.38 (9H, s), 1.25 (6H, s).

Intermediate 23: tert-butyl 4-(4-(5-carbamoyl-2-chloro-3-nitrophenoxy)but-2-yn-yl)piperidine-1-carboxylate

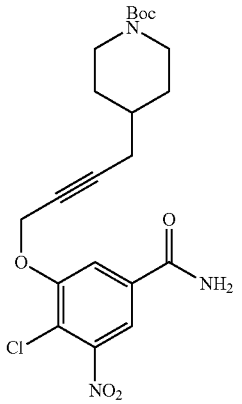 [SMILES: CC(C)(C)OC(=O)N1CCC(CC#CCOc2cc(C(N)=O)cc([N+](=O)[O-])c2Cl)CC1]

Step A: tert-butyl 4-(prop-2-yn-1-yl)piperidine-1-carboxylate

The title compound was prepared in a similar fashion to Intermediate 12 (Step B) with tert-butyl 4-(2-oxoethyl) piperidine-1-carboxylate and dimethyl (1-diazo-2 -oxopropyl)phosphonate. The crude product was purified by column chromatography on $SiO_2$ (pet.Ether:EtOAc=3:1) to give the title compound (98%) as a colorless oil. $^1$H NMR (400 MHz, DMSO-$d_6$): δ 3.93 (2H, d, J=13.1 Hz), 2.80 (1H, t, J=2.7 Hz), 2.68 (2H, s), 2.13 (2H, dd, J=6.6, 2.7 Hz), 1.71-1.63 (2H, m), 1.63-1.51 (1H, m), 1.39 (9H, s), 1.07 (2H, tdd, J=12.9, 11.5, 4.4 Hz).

Step B: tert-butyl 4-(4-hydroxybut-2-yn-1-yl)piperidine-1-carboxylate

The title compound was prepared in a similar fashion to Intermediate 12 (Step C) with tert-butyl 4-(prop-2-yn-1-yl) piperidine-1-carboxylate. The crude product was purified by column chromatography on $SiO_2$ (DCM:EtOAc=20:1) to give the title compound (73%) as a yellow oil. $^1$H NMR (400

MHz, DMSO-$d_6$): δ 5.03 (1H, t, J=5.9 Hz), 4.03 (2H, dt, J=5.9, 2.2 Hz), 3.93 (2H, d, J=13.1 Hz), 2.67 (2H, d, J=4.9 Hz), 2.15 (2H, dt, J=6.7, 2.2 Hz), 1.72-1.63 (2H, m), 1.55 (1H, dddd, J=13.9, 11.3, 6.7, 3.1 Hz), 1.41 (9H, s), 1.13-0.98 (2H, m).

Step C: tert-butyl 4-(4-(2-chloro-5-(methoxycarbonyl)-3-nitrophenoxy)but-2-yn-1-yl)piperidine-1-carboxylate The title compound was prepared in a similar fashion to Intermediate 12 (Step D) with tert-butyl 4-(4-hydroxybut-2-yn-1-yl)piperidine-1-carboxylate and methyl 4-chloro-3-hydroxy-5-nitrobenzoate. The crude product was purified by column chromatography on NH—$SiO_2$ (Hexanes: EtOAc=2:1 to 1:1) to give the title compound as a yellow oil. $^1$H NMR (400 MHz, CDCl3); δ 8.06 (1H, d, J=1.6 Hz), 7.93 (1H, d, J=1.6 Hz), 5.00-4.94 (1H, m), 4.90 (2H, t, J=2.0 Hz), 4.08 (2H, brs), 3.97 (3H, s), 2.67-2.60 (2H, m), 2.18-2.16 (2H, m), 1.70-1.67 (2H, m), 1.44 (9H, s), 1.14-1.04 (2H, m).

Step D: tert-butyl 4-(4-(5-carbamoyl-2-chloro-3-itrophenoxy)but-2-yn-yl)piperidine-1-carboxylate The title compound was prepared in a similar fashion to Intermediate 12 (Step E) with tert-butyl 4-(4-(2-chloro-5-(methoxycarbonyl)-3-nitrophenoxy)but-2-yn-1-yl)piperidine-1-carboxylate. The crude product was purified by column chromatography on NH—$SiO_2$ (DCM:EtOAc=7:3 to DCM:MeOH=20:1) to give the title compound (51% for 2 steps) as a pale yellow solid. $^1$H NMR (400 MHz, $CDCl_3$); $^1$H NMR (400 MHz, $CDCl_3$): δ 7.86 (1H, d, J= 1.6 Hz), 7.75 (1H, d, J=1.6 Hz), 5.00-4.94 (1H, m), 4.92 (2H, t, J=2.0 Hz), 4.05 (2H, brs), 2.67-2.60 (2H, m), 2.20-2.19 (2H, m), 1.65-1.61 (2H, m), 1.44 (9H, s), 1.14-1.04 (2H, m).

Intermediate 24: tert-butyl 3-(4-(5-carbamoyl-2-chloro-3-nitrophenoxy)but-2-yn-1-yl)azetidine-1-carboxylate

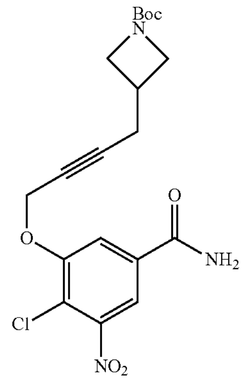 [SMILES: CC(C)(C)OC(=O)N1CC(CC#CCOc2cc(C(N)=O)cc([N+](=O)[O-])c2Cl)C1]

Step A: tert-butyl 3-(2-hydroxyethyl)azetidine-1-carboxylate

To a solution of tert-butyl 3-(2-methoxy-2-oxoethyl)azetidine-1-carboxylate (25.0 g, 109 mmol) in THF (250 mL) was added $LiBH_4$ (191 mL, 382 mmol) in portions at 0° C. The reaction mixture was stirred at room temperature overnight. After quenched with water, the mixture was extracted with EtOAc twice. The combined organic layers were washed with brine, dried over $Na_2SO_4$, filtered, and concentrated in vacuo to afford the title compound (20.0 g, 91%) as a colorless oil. $^1$H NMR (400 MHz, $CDCl_3$): δ 4.02 (2H, q, J=8.6 Hz), 3.76 (1H, dt, J=19.7, 6.2 Hz), 3.64-3.57 (3H, m), 2.71-2.56 (1H, m), 1.88-1.80 (2H, m), 1.43 (9H, s). LC-MS: m/z=202 $[M+H]^+$.

Step B: tert-butyl 3-(2-oxoethyl)azetidine-1-carboxylate

A mixture of tert-butyl 3-(2-hydroxyethyl)azetidine-1-carboxylate (20.0 g, 99.4 mmol) and Dess-Martin periodinane (84.3 g, 199 mmol) in DCM (200 mL) was stirred at room temperature for 2 hours. After addition of saturated aq. $NaHCO_3$ solution, the mixture was filtered, and the filtered cake was washed with DCM. The filtrate was concentrated in vacuo. The residue was purified by column chromatography on $SiO_2$ (pet.Ether:EtOAc=3:1) to afford the title compound (10.0 g, 50%) as a yellow oil. $^1$H NMR (400 MHz, $CDCl_3$): δ 9.77 (1H, d, J=0.9 Hz), 3.74-3.42 (4H, m), 2.85-2.77 (2H, m), 2.07 (1H, s), 1.43 (9H, s). LC-MS: m/z=200 $[M+H]^+$.

Step C: tert-butyl 3-(prop-2-yn-1-yl)azetidine-1-carboxylate

The title compound was prepared in a similar fashion to Intermediate 12 (Step B) with tert-butyl 3-(2-oxoethyl)azetidine-1-carboxylate and dimethyl (1-diazo-2-oxopropyl)phosphonate. The crude product was purified by column chromatography on $SiO_2$ (pet.Ether:EtOAc=19:1) to afford the title compound (60%) as a yellow oil. $^1$H NMR (400 MHz, $CDCl_3$): δ 4.06-3.97 (2H, m), 3.69 (2H, dd, J=8.8, 5.3 Hz), 2.44 (2H, dd, J=6.9, 2.7 Hz), 1.98 (1H, t, J=2.6 Hz), 1.44 (9H, s). LC-MS: m/z=196 $[M+H]^+$.

Step D: tert-butyl 3-(4-hydroxybut-2-yn-1-yl)azetidine-1-carboxylate

The title compound was prepared in a similar fashion to Intermediate 12 (Step C) with tert-butyl 3-(prop-2-yn-1-yl)azetidine-1-carboxylate. The crude product was purified by column chromatography on $SiO_2$ (pet.Ether:EtOAc=7:3) to afford the title compound (31%) as a yellow oil. $^1$H NMR (400 MHz, $CDCl_3$): δ 4.24 (2H, t, J=2.1 Hz), 4.02 (2H, t, J=8.4 Hz), 3.68 (2H, dd, J=8.8, 5.2 Hz), 2.74-2.63 (1H, m), 2.47 (2H, dt, J=6.8, 2.2 Hz), 1.44 (9H, s). LC-MS: m/z=226 $[M+H]^+$.

Step E: tert-butyl 3-(4-(2-chloro-5-(methoxycarbonyl)-3-nitrophenoxy)but-2-yn-1-yl)azetidine-1-carboxylate The title compound was prepared in a similar fashion to Intermediate 12 (Step D) with methyl 4-chloro-3-hydroxy-5-nitrobenzoate and tert-butyl 3-(4-hydroxybut-2-yn-1-yl)azetidine-1-carboxylate. The crude product was purified by column chromatography on $SiO_2$ (Hexanes:EtOAc=3:1) to afford the title compound (crude) as a colorless oil. LC-MS: m/z=339.0 $[M-99]^+$.

Step F: tert-butyl 3-(4-(5-carbamoyl-2-chloro-3-nitrophenoxy)but-2-yn-1-yl)azetidine-1-carboxylate The title compound was prepared in a similar fashion to Intermediate 12 (Step E) with tert-butyl 3-(4-(2-chloro-5-

(methoxycarbonyl)-3-nitrophenoxy)but-2-yn-1-yl)azetidine-1 -carboxylate. The crude product was purified by column chromatography on $SiO_2$ (DCM only to DCM: MeOH=9:1) to afford the title compound (26% for 2 steps) as a yellow oil. $^1$H NMR (400 MHz, DMSO-$d_6$): □□ 8.25 (1H, s), 8.11 (1H, d, J=1.6 Hz), 7.97 (1H, d, J=1.6 Hz), 7.78 (1H, s), 5.08 (2H, s), 3.83 (2H, t, J=8.4 Hz), 3.46 (2H, t, J=6.6 Hz), 2.67-2.60 (1H, m), 2.52 (2H, s), 1.33 (9H, s). LC-MS: m/z=324.0 $[M-99]^+$.

Intermediate 25: tert-butyl 3-(4-(5-carbamoyl-2-chloro-3-nitrophenoxy)but-2-yn-1-yl)pyrrolidine-1-carboxylate

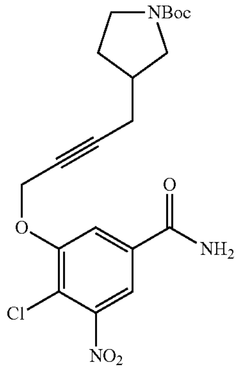 [SMILES: CC(C)(C)OC(=O)N1CCC(CC#CCOc2cc(C(N)=O)cc([N+](=O)[O-])c2Cl)C1]

Step A: tert-butyl 3-[(E)-2-methoxyethenyl]pyrrolidine-1-carboxylate

To a mixture of KO$^t$-Bu (20.3 g, 181 mmol) in THF (180 mL) was added (methoxymethyl)triphenyl-lambda5-phosphane chloride (62.1 g, 181 mmol) at room temperature. The mixture was stirred at room temperature for 30 min. After addition of tert-butyl 3-formylpyrrolidine-1-carboxylate (18.0 g, 90.3 mmol) in portions at room temperature, the reaction mixture was stirred at room temperature overnight. After quenched with water, the mixture was extracted with EtOAc twice. The combined organic layers were washed with brine, dried over $Na_2SO_4$, filtered, and concentrated in vacuo. The residue was purified by column chromatography on $SiO_2$ (pet.Ether:EtOAc=3:1) to afford the title compound (6.30 g, 31%) as a yellow liquid. $^1$H NMR (400 MHz, $CDCl_3$): δ 6.38 (1H, d, J=12.6 Hz), 4.64 (1H, dd, J=12.7, 8.5 Hz), 3.60 (1H, s), 3.52 (2H, s), 3.27 (1H, s), 2.93 (1H, s), 2.68 (1H, d, J=8.3 Hz), 1.98 (1H, dddq, J=15.5, 9.4, 6.6, 2.9 Hz), 1.46 (9H, d, J=1.7 Hz). LC-MS: m/z=228 $[M+H]^+$.

Step B: tert-butyl 3-(2-oxoethyl)pyrrolidine-1-carboxylate

A mixture of tert-butyl 3-[(E)-2-methoxyethenyl]pyrrolidine-1-carboxylate (7.10 g, 31.2 mmol) and formic acid (28 mL) was stirred at room temperature for 40 min. After neutralization with saturated aq. $NaHCO_3$ solution, the mixture was extracted with EtOAc twice. The combined organic layers were washed with brine, dried over $Na_2SO_4$, filtered, and concentrated in vacuo to afford the title compound (5.00 g, 75%) as a yellow oil. $^1$H NMR (400 MHz, $CDCl_3$): δ 9.79 (1H t, J=1.3 Hz), 3.63 (1H, dd, J=10.8, 7.0 Hz), 3.45 (1H, ddd, J=11.5, 8.2, 3.8 Hz), 3.34-3.26 (1H, m), 2.92 (1H, dd, J=10.8, 7.6 Hz), 2.68-2.51 (3H, m), 2.10 (1H, dtd, J=10.2, 6.6, 3.8 Hz), 1.61-1.49 (1H, m), 1.46 (9H, s). LC-MS: m/z=214 $[M+H]^+$.

Step C: tert-butyl 3-(prop-2-yn-1-yl)pyrrolidine-1-carboxylate

The title compound was prepared in a similar fashion to Intermediate 12 (Step B) with tert-butyl 3-(2-hydroxyethyl) pyrrolidine-1-carboxylate and dimethyl (1-diazo-2-oxopropyl)phosphonate. The crude product was used for the next reaction without purification as a yellow oil. $^1$H NMR (400 MHz, $CDCl_3$): δ 3.47 (1H, dd, J=10.9, 7.1 Hz), 3.39 (1H, ddd, J=15.1, 7.4, 3.4 Hz), 3.24 (1H, dt, J=10.9, 7.7 Hz), 2.99 (1H, dd, J=10.8, 7.4 Hz), 2.30 (1H, dt, J=14.2, 7.1 Hz), 2.21 (2H, dt, J=6.9, 2.5 Hz), 2.00-1.90 (2H, m), 1.68-1.59 (1H, m), 1.39 (9H, d, J=0.9 Hz). LC-MS: m/z=210 $[M+H]^+$.

Step D: tert-butyl 3-(4-hydroxybut-2-yn-1-yl)pyrrolidine-1-carboxylate

The title compound was prepared in a similar fashion to Intermediate 12 (Step C) with tert-butyl 3-(prop-2-yn-1-yl) pyrrolidine-1-carboxylate. The crude product was purified by column chromatography on $SiO_2$ (pet.Ether:EtOAc=7:3) to afford title compound (50% for 2 steps) as a yellow oil. $^1$H NMR (400 MHz, $CDCl_3$): δ 4.25 (2H, t, J=2.0 Hz), 3.56-3.41 (2H, m), 3.30 (1H, dt, J=10.9, 7.8 Hz), 3.07 (1H, dd, J=10.8, 6.8 Hz), 2.43-2.30 (2H, m), 2.34-2.27 (1H, m), 2.07-1.95 (2H, m), 1.69 (1H, dq, J=12.7, 8.0 Hz), 1.46 (9H, s). LC-MS: m/z=240 $[M+H]^+$.

Step E: tert-butyl 3-(4-(2-chloro-5-(methoxycarbonyl)-3-nitrophenoxy)but-2-yn-1-yl)pyrrolidine-1-carboxylate The title compound was prepared in a similar fashion to Intermediate 12 (Step D) with methyl 4-chloro-3-hydroxy-5-nitrobenzoate and tert-butyl 3-(4-hydroxybut-2-yn-1 -yl) pyrrolidine-1-carboxylate. The crude product was purified by column chromatography on $SiO_2$ (Hexanes:EtOAc=3:1) to afford the title compound (quant.) as a colorless oil. $^1$H NMR (400 MHz, DMSO-$d_6$): δ 8.13 (1H, d, J=1.6 Hz), 7.99 (1H, d, J=2.0 Hz), 5.16 (2H, s), 3.91 (3H, s), 3.26-3.23 (1H, m), 3.17-3.09 (1H, m), 2.81 (1H, dd, J=10.6, 8.2 Hz), 2.36 (2H, d, J=6.0 Hz), 2.29-2.20 (1H, m), 1.91-1.82 (1H, m), 1.57-1.47 (1H, m), 1.36 (9H, d, J=7.6 Hz).

Step F: tert-butyl 3-(4-(5-carbamoyl-2-chloro-3-nitrophenoxy)but-2-yn-1-yl)pyrrolidine-1-carboxylate The title compound was prepared in a similar fashion to Intermediate 12 (Step E) with tert-butyl 3-(4-(2-chloro-5-(methoxycarbonyl)-3-nitrophenoxy)but-2-yn-1-yl)pyrrolidine-1-carboxylate. The crude product was purified by column chromatography on NH—$SiO_2$ (DCM:MeOH=95:5) to afford the title compound (73%) as a pale yellow solid. $^1$H NMR (400 MHz, DMSO-$d_6$): δ 8.24 (1H, s), 8.11 (1H, s), 7.99 (1H, s), 7.78 (1H, s), 5.09 (2H, s), 3.36-3.33 (1H, m), 3.30-3.25 (1H, m), 3.17-3.09 (1H, m), 2.83 (1H, dd, J=10.6, 7.8 Hz), 2.36 (2H, d, J=6.4 Hz), 2.28-2.24 (1H, m), 1.88-1.86 (1H, m), 1.56-1.49 (1H, m), 1.37 (9H, d, J=6.4 Hz).

Intermediate 26: tert-butyl 3-(4-(5-carbamoyl-2-chloro-3-nitrophenoxy)but-2-yn-1-yl)piperidine-1-carboxylate

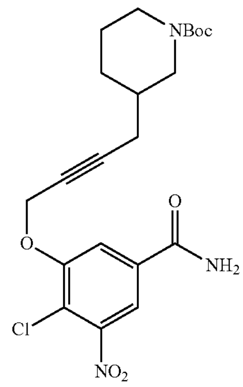 [SMILES: CC(C)(C)OC(=O)N1CCCC(CC#CCOc2cc(C(N)=O)cc([N+](=O)[O-])c2Cl)C1]

Step A: tert-butyl 3-[(E)-2-methoxyethenyl]piperidine-1-carboxylate

The title compound was prepared in a similar fashion to Intermediate 25 (Step A) with tert-butyl 3-formylpiperidine-1-carboxylate and (methoxymethyl)triphenyl-lambda5-phosphane chloride. The crude product was purified by column chromatography on $SiO_2$ (pet.Ether:EtOAc=9:1) to afford title compound (63%) as a yellow oil. LC-MS: m/z=242 $[M+H]^+$.

Step B: tert-butyl 3-(2-oxoethyl)piperidine-1-carboxylate

The title compound was prepared in a similar fashion to Intermediate 25 (Step B) with tert-butyl 3-[(E)-2-methoxyethenyl]piperidine-1-carboxylate. The crude product was used for the next reaction without purification as a yellow oil. $^1H$ NMR (400 MHz, $CDCl_3$): δ 9.78 (1H, t, J=1.9 Hz), 3.91-3.78 (2H, m), 2.89 (1H, ddd, J=13.5, 10.6, 3.3 Hz), 2.67 (1H, t, J=11.3 Hz), 2.41 (1H, ddd, J=16.9, 6.6, 1.7 Hz), 2.30 (1H, ddd, J=16.9, 7.1, 2.1 Hz), 2.10 (1H, ttt, J=10.4, 7.0, 3.8 Hz), 1.85 (1H ddt, J=13.2, 5.3, 3.8 Hz), 1.64 (1H, dq, J=12.9, 4.1 Hz), 1.55-1.48 (1H, m), 1.46 (9H, s), 1.20 (1H, dtd, J=14.0, 10.4, 4.0 Hz). LC-MS: m/z=228 $[M+H]^+$.

Step C: tert-butyl 3-(prop-2-yn-1-yl)piperidine-1-carboxylate

The title compound was prepared in a similar fashion to Intermediate 12 (Step B) with tert-butyl 3-(2-oxoethyl) piperidine-1-carboxylate and dimethyl (1-diazo-2-oxopropyl)phosphonate. The crude product was used for the next reaction without purification as a yellow oil. $^1H$ NMR (400 MHz, $CDCl_3$): δ 4.05-3.98 (1H, m), 3.89 (1H, dtt, J=13.2, 4.1, 1.4 Hz), 2.79 (1H, ddd, J=13.2, 11.2, 3.2 Hz), 2.61 (1H, dd, J=13.1, 10.1 Hz), 2.17-2.11 (2H, m), 1.99 (1H, t, J=2.7 Hz), 1.88 (1H, dt, J=13.1, 3.9 Hz), 1.68 (3H, dddt, J=18.0, 14.2, 8.1, 4.1 Hz), 1.46 (9H, s), 1.25 (1H, dddd, J=14.8, 13.1, 8.5, 3.3 Hz). LC-MS: m/z=224 $[M+H]^+$.

Step D: tert-butyl 3-(4-hydroxybut-2-yn-1-yl)piperidine-1-carboxylate

The title compound was prepared in a similar fashion to Intermediate 12 (Step C) with tert-butyl 3-(prop-2-yn-1-yl) piperidine-1-carboxylate. The crude product was purified by column chromatography on $SiO_2$ (pet.Ether:EtOAc=4:1) to afford title compound (16% for 3 steps) as a yellow oil. $^1H$ NMR (400 MHz, $CDCl_3$): δ 4.25 (2H, t, J=2.2 Hz), 4.05-3.96 (1H, m), 3.93-3.78 (1H, m), 2.79 (1H, ddd, J=13.1, 11.1, 3.2 Hz), 2.60 (1H, dd, J=13.1, 10.1 Hz), 2.17 (2H, dt, J=6.8, 2.2 Hz), 1.87 (2H, d, J=17.3 Hz), 1.66 (2H, dtt, J=15.0, 7.5, 3.7 Hz), 1.46 (9H, s), 1.43-1.32 (1H, m), 1.32-1.15 (1H, m), 0.92 (1H, dt, J=14.2, 7.2 Hz). LC-MS: m/z=254 $[M+H]^+$.

Step E: tert-butyl 3-(4-(2-chloro-5-(methoxycarbonyl)-3-nitrophenoxy)but-2-yn-1-yl)piperidine-1-carboxylate The title compound was prepared in a similar fashion to Intermediate 12 (Step D) with tert-butyl 3-(4-hydroxybut-2-yn-1-yl)piperidine-1-carboxylate and methyl 4-chloro-3-hydroxy-5-nitrobenzoate. The crude product was purified by column chromatography on NH—$SiO_2$ (Hexanes:EtOAc=3:1) to afford the title compound as a colorless oil. $^1H$ NMR (400 MHz, DMSO-$d_6$): □□ 8.13 (1H, d, J=1.6 Hz), 7.99 (1H, d, J=2.0 Hz), 5.14 (2H, s), 3.90 (3H, s), 3.73-3.70 (2H, m), 2.62 (1H, s), 2.19 (2H, d, J=5.2 Hz), 1.69 (1H, d, J=12.8 Hz), 1.52-1.48 (2H, m), 1.38 (1H, s), 1.35 (9H, s). LC-MS: m/z=367.1 $[M-99]^+$.

Step F: tert-butyl 3-(4-(5-carbamoyl-2-chloro-3-nitrophenoxy)but-2-yn-1-yl)piperidine-1-carboxylate The title compound was prepared in a similar fashion to Intermediate 12 (Step E) with tert-butyl 3-(4-(2-chloro-5-(methoxycarbonyl)-3-nitrophenoxy)but-2-yn-1-yl)piperidine-1-carboxylate. The crude product was purified by column chromatography on $SiO_2$ (DCM only to DCM:MeOH=9:1) to afford the title compound (34% for 2 steps) as a yellow foam. $^1H$ NMR (400 MHz, DMSO-$d_6$): □□ 8.24 (1H, s), 8.10 (1H, d, J=2.0 Hz), 7.99 (1H, d, J=1.2 Hz), 7.78 (1H, s), 5.10 (2H, s), 3.80-3.73 (2H, m), 2.68-2.63 (1H, m), 2.21-2.18 (2H, m), 1.71-1.68 (1H, m), 1.54-1.46 (2H, m), 1.38 (9H, s), 1.27-1.24 (1H, m). LC-MS: m/z=352.0 $[M-99]^+$.

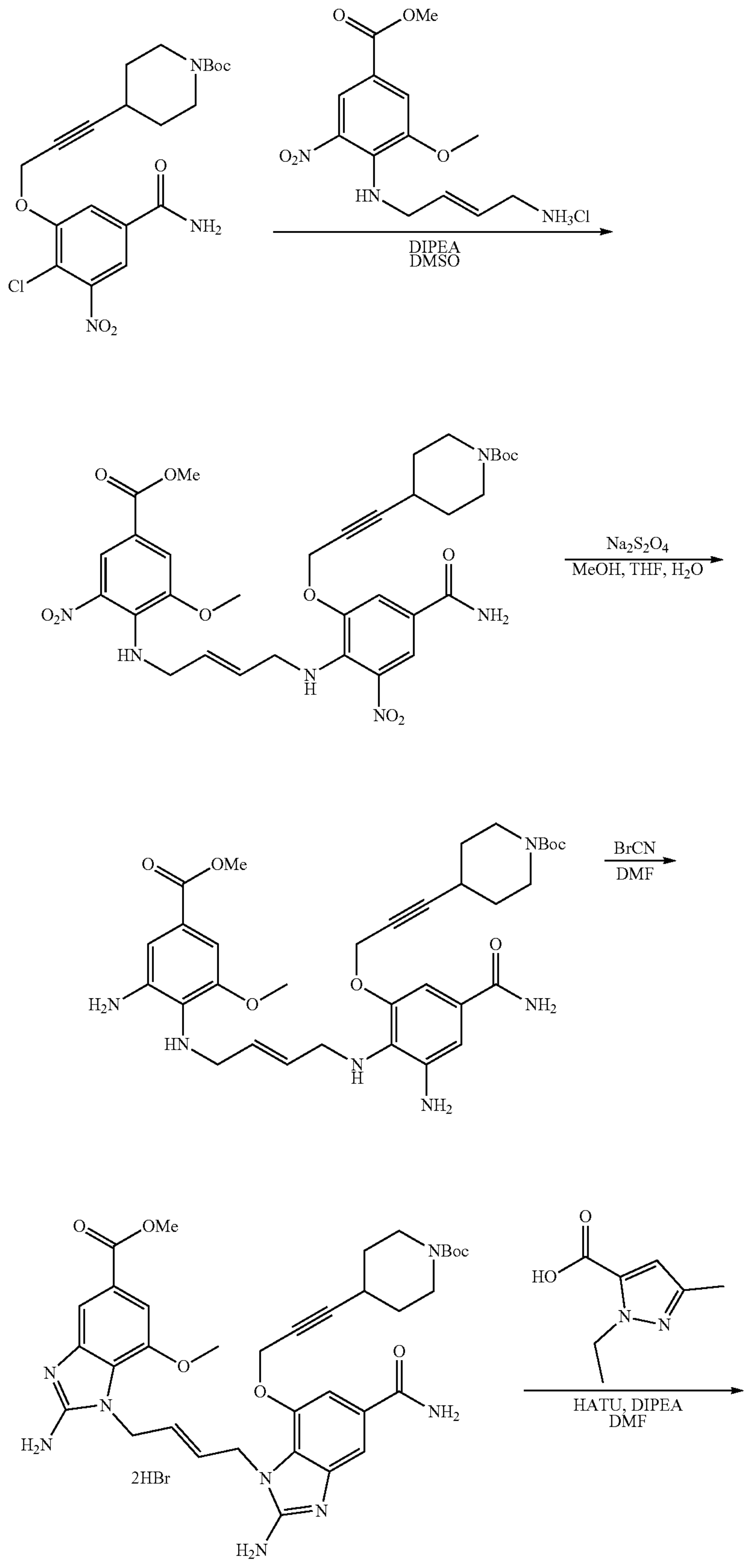
DIPEA
DMSO
$Na_2S_2O_4$
MeOH, THF, $H_2O$
BrCN
DMF
HATU, DIPEA
DMF

-continued
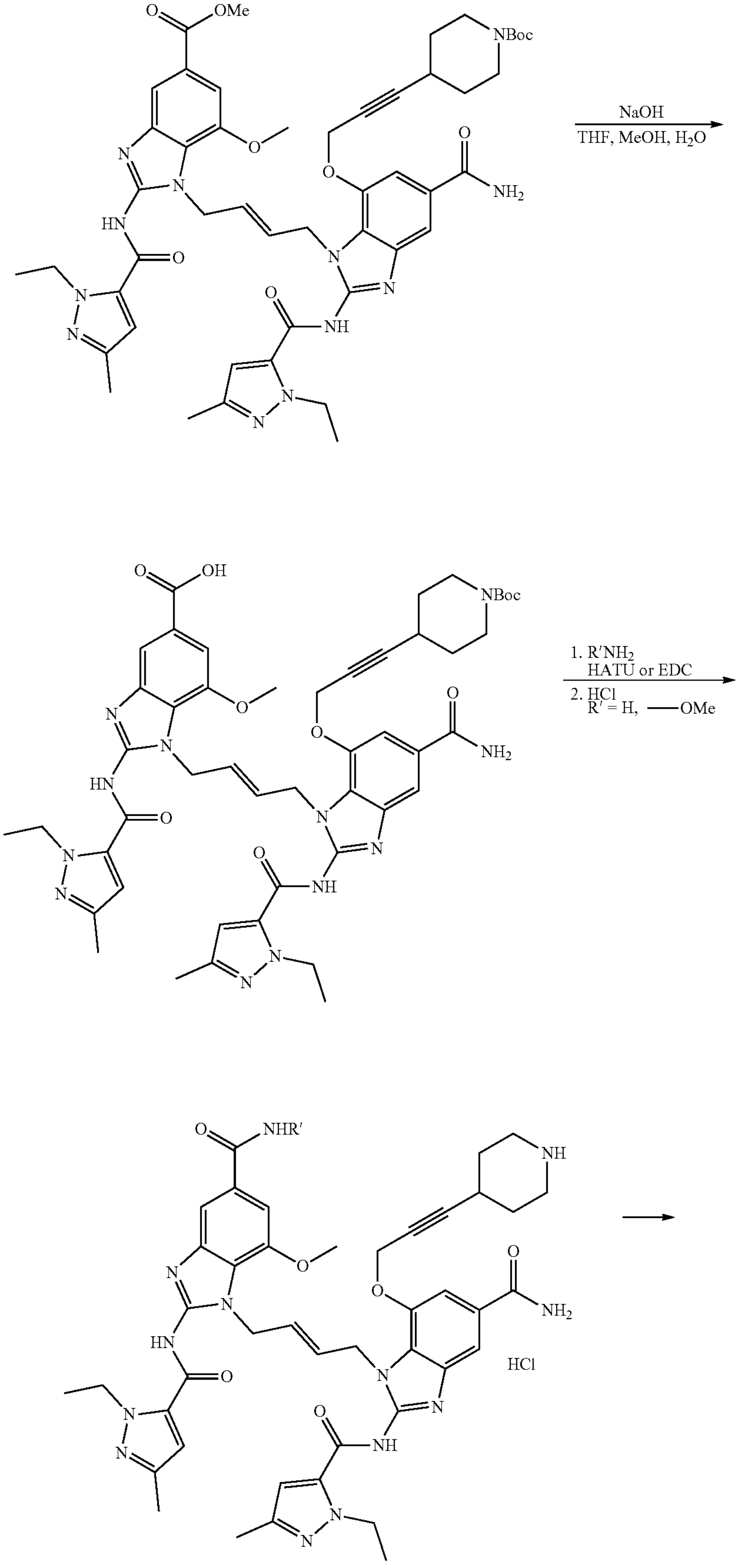

-continued

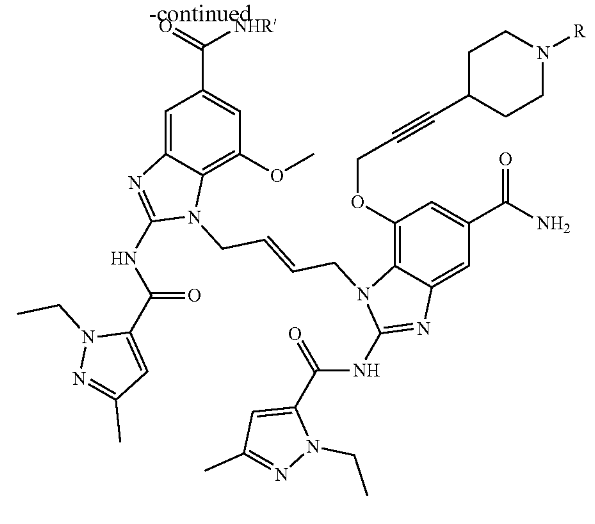

R = $CONR_1R_2$, $CO_2R$, COR, $SO_2R$, $SO_2NR_1R_2$ etc

Example 1: (E)-1-(4-(7-((3-(1-(tert-butoxycarbonyl)piperidin-4-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid

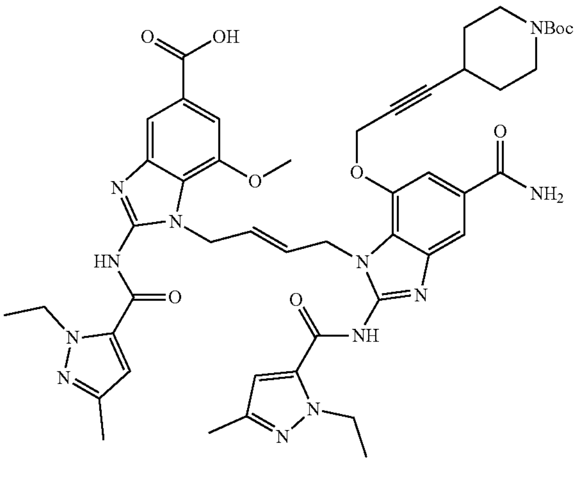 [SMILES: CCn1nc(C)cc1C(=O)Nc1nc2cc(C(=O)O)cc(OC)c2n1C/C=C/Cn1c(NC(=O)c2cc(C)nn2CC)nc2cc(C(N)=O)cc(OCC#CC3CCN(C(=O)OC(C)(C)C)CC3)c21]

Step A: tert-butyl (E)-4-(3-(5-carbamoyl-2-((4-((2-methoxy-4-(methoxycarbonyl)- 6-nitrophenyl)amino)but-2-en-1-yl)amino)-3-nitrophenoxy)prop-1-yn-1-yl)piperidine-1-carboxylate To a solution of tert-butyl 4-(3-(5-carbamoyl-2-chloro-3-nitrophenoxy)prop-1-yn-1-yl)piperidine-1-carboxylate (Intermediate 15, 0.388 g, 0.886 mmol) in DMSO (4.4 mL) was added DIPEA (0.774 mL, 4.43 mmol) and methyl (E)-4-((4-aminobut-2-en-1-yl)amino)-3-methoxy-5-nitrobenzoate hydrochloride (Intermediate 1, 0.588 g, 1.77 mmol). The reaction mixture was stirred at 120° C. for 3 hours. After quenched with saturated aq. $NaHCO_3$ solution, the mixture was extracted with DCM twice. The combined organic layers were washed with brine, dried over $Na_2SO_4$, filtered, and concentrated in vacuo. The residue was purified by column chromatography on NH—$SiO_2$ (DCM only to DCM:MeOH=98:2) to give the title compound (0.265 g, 43%) as an orange solid. $^1H$ NMR (400 MHz, DMSO-$d_6$): δ 8.19 (1H, d, J=2.0 Hz), 8.10 (1H, d, J=1.6 Hz), 7.96 (2H, m), 7.77 (1H, t, J=6.4 Hz), 7.61 (1H, d, J=2.0 Hz), 7.35 (1H, d, J=1.6 Hz), 7.30 (1H, brs), 5.59 (2H, t, J=4.4 Hz), 4.78 (2H, d, J=1.6 Hz), 4.10 (4H, m), 3.83 (3H, s), 3.80 (3H, s), 3.47-3.42 (2H, m), 3.07 (2H, t, J=9.6 Hz), 2.66 (1H, m), 1.68-1.63 (2H, m), 1.38-1.37 (11H, m).

Step B: tert-butyl (E)-4-(3-(3-amino-2-((4-((2-amino-6-methoxy-4-(methoxycarbonyl)phenyl)-amino)but-2-en-1-yl)amino)-5-carbamoylphenoxy)prop-1-yn-1-yl)piperidine-1-carboxylate To a solution of tert-butyl (E)-4-(3-(5-carbamoyl-2-((4-((2-methoxy-4-(methoxycarbonyl)-6-nitro-phenyl)amino)but-2-en-1-yl)amino)-3-nitrophenoxy)prop-1-yn-1-yl)piperidine-1-carboxylate (0.265 g, 0.380 mmol) in a mixture of MeOH (7.5 mL) and THF (5.8 mL) was added a solution of sodium hydrosulfite (0.927 g, 5.32 mmol) in water (5.8 mL) at 0° C. The reaction mixture was stirred at room temperature for 1 hour. After quenched with saturated aq. $NaHCO_3$ solution, the mixture was extracted with DCM twice. The combined organic layers were dried over $Na_2SO_4$, filtered, and concentrated in vacuo to give the title compound (0.195 g, 81%) as a light brown solid. LC-MS: m/z=637.2 $[M+H]^+$.

Step C: methyl (E)-2-amino-1-(4-(2-amino-7-((3-(1-(tert-butoxycarbonyl)piperidin-4-yl)prop-2-yn-1-yl)oxy)-5-carbamoyl-1H-benzo[d]imidazol-1-yl)but-2-en-1-yl)-7-methoxy-1H-benzo[d]imidazole-5-carboxylate dihydrobromide To a solution of tert-butyl (E)-4-(3-(3-amino-2-((4-((2-amino-6-methoxy-4-(methoxycarbonyl)-phenyl)amino)but-2-en-1-yl)amino)-5-carbamoylphenoxy)prop-1-yn-1-yl)piperidine-1-carboxylate (0.195 g, 0.306 mmol) in DMF (2.5 mL) was added cyanic bromide (81.0 mg, 0.766 mmol) at room temperature. The reaction mixture was stirred at room temperature overnight and then heated at 70° C. for 1 hour. After concentration in vacuo, the residue was purified by recrystallization from $Et_2O$/MeOH. The solid was collected by filtration, washed with $Et_2O$, and dried under vacuum to afford the title compound (0.230 g, 89%) as a yellow solid. LC-MS: m/z=687.2 $[M+H]^+$.

Step D: methyl (E)-1-(4-(7-((3-(1-(tert-butoxycarbonyl)piperidin-4-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate To a solution of methyl (E)-2-(bromo-15-azanyl)-1-(4-(2-(bromo-15-azanyl)-7-((3-(1-(tert-butoxycarbonyl)piperidin-4-yl)prop-2-yn-1-yl)oxy)-5-carbamoyl-1H-benzo[d]imidazol-1-yl)but-2-en-1-yl)-7-methoxy-1H-benzo[d]imidazole-5-carboxylate (0.230 g, 0.271 mmol) and 1-ethyl-3-methyl-1H-pyrazole-5-carboxylic acid (92.0 mg, 0.596 mmol) in DMF (2.7 mL) was added HATU (0.227 g, 0.596 mmol) and DIPEA (0.284 mL, 1.63 mmol) at room temperature. The reaction mixture was stirred at 80° C. overnight. After concentration in vacuo, the residue was dissolved in DCM and washed with saturated aq. $NaHCO_3$ solution. The separated organic layer was dried over $Na_2SO_4$, filtered, and concentrated in vacuo. The residue was purified by column chromatography on $SiO_2$ (DCM:MeOH:$NH_4OH$=95:5:0.1) to give the title compound (0.102 g, 28% for 3 steps) as a light brown solid. $^1H$ NMR (400 MHz, DMSO-$d_6$): δ 8.19 (1H, d, J=2.0 Hz), 8.10 (1H, d, J=1.6 Hz), 7.96 (2H, m), 7.77 (1H, t, J=6.4 Hz), 7.61 (1H, d, J=2.0 Hz), 7.35 (1H, d, J=1.6 Hz), 7.30 (1H, brs), 5.59 (2H, t, J=4.4 Hz), 4.78 (2H, d, J=1.6 Hz), 4.10 (4H, m), 3.83 (3H, s), 3.80 (3H, s), 3.47-3.42 (2H, m), 3.07 (2H, t, J=9.6 Hz), 2.66 (1H, m), 1.68-1.63 (2H, m), 1.38-1.37 (11H, m).

Step E: (E)-1-(4-(7-((3-(1-(tert-butoxycarbonyl)piperidin-4-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[ d]imidazole-5-carboxylic acid To a solution of methyl (E)-1-(4-(7-((3-(1-(tert-butoxycarbonyl)piperidin-4-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate (45.0 mg, 0.0470 mmol) in a mixture of MeOH (0.30 mL) and THF (0.30 mL) and water (0.30 mL) was added NaOH (28.0 mg, 0.704 mmol) at room temperature. The reaction mixture was stirred at 60° C. for 2 hours and cooled to room temperature. After concentration in vacuo, the residue was acidified with citric acid until pH 2. A precipitated solid was collected by filtration, washed with water, and dried under vacuum to afford the title compound (38.0 mg, 86%) as a light brown solid. $^1H$ NMR (400 MHz, DMSO-$d_6$): δ 7.89 (1H, s), 7.76 (1H, s), 7.66 (1H, s), 7.37 (2H, s), 7.27 (1H, s), 6.53 (1H, s), 6.51 (1H, s), 5.90-5.87 (2H, m), 4.91 (s, 4H), 4.68 (s, 2H), 4.53 (4H, d, J=6.8 Hz), 3.65 (3H, s), 3.45-3.42 (2H, m), 2.93-2.90 (2H, m), 2.15-2.13 (1H, m), 2.10 and 2.08 (6H, s+s), 1.54 (2H, brs), 1.34 (9H, s), 1.29-1.22 (8H, m).

Example 2: tert-butyl (E)-4-(3-((5-carbamoyl-2-(1-ethyl-3-methyl-1H-pyrazole-5-carboxamido)-1-(4-(2-(1-ethyl-3-methyl-1H-pyrazole-5-carboxamido)-7-methoxy-5-(methoxycarbamoyl)-1H-benzo[d]imidazol-1-yl)but-2-en-1-yl)-1H-benzo[d]imidazol-7-yl)oxy)prop-1-yn-1-yl)piperidine-1-carboxylate

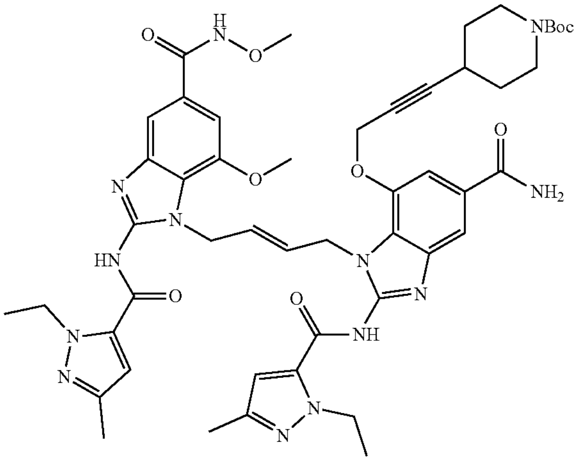 [SMILES: CCn1nc(C)cc1C(=O)Nc1nc2cc(C(=O)NOC)cc(OC)c2n1C/C=C/Cn1c(NC(=O)c2cc(C)nn2CC)nc2cc(C(N)=O)cc(OCC#CC3CCN(C(=O)OC(C)(C)C)CC3)c21]

To a solution of (E)-1-(4-(7-((3-(1-(tert-butoxycarbonyl)piperidin-4-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid (Example 1, 38.0 mg, 0.0400 mmol) in DMF (2.0 mL) was successively added o-methylhydroxylamine hydrochloride (17.0 mg, 0.201 mmol), EDC (39.0 mg, 0.201 mmol), HOBT (6.16 mg, 0.0400 mmol) and DIPEA (0.0350 mL, 0.201 mmol) at room temperature The reaction mixture was stirred at room temperature overnight. After dilution with a mixture of DCM/MeOH, the mixture was washed with water followed by brine, dried over $Na_2SO_4$, filtered, and concentrated in vacuo. The residue was purified by column chromatography on $SiO_2$ (DCM:MeOH:$NH_4OH$=93:7:0.1 to 90:10:0.1) followed by recrystallization from Hexanes/acetone to give the title compound (10.0 mg, 26%) as light brown solid. $^1H$ NMR (400 MHz, DMSO-$d_6$): δ 11.74 (1H, s), 7.90 (1H, s), 7.66 (1H, s), 7.57 (1H, s), 7.38 (1H, s), 7.35 (1H, s), 7.11 (1H, s), 6.53 (2H, s), 5.94-5.82 (2H, m), 4.91 (4H, s), 4.65 (2H, s), 4.53 (4H, d, J=6.4 Hz), 3.73 (3H, s), 3.63 (3H, s), 3.50-3.42 (2H, m), 2.93-2.84 (2H, m), 2.44 (1H, s), 2.11 (6H, d, J=3.6 Hz), 1.60-1.51 (2H, m), 1.34 (11H, s), 1.30-1.23 (6H, m). LC-MS: m/z=974.3 $[M+H]^+$.

Example 3: tert-butyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy) prop-1-yn-1-yl)piperidine-1-carboxylate

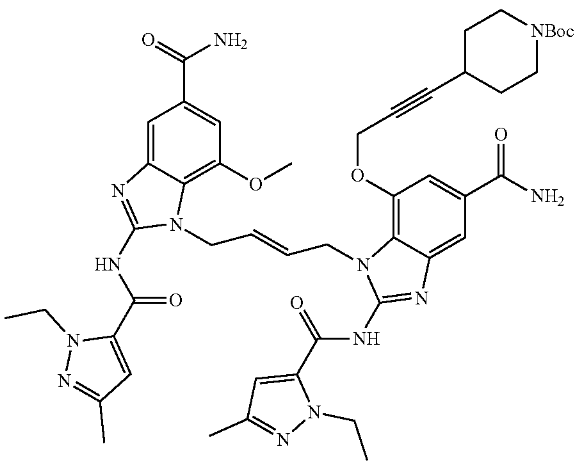 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)OC(C)(C)C)CC3)c21]

A mixture of (E)-1-(4-(7-((3-(1-(tert-butoxycarbonyl)piperidin-4-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid (Example 1, 20.0 mg, 0.0210 mmol), $NH_4Cl$ (11.3 mg, 0.212 mmol), HATU (12.1 mg, 0.0320 mmol) and DIPEA (0.0110 mL, 0.0630 mmol) in DMF (1.0 mL) was stirred at 120° C. for 2 hours. After concentration in vacuo, the residue was purified by column chromatography on NH—$SiO_2$ (DCM:MeOH=93:7) to afford the title compound (12.4 mg, 62%) as a white solid. $^1$H NMR (400 MHz, DMSO-$d_6$): δ 7.98 (1H, s), 7.91 (1H, s), 7.65 (2H, d, J=3.6 Hz), 7.36 (3H, s), 7.28 (1H, s), 6.54 (1H, s), 6.52 (1H, s), 5.94-5.82 (2H, m), 4.91 (4H, s), 4.67 (2H, s), 4.54-4.52 (4H, m), 3.66 (3H, s), 3.46-3.42 (2H, m), 2.44 (1H, s), 2.10 (6H, d, J=4.4 Hz), 1.57-1.54 (2H, m), 1.34 (9H, s), 1.29-1.24 (10H, m). LC-MS: m/z=944.3 $[M+H]^+$.

Example 4: (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride

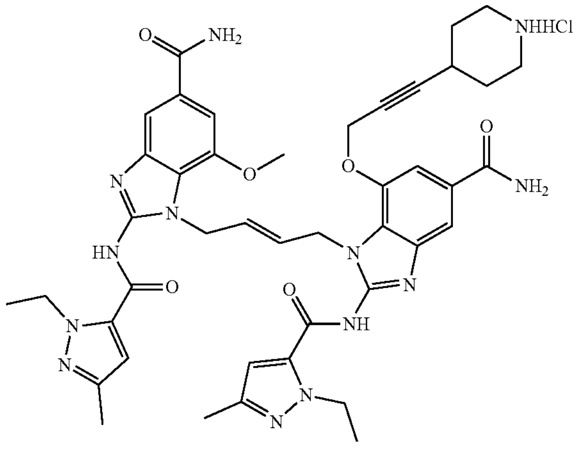

To a solution of tert-butyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate (Example 3, 47.0 mg, 0.0500 mmol) in DCM (2.5 mL) was added HCl (4M HCl in dioxane, 0.622 mL, 2.49 mmol) at room temperature. The reaction mixture was stirred at room temperature for 1 hour. After concentration in vacuo, a residual solid was purified by recrystallization from $Et_2O$/MeOH. The solid was collected by filtration, washed with $Et_2O$ dried under vacuum to afford the title compound (32.0 mg, 73%) as a white solid. $^1$H NMR (400 MHz, DMSO-$d_6$): δ 8.69 (1H, s), 8.58 (1H, s), 8.02 (1H, s), 7.96 (1H, s), 7.67 (1H, d, J=0.8 Hz), 7.65 (1H, d, J=0.8 Hz), 7.40 (1H, d, J=1.6 Hz), 7.38 (2H, s), 7.31 (1H, d, J=1.2 Hz), 6.55 (1H, s), 6.54 (1H, s), 5.93-5.79 (2H, m), 4.91 (4H, d, J=4.8 Hz), 4.73 (2H, s), 4.53 (4H, q, J=7.1 Hz), 3.69 (3H, s), 3.05-3.03 (2H, m), 2.84-2.77 (2H, m), 2.65-2.58 (1H, m), 2.11 (6H, d, J=1.6 Hz), 1.83-1.78 (2H, m), 1.60-1.51 (2H, m), 1.28 (6H, td, J=1.3, 7.1 Hz). LC-MS: m/z=844.4 $[M+H]^+$.

Example 5: isopropyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy) prop-1-yn-1-yl)piperidine-1-carboxylate

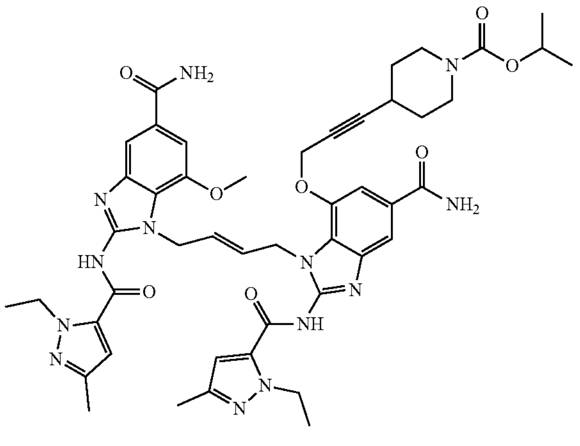 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)OC(C)C)CC3)c21]

To a solution of (E)-1-(4-(5-carbamoyl-2-(1-ethyl-3-methyl-1H-pyrazole-5-carboxamido)-7-((3-(piperidin-4-yl) prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 17.0 mg, 0.0190 mmol) in DCM (0.97 mL) was added isopropyl carbonochloridate (9.65 μL, 0.0190 mmol) and DIPEA (10.1 μL, 0.0580 mmol) at room temperature. The reaction mixture was stirred at room temperature for 20 min. After concentration in vacuo, the residue was purified by column chromatography on $SiO_2$ (DCM:MeOH:$NH_4OH$=93:7:1) to afford the title compound (7.1 mg, 40%) as a white solid. $^1H$ NMR (400 MHz, DMSO-$d_6$): δ 12.78 (2H, brs), 7.97 (1H, s), 7.90 (1H, s), 7.65 (2H, s), 7.36 (3H, s), 7.28 (1H, s), 6.54 (1H, s), 6.52 (1H, s), 5.94-5.82 (2H, m), 4.91 (4H, s), 4.74-4.68 (3H, m), 4.56-4.50 (4H, d, m), 3.67 (3H, s), 3.49-3.45 (2H, m), 2.95 (2H, t, J=10.0 Hz), 2.14-2.10 (6H, m), 1.57-1.54 (2H, m), 1.27 (8H, t, J=7.2 Hz), 1.13 (6H, d, J=6.4 Hz). LC-MS: m/z=930.3 $[M+H]^+$.

Example 6: cyclopropyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate

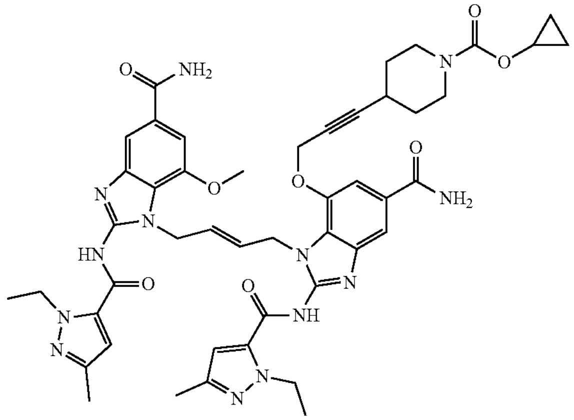 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)OC4CC4)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol) in DMF (0.23 mL) was added DIPEA (19.8 μL, 0.114 mmol) and cyclopropyl (4-nitrophenyl) carbonate (Intermediate 7, 5.07 mg, 0.0230 mmol) at room temperature. The reaction mixture was stirred at room temperature for 1 hour. After treatment with $Et_2O$, a precipitated solid was collected by filtration and purified by column chromatography on $SiO_2$ (DCM:MeOH:$NH_4OH$=97:7:1) to afford the title compound (15 mg, 72%) as a yellow solid. $^1H$ NMR (400 MHz, DMSO-$d_6$): δ 7.98 (1H, s), 7.90 (1H, s), 7.65 (2H, d, J=2.4 Hz), 7.36 (3H, s), 7.28 (1H, s), 6.54 (1H, s), 6.52 (1H, s), 5.94-5.83 (2H, m), 4.91 (4H, s), 4.68 (2H, s), 4.57-4.50 (4H, m), 3.95-3.90 (1H, m), 3.67 (3H, s), 3.63-3.59 (1H, m), 3.15-3.10 (1H, m), 2.96-2.91 (2H, m), 2.46-2.42 (1H, m), 2.11 (3H, s), 2.10 (3H, s), 1.59-1.511 (2H, m), 1.29-1.26 (8H, m), 0.60-0.55 (4H, m). LC-MS: m/z=928.3 $[M+H]^+$.

Example 7: cyclopentyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate

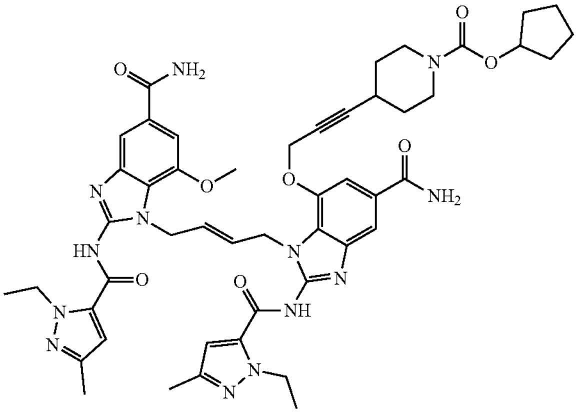 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)OC4CCCC4)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide (Example 4, 20.0 mg, 0.0240 mmol) in DMF (0.79 mL) was added cyclopentyl (4-nitrophenyl) carbonate (Intermediate 9, 6.55 mg, 0.0260 mmol) and DIPEA (0.0210 mL, 0.118 mmol) at room temperature. The reaction mixture was stirred at room temperature for 30 min. After quenched with saturated aq. $NaHCO_3$ solution, the mixture was extracted with DCM twice. The combined organic layers were dried over $Na_2SO_4$, filtered, and concentrated in vacuo. The residue was purified by column chromatography on $SiO_2$ (DCM:MeOH:$NH_4OH$=200:10:1 to 80:10:1) to afford the title compound (2.6 mg, 11%) as a light brown solid. $^1H$ NMR (400 MHz, DMSO-$d_6$): □□ 12.83 (2H, s), 7.96 (1H, s), 7.89 (1H, s), 7.65 (2H, d, J=3.2 Hz), 7.36 (3H, d, J=8.4 Hz), 7.28 (1H, s), 6.53 (2H, d, J=5.2 Hz), 5.90-5.87 (2H, m), 4.91 (5H, s), 4.68 (2H, s), 4.53 (4H, q, J=6.1 Hz), 3.69 (3H, s), 2.97-2.92 (2H, m), 2.52 (1H, s), 2.10 (6H, d, J=3.2 Hz), 1.74 (2H, s), 1.55-1.48 (8H, m), 1.27 (8H, t, J=7.2 Hz). LC-MS: m/z=956.3 $[M+H]^+$.

Example 8: 1-(tert-butoxycarbonyl)piperidin-4-yl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl) piperidine-1-carboxylate

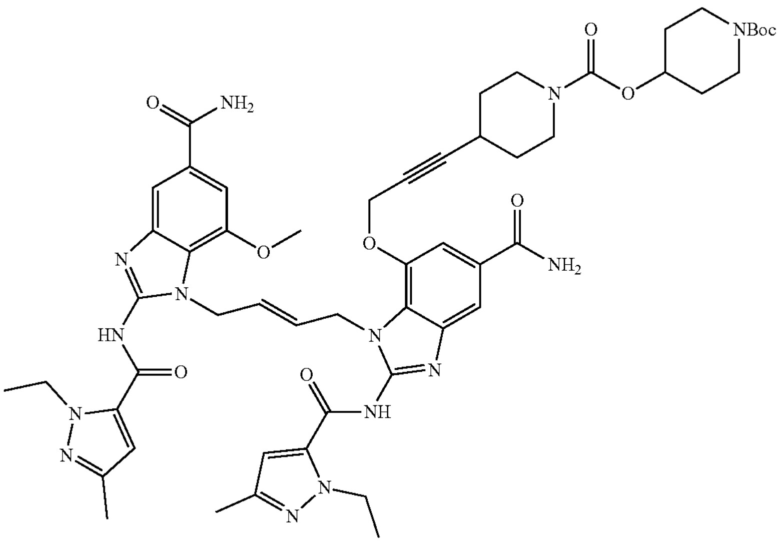 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)OC4CCN(C(=O)OC(C)(C)C)CC4)CC3)c21]

To a solution of (E)-1-(4-(5-carbamoyl-2-(1-ethyl-3-methyl-1H-pyrazole-5-carboxamido)-7-((3-(piperidin-4-yl) prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 50.0 mg, 0.0570 mmol) in DMF (0.57 mL) was added DIPEA (49.6 μL, 0.284 mmol) and tert-butyl 4-(((4-nitrophenoxy)carbonyl)oxy)piperidine-1-carboxylate (Intermediate 8, 20.8 mg, 0.0570 mmol) at room temperature. The reaction mixture was stirred at room temperature for 1 hour. After dilution of DCM/MeOH, the mixture was washed with saturated $NaHCO_3$ aqueous solution, dried over $Na_2SO_4$, filtered, and concentrated in vacuo. The residue was purified by column chromatography on $SiO_2$ (DCM:MeOH:$NH_4OH$=93:7:1) to afford title compound (32 mg, 53%) as a light brown solid. $^1$H NMR (400 MHz, DMSO-$d_6$): δ 7.98 (1H, s), 7.91 (1H, s), 7.65 (2H, d, J=3.2 Hz), 7.36 (3H, s), 7.27 (1H, s), 6.54 (1H, s), 6.53 (1H, s), 5.94-5.76 (2H, m), 4.91 (4H, s), 4.67 (3H, s), 4.53 (4H, d, J=6.4 Hz), 3.65 (3H, s), 3.49-3.44 (4H, m), 3.23-3.12 (2H, m), 3.04-2.93 (2H, m), 2.11 (3H, s), 2.10 (3H, s), 1.74-1.70 (2H, m), 1.60-1.54 (2H, m), 1.45-1.41 (2H, m), 1.38 (11H, s), 1.27 (6H, t, J=7.2 Hz). LC-MS: m/z=1071.5 [M+H]$^+$.

Example 9: piperidin-4-yl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy) prop-1-yn-1-yl)piperidine-1-carboxylate hydrochloride

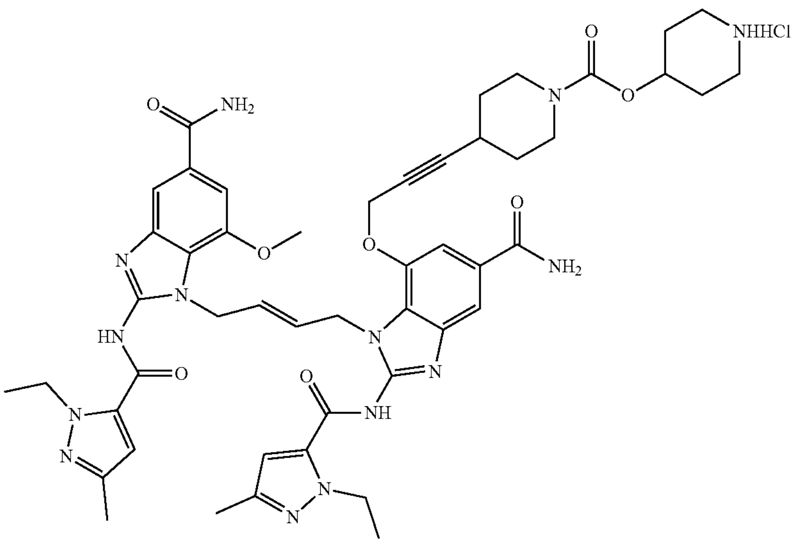

To a solution of 1-(tert-butoxycarbonyl)piperidin-4-yl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate (Example 8, 20.0 mg, 0.019 mmol) in DCM (0.93 mL) was added HCl (4 M HCl in dioxane, 233 μL, 0.934 mmol) at room temperature. The reaction mixture was stirred at room temperature for 1 hour. After concentration in vacuo, a residual solid was recrystallized from $Et_2O$/MeOH. The solid was collected by filtration, washed with $Et_2O$ and dried under vacuum to afford the title compound (10 mg, 53%) as a white solid. $^1H$ NMR (400 MHz, DMSO-$d_6$): δ 8.74 (2H, s), 8.01 (1H, s), 7.94 (1H, s), 7.66 (2H, s), 7.39 (3H, s), 7.30 (1H, s), 6.55 (1H, s), 6.53 (1H, s), 5.94-5.81 (2H, m), 4.92 (4H, d, J=4.0 Hz), 4.79-4.74 (1H, m), 4.70 (2H, s), 4.53 (4H, q, J=5.9 Hz), 3.68 (3H, s), 3.08 (6H, d, J=22.9 Hz), 2.67-2.64 (1H, m), 2.11 (3H, s), 2.10 (3H, s), 1.97-1.91 (2H, m), 1.76-1.68 (2H, m), 1.60-1.55 (2H, m), 1.34-1.26 (9H m). LC-MS: m/z=971.4 $[M+H]^+$.

Example 10: 2-hydroxyethyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate

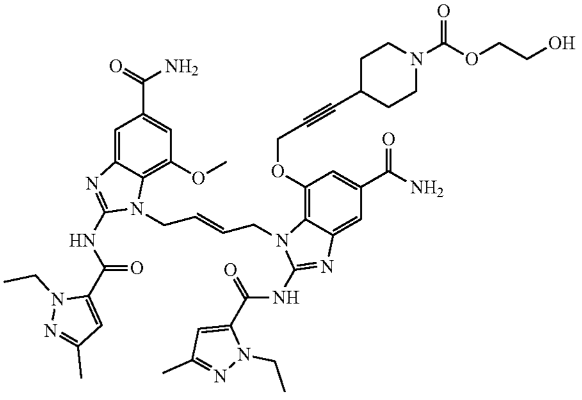 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)OCCO)CC3)c21]

Step A: 2-((tert-butyldimethylsilyl)oxy)ethyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide (Example 4, 50.0 mg, 0.0590 mmol) in DMF (2.0 mL) was added TEA (0.0410 mL, 0.296 mmol) and 2-((tert-butyldimethylsilyl)oxy)ethyl (4-nitrophenyl) carbonate (Intermediate 10, 40.0 mg, 0.118 mmol) at room temperature. The reaction mixture was stirred at room temperature for 30 min. After quenched with saturated aq. $NaHCO_3$ solution, the mixture was extracted with DCM twice. The combined organic layers were dried over $Na_2SO_4$, filtered, and concentrated in vacuo. The residue was purified by column chromatography on $SiO_2$ (DCM:MeOH:$NH_4OH$=200:10:1 to 80:10:1) to afford the title compound (32 mg, 51%) as a light brown solid. $^1H$ NMR (400 MHz, DMSO-$d_6$): □ 12.84 (2H, s), 7.98 (1H, s), 7.91 (1H, s), 7.65-7.65 (2H, m), 7.36 (3H, s), 7.28 (1H, s), 6.53 (2H, d, J=2.8 Hz), 5.91-5.87 (2H, m), 4.91 (4H, s), 4.67 (2H, s), 4.53 (4H, q, J=6.5 Hz), 3.99-3.99 (2H, m), 3.69 (2H, t, J=4.8 Hz), 3.66 (3H, s), 2.98-2.98 (2H, m), 2.09 (6H, d, J=3.2 Hz), 1.56-1.56 (2H, m), 1.27 (8H, t, J=7.0 Hz), 0.80 (9H, s), −0.02 (6H, s). LC-MS: m/z=1046.6 $[M+H]^+$.

Step B: 2-hydroxyethyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate To a solution of 2-((tert-butyldimethylsilyl)oxy)ethyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate (30.0 mg, 0.0290 mmol) in DCM (0.95 mL) was added HCl (4 M in dioxane, 0.0360 mL, 0.143 mmol) at room temperature. The reaction mixture was stirred at room temperature for 30 min. A precipitated solid was suspended in DCM/Hexanes and collected by filtration. The solid was purification by column chromatography on $SiO_2$ (DCM:MeOH:$NH_4OH$=200:10:1 to 80:10:1) to afford the title compound (8.0 mg, 29%) as a light brown solid. $^1H$ NMR (400 MHz, DMSO-$d_6$): □□ 8.00 (1H, s), 7.93 (1H, s), 7.65 (2H, d, J=0.8 Hz), 7.37 (3H, s), 7.29 (1H, s), 6.54 (2H, d, J=13.2 Hz), 5.89-5.84 (2H, m), 4.92-4.91 (4H, m), 4.68 (2H, s), 4.52 (4H, q, J=3.8 Hz), 3.95 (2H, t, J=5.2 Hz), 3.68 (3H, s), 3.59 (2H, s), 2.97-2.97 (2H, m), 2.46-2.46 (1H, m), 2.10 (6H, d, J=5.6 Hz), 1.58-1.56 (2H, m), 1.28 (8H, t, J=3.6 Hz). LC-MS: m/z=932.3 $[M+H]^+$.

Example 11: (E)-1-(4-(5-carbamoyl-2-(1-ethyl-3-methyl-1H-pyrazole-5-carboxamido)-7-((3-(1-pivaloylpiperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

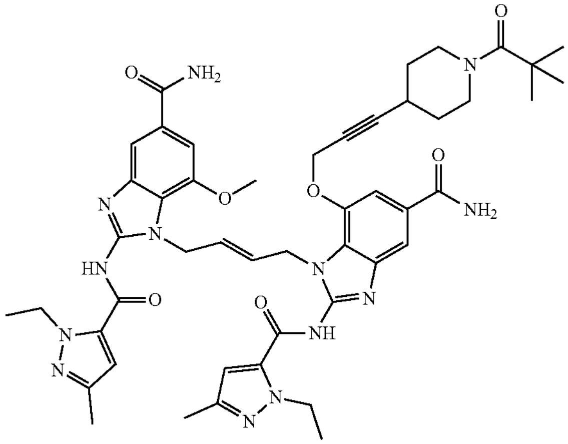 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)C(C)(C)C)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 15.0 mg, 0.017 mmol) in DMF (0.85 mL) was added pivaloyl chloride (3.13 μL, 0.0260 mmol) and DIPEA (8.93 μL, 0.0510 mmol) at room temperature. The reaction mixture was stirred at room temperature for 20 min. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ ($DCM:MeOH:NH_4OH$=93:7:1) to afford the title compound (3.8 mg, 24%) as a light brown solid. $^1H$ NMR (400 MHz, DMSO-$d_6$): δ 12.82 (2H, brs), 7.97 (1H, s), 7.90 (1H, s), 7.65 (2H, s), 7.37 (1H, s), 7.34 (2H, s), 7.28 (1H, s), 6.54 (1H, s), 6.52 (1H, s), 5.93-5.84 (2H, m), 4.91 (4H, s), 4.68 (2H, s), 4.53 (4H, d, J=6.8 Hz), 3.66-3.59 (5H, m), 3.10-3.04 (2H, m), 2.11 (3H, s), 2.10 (3H, s), 1.63-1.54 (2H, m), 1.29-1.23 (8H, m), 1.10 (9H, s). LC-MS: m/z=928.3 $[M+H]^+$.

Example 12: tert-butyl (E)-4-(4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carbonyl)piperidine-1-carboxylate

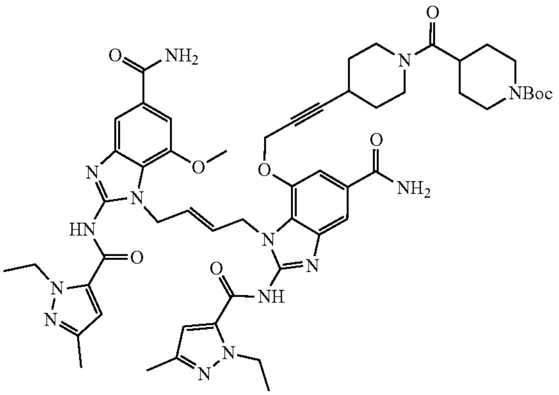

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol) in DMF (0.22 mL) was added 1-(tert-butoxycarbonyl)piperidine-4-carboxylic acid (6.25 mg, 0.0270 mmol), EDC (8.71 mg, 0.0450 mmol) and DIPEA (0.020 mL, 0.114 mmol). The reaction mixture was stirred at room temperature overnight and then heated at 60° C. for 5 hours. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ ($DCM:MeOH:NH_4OH$=93:7:1) to afford the title compound (5.1 mg, 21%) as a light brown solid. $^1H$ NMR (400 MHz, DMSO-$d_6$): δ 12.79 (2H, brs), 7.93 (1H, s), 7.86 (1H, s), 7.62 (2H, s), 7.35 (1H, s), 7.31 (2H, s), 7.25 (1H, s), 6.51 (1H, s), 6.49 (1H, s), 5.91-5.79 (2H, m), 4.88 (4H, s), 4.67 (2H, s), 4.49 (4H, d, J=8.0 Hz), 3.89-3.83 (2H, m), 3.65 (3H, s), 3.60-3.51 (2H, m), 3.15-2.93 (2H, m), 2.73-2.62 (3H, m), 2.07 (3H, s), 2.06 (3H, s), 1.96 (1H, q, J=7.6 Hz), 1.59-1.44 (4H, m), 1.34 (9H, s), 1.31-1.22 (10H, m). LC-MS: m/z=1055.4 $[M+H]^+$.

Example 13: (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-((3-(1-(1-ethyl-3-methyl-1H-pyrazole-5-carbonyl)piperidin-4-yl)prop-2-yn-1-yl)oxy)-2-(1-ethyl-3-methyl-1H-pyrazole-5-carboxamido)-1H-benzo[d]imidazole-5-carboxamide

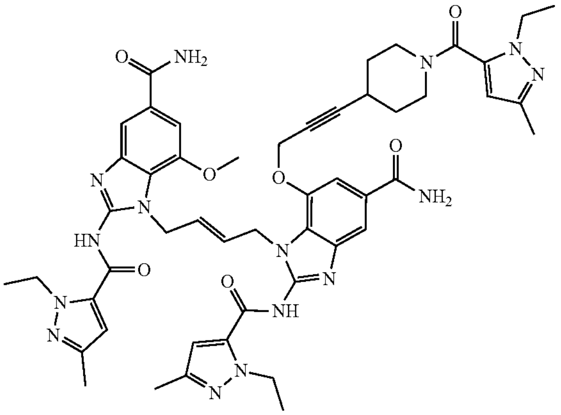 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)c4cc(C)nn4CC)CC3)c21]

To a solution of 1-ethyl-3-methyl-1H-pyrazole-5-carboxylic acid (5.25 mg, 0.0340 mmol) in DMF (0.45 mL) was added HATU (13.0 mg, 0.0340 mmol), HOBT (5.22 mg, 0.0340 mmol), and TEA (9.50 μL, 0.0680 mmol). The mixture was stirred at room temperature for 5 min. After addition of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol), the reaction mixture was stirred at room temperature for 40 min. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ ($DCM:MeOH:NH_4OH$=93:7:1) to afford the title compound (9.1 mg, 41%) as a light brown solid. $^1H$ NMR (400 MHz, DMSO-$d_6$): δ 12.85 (2H, brs), 7.99 (1H, s), 7.93 (1H, s), 7.66 (1H, s), 7.65 (1H, s), 7.39 (3H, s), 7.28 (1H, s), 6.54 (1H, s), 6.52 (1H, s), 6.09 (1H, s), 5.90-5.86 (2H, m), 4.91 (4H, s), 4.70 (2H, s), 4.52 (4H, d, J=5.2 Hz), 3.99 (2H, q, J=7.2 Hz), 3.66 (3H, s), 3.24-3.17 (2H, m), 2.58 (1H, s), 2.12 (3H, s), 2.10 (3H, s), 2.09 (3H, s), 1.64-1.59 (2H, m), 1.41-1.37 (2H, m), 1.28-1.24 (9H, m). LC-MS: m/z=980.4 $[M+H]^+$.

Example 14: (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-((3-(1-(cyclopropylcarbamoyl)piperidin-4-yl)prop-2-yn-1-yl)oxy)-2-(1-ethyl-3-methyl-1H-pyrazole-5-carboxamido)-1H-benzo[d]imidazole-5-carboxamide

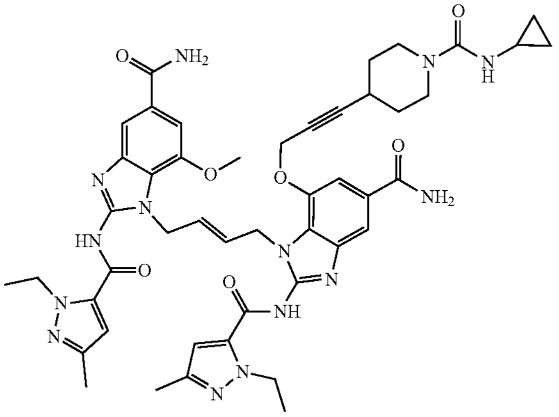 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)NC4CC4)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol) in DMF (0.23 mL) was added DIPEA (0.0198 mL, 0.114 mmol) and 4-nitrophenyl cyclopropylcarbamate (Intermediate 5, 5.05 mg, 0.0230 mmol) at room temperature. The reaction mixture was stirred at room temperature for 20 min. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM:MeOH:$NH_4OH$=93:7:1) to afford the title compound (5.3 mg, 25%) as a yellow solid. $^1H$ NMR (400 MHz, DMSO-$d_6$): δ 12.80 (2H, s), 7.99 (1H, s), 7.91 (1H, s), 7.65 (2H, s), 7.36 (3H, s), 7.28 (1H, s), 6.54 (1H, s), 6.52 (1H, s), 6.48 (1H, d, J=2.8 Hz), 5.94-5.84 (2H, m), 4.91 (4H, d, J=4.4 Hz), 4.68 (2H, s), 4.52 (4H, s), 3.68 (3H, s), 2.80 (2H, t, J=10.2 Hz), 2.46-2.43 (2H, m), 2.11 (3H, s), 2.09 (3H, s), 1.53-1.47 (2H, m), 1.27 (8H, t, J=7.2 Hz), 0.51-0.45 (2H, m), 0.34-0.30 (2H, m). LC-MS: m/z=927.2 $[M+H]^+$.

Example 15: (E)-1-(4-(5-carbamoyl-2-(1-ethyl-3-methyl-1H-pyrazole-5-carboxamido)-7-((3-(1-(morpholine-4-carbonyl)piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

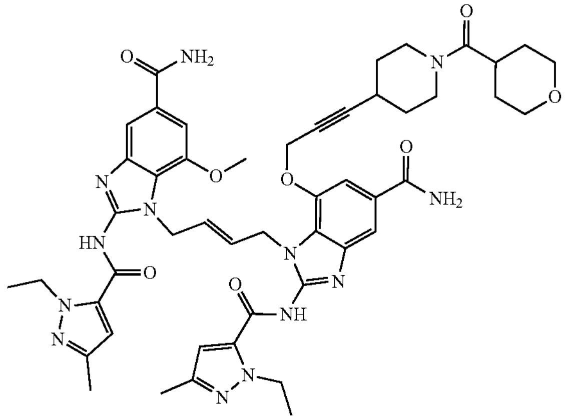 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)C4CCOCC4)CC3)c21]

To a solution of morpholine-4-carbonyl chloride (3.18 μL, 0.0270 mmol) and TEA (7.92 μL, 0.0570 mmol) in DMF (39 μL) was added (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol). The reaction mixture was heated to 120° C. for 1.5 hour. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM:MeOH:$NH_4OH$=93:7:1) to afford the title compound (20 mg, 93%) as a light brown solid. $^1H$ NMR (400 MHz, DMSO-$d_6$): δ 12.83 (2H, s), 7.97 (1H, s), 7.90 (1H, s), 7.65 (2H, s), 7.38 (1H, s), 7.35 (2H, s), 7.29 (1H, s), 6.54 (1H, s), 6.52 (1H, s), 5.94-5.83 (2H, m), 4.91 (4H, s), 4.70 (2H, s), 4.53 (4H, d, J=6.4 Hz), 3.68 (3H, s), 3.50 (4H, t, J=4.4 Hz), 3.20-3.17 (2H, m), 3.02 (4H, t, J=4.2 Hz), 2.79 (2H, t, J=9.6 Hz), 2.45 (1H, s), 2.11 (3H, s), 2.10 (3H, s), 1.58-1.55 (2H, m), 1.33-1.26 (8H, m). LC-MS: m/z=957.4 $[M+H]^+$.

Example 16: tert-butyl (E)-4-(4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carbonyl)piperazine-1-carboxylate

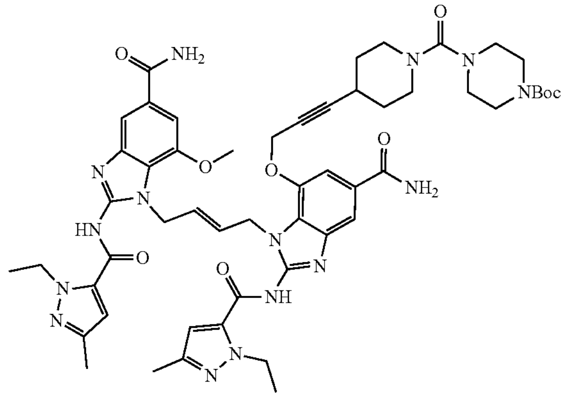 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)N4CCN(C(=O)OC(C)(C)C)CC4)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 40.0 mg, 0.0450 mmol) in DMF (0.45 mL) was added DIPEA (0.040 mL, 0.23 mmol) and 1-(tert-butyl) 4-(4-nitrophenyl) piperazine-1,4-dicarboxylate (Intermediate 6, 16.0 mg, 0.0450 mmol) at room temperature. The reaction mixture was stirred for 24 hours and then heated at 120° C. for 2 hours. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM:MeOH:$NH_4OH$=93:7:1) to afford the title compound (25 mg, 53%) as a light brown solid. $^1H$ NMR (400 MHz, DMSO-$d_6$): δ 12.84 (2H, s), 7.98 (1H, s), 7.91 (1H, s), 7.65 (2H, d, J=3.6 Hz), 7.37 (3H, s), 7.28 (1H, s), 6.54 (1H, s), 6.52 (1H, s), 5.94-5.82 (2H, m), 4.91 (4H, s), 4.68 (2H, s), 4.53 (4H, d, J=6.4 Hz), 3.66 (3H, s), 3.26 (4H, s), 3.20-3.17 (2H, m), 3.00 (4H, s), 2.79 (2H, t, J=9.8 Hz), 2.45 (1H, s), 2.11 (3H, s), 2.09 (3H, s), 1.58-1.55 (2H, m), 1.39 (9H, s), 1.32-1.25 (8H, m). LC-MS: m/z=1056.7 $[M+H]^+$.

Example 17: (E)-1-(4-(5-carbamoyl-2-(1-ethyl-3-methyl-1H-pyrazole-5-carboxamido)-7-((3-(1-(piperazine-1-carbonyl)piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride

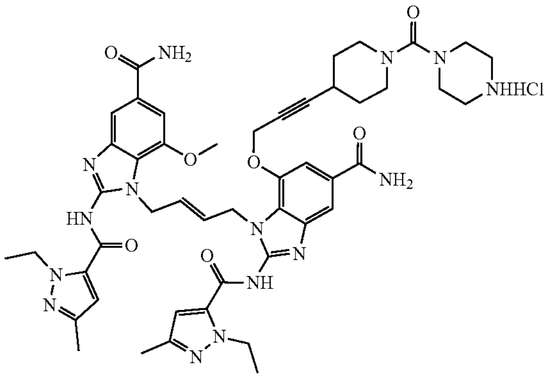

To a solution of tert-butyl (E)-4-(4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carbonyl)piperazine-1-carboxylate (Example 16, 10.0 mg, 9.47 μmol) in DCM (0.47 mL) was added HCl (4 M in dioxane, 0118 mL, 0.473 mmol) at room temperature. The reaction mixture was stirred for 1 hour. After concentration in vacuo, a residual solid was recrystallized from $Et_2O$ and MeOH, washed with $Et_2O$ and dried under vacuum to afford the title compound (6.1 mg, 65%) as a light brown solid. $^1H$ NMR (400 MHz, DMSO-$d_6$): δ 8.92 (2H, s), 8.01 (1H, s), 7.94 (1H, s), 7.65 (2H, t, J=1.0 Hz), 7.40 (1H, s), 7.38 (2H, s), 7.30 (1H, s), 6.55 (1H, s), 6.53 (1H, s), 5.94-5.81 (2H, m), 4.91 (4H, d, J=4.8 Hz), 4.70 (2H, s), 4.56-4.50 (4H, m), 3.69 (3H, s), 3.22 (6H, d, J=5.2 Hz), 3.04 (4H, s), 2.86-2.81 (2H, m), 2.54-2.53 (1H, m), 2.11 (3H, s), 2.10 (3H, s), 1.58-1.55 (2H, m), 1.35-1.25 (8H, m). LC-MS: m/z=956.4 $[M+H]^+$.

Example 18: (E)-1-(4-(5-carbamoyl-2-(1-ethyl-3-methyl-1H-pyrazole-5-carboxamido)-7-((3-(1-(4-hydroxypiperidine-1-carbonyl)piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

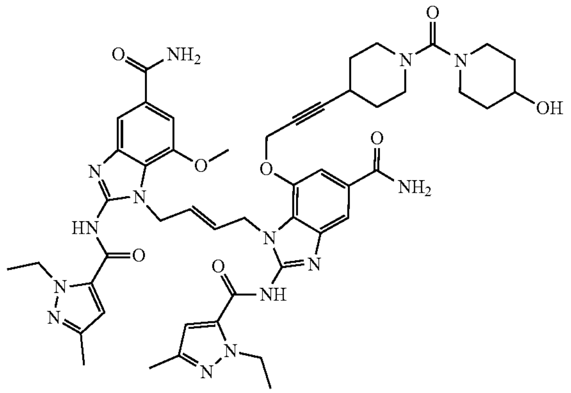 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)N4CCC(O)CC4)CC3)c21]

Step A: (E)-7-((3-(1-(4-((tert-butyldimethylsilyl)oxy)piperidine-1-carbonyl)piperidin-4-yl)prop-2-yn-1-yl)oxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 64.0 mg, 0.0730 mmol) in DMF (0.73 mL) was added DIPEA (0.064 mL, 0.36 mmol) and 4-nitrophenyl-4-((tert-butyldimethylsilyl)oxy)piperidine-1-carboxylate (Intermediate 11, 30.4 mg, 0.0800 mmol) at room temperature. The reaction mixture was stirred at 120° C. overnight. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM:MeOH:$NH_4OH$=93:7:1) to afford the title compound (12 mg, 16%) as a light brown solid. $^1H$ NMR (400 MHz, DMSO-$d_6$): δ 12.84 (2H, brs), 7.96 (1H, s), 7.90 (1H, s), 7.66 (2H, d, J=3.6 Hz), 7.37 (1H, s), 7.35 (2H, s) 7.28 (1H, s), 6.54 (1H, s), 6.53 (1H, s), 5.94-5.81 (2H, m), 4.92 (4H, s), 4.69 (2H, s), 4.53 (4H, q, J=6.7 Hz), 3.83-3.77 (1H, m), 3.66 (3H, s), 3.27-3.23 (2H, m), 3.19-3.15 (2H, m), 2.84 (2H, t, J=9.2 Hz), 2.76 (2H, t, J=9.8 Hz), 2.44 (1H, s), 2.11 (3H, s), 2.10 (3H, s), 1.63-1.56 (4H, m), 1.32-1.26 (10H, m), 0.85 (9H, s), 0.03 (6H, s)

Step B: (E)-1-(4-(5-carbamoyl-2-(1-ethyl-3-methyl-1H-pyrazole-5-carboxamido)-7-((3-(1-(4-hydroxypiperidine-1-carbonyl)piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide To a solution of (E)-7-((3-(1-(4-((tert-butyldimethylsilyl)oxy)piperidine-1-carbonyl)piperidin-4-yl)prop-2-yn-1-yl)oxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (12.2 mg, 0.0110 mmol) in DCM (0.38 mL) was added HCl (4 M in dioxane, 0.14 mL, 0.56 mmol) at room temperature. The reaction mixture was stirred at room temperature for 2 hours. A precipitated solid was recrystallized from $Et_2O$ and MeOH, washed with $Et_2O$, and dried under vacuum to afford the title compound (7.3 mg, 67%) as a light brown solid. $^1H$ NMR (400 MHz, DMSO-$d_6$): δ 12.83 (2H, brs), 7.97 (1H, s), 7.90 (1H, s), 7.66 (2H, d, J=2.0 Hz), 7.37 (1H, s), 7.35 (2H, s), 7.29 (1H, s), 6.55 (1H, s), 6.53 (1H, s), 5.96-5.83 (2H, m), 4.92 (4H, s), 4.68 (2H, s), 4.53 (4H, q, J=3.2 Hz), 3.67 (3H, s), 3.23-3.26 (2H, m), 3.19-3.16 (2H, m), 2.78-2.72 (4H, m), 2.42 (1H, s), 2.11 (3H, s), 2.10 (3H, s), 1.67-1.63 (2H, m), 1.58-1.55 (2H, m), 1.34-1.21 (10H, m). LC-MS: m/z=971.2 $[M+H]^+$.

Example 19: (E)-1-(4-(5-carbamoyl-2-(1-ethyl-3-methyl-1H-pyrazole-5-carboxamido)-7-((3-(1-(methylsulfonyl)piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

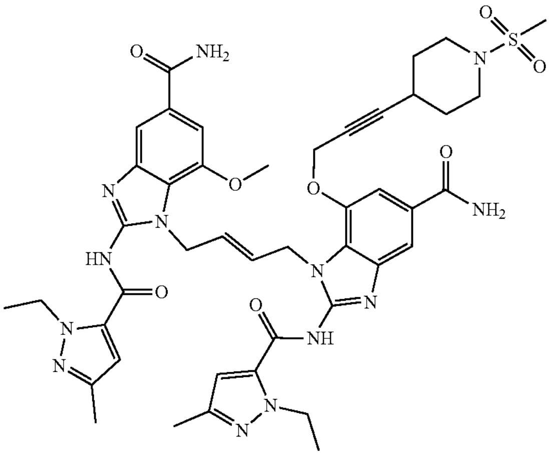 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(S(C)(=O)=O)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol) and TEA (7.0 μL, 0.050 mmol) in DCM (0.16 mL) was added MsCl (3.54 μL, 0.0450 mmol) at 0° C. The reaction mixture was stirred at temperature for 4 hours. After concentration in vacuo, the residue was purified by column chromatography on $SiO_2$ (DCM:MeOH:$NH_4OH$=93:7:1) to afford title compound (2.9 mg, 14%) as a white solid. $^1H$ NMR (400 MHz, DMSO-$d_6$): δ 7.97 (1H, s), 7.92 (1H, s), 7.65 (2H, s), 7.37 (3H, s), 7.28 (1H, s), 6.55 (1H, s), 6.52 (1H, s), 5.94-5.83 (2H, m), 4.92 (4H, d, J=3.6 Hz), 4.68 (2H, s), 4.54 (4H, t, J=5.6 Hz), 3.67 (3H, s), 3.17-3.13 (2H, m), 2.79-2.76 (5H, m), 2.43-2.41 (1H, m), 2.11 (3H, s), 2.10 (3H, s), 1.71-1.67 (2H, m), 1.46-1.40 (2H, m), 1.28 (6H, m). LC-MS: m/z=922.3 $[M+H]^+$.

Example 20: (E)-1-(4-(5-carbamoyl-2-(1-ethyl-3-methyl-1H-pyrazole-5-carboxamido)-7-((3-(1-(isopropylsulfonyl)piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

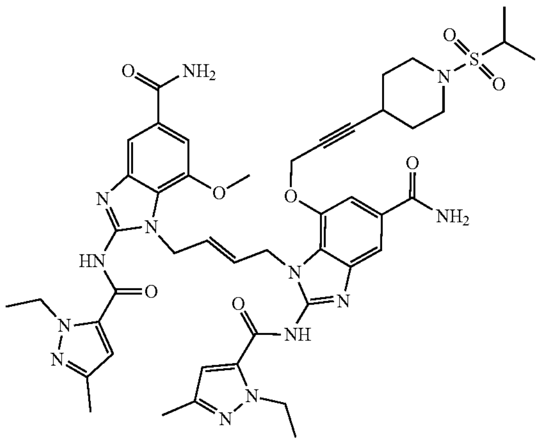

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol) and TEA (0.016 mL, 0.11 mmol) in DMF (0.16 mL) was added propane-2-sulfonyl chloride (5.06 μL, 0.0450 mmol) at 0° C. The reaction mixture was stirred at room temperature for 3 hours. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM:MeOH:$NH_4OH$=93:7:1) to afford the title compound (1.0 mg, 5%) as a white solid. $^1H$ NMR (400 MHz, DMSO-$d_6$): δ 7.97 (1H, s), 7.91 (1H, s), 7.66 (1H, s), 7.65 (1H, s), 7.38 (1H, s), 7.36 (2H, s), 7.29 (1H, s), 6.55 (1H, s), 6.53 (1H, s), 5.95-5.84 (2H, m), 4.92 (4H, s), 4.69 (2H, s), 4.54 (4H, s), 3.67 (3H, s), 3.21-3.11 (3H, m), 2.93 (2H, t, J=9.0 Hz), 2.12 (3H, s), 2.10 (3H, s), 1.65-1.60 (2H, m), 1.39-1.33 (2H, m), 1.28 (6H, t, J=7.2 Hz), 1.10 (3H, s), 1.09 (3H, s). LC-MS: m/z=950.3 $[M+H]^+$.

Example 21: (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-((3-(1-(cyclopropylsulfonyl)piperidin-4-yl)prop-2-yn-1-yl)oxy)-2-(1-ethyl-3-methyl-1H-pyrazole-5-carboxamido)-1H-benzo[d]imidazole-5-carboxamide

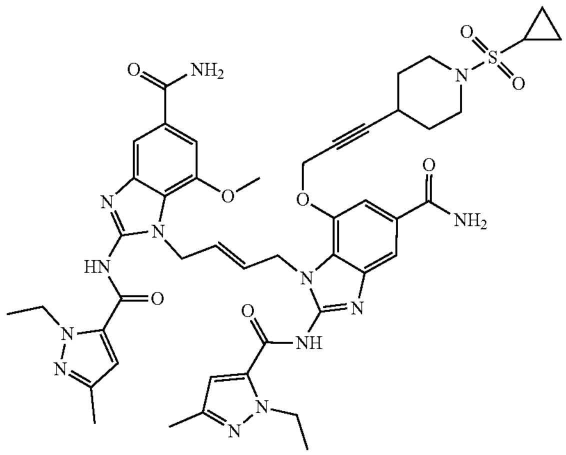 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(S(=O)(=O)C4CC4)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol) and TEA (0.016 mL, 0.11 mmol) in DMF (0.16 mL) was added cyclopropanesulfonyl chloride (4.63 μL, 0.0450 mmol) at 0° C. The reaction mixture was stirred at room temperature for 1 hour. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM:MeOH:$NH_4OH$=93:7:1) to afford the title compound (1.1 mg, 5%) as a white solid. $^1H$ NMR (400 MHz, DMSO-$d_6$): δ 7.97 (1H, s), 7.92 (1H, s), 7.66 (2H, s), 7.38 (1H, s), 7.37 (2H, s), 7.29 (1H, s), 6.55 (1H, s), 6.53 (1H, s), 5.95-5.85 (2H, m), 4.92 (4H, s), 4.68 (2H, s), 4.54 (4H, t, J=5.7 Hz), 3.68 (3H, s), 3.17 (2H, s), 2.86 (2H, t, J=8.9 Hz), 2.46-2.41 (1H, m), 2.38-2.32 (1H, m), 2.12 (3H, s), 2.10 (3H, s), 1.70-1.64 (2H, m), 1.46-1.38 (2H, m), 1.28 (6H, td, J=7.1, 1.5 Hz), 0.88-0.84 (4H, m). LC-MS: m/z=948.2 $[M+H]^+$.

Example 22: (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-((3-(1-(cyclopentylsulfonyl)piperidin-4-yl)prop-2-yn-1-yl)oxy)-2-(1-ethyl-3-methyl-1H-pyrazole-5-carboxamido)-1H-benzo[d]imidazole-5-carboxamide

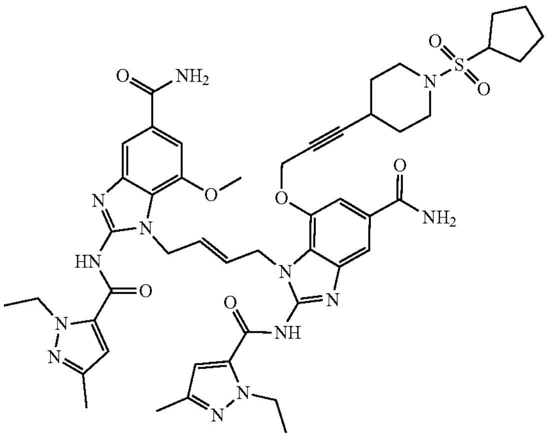

To a solution (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloric acid (Example 4, 15.0 mg, 0.0180 mmol) in DMF (1.7 mL) was added DIPEA (0.0190 mL, 0.107 mmol) and cyclopentanesulfonyl chloride (9.37 μL, 0.0710 mmol) at room temperature. The reaction mixture was stirred at room temperature for 1 hour. After quenched with saturated aq. $NaHCO_3$ solution, the mixture was extracted with DCM twice. The combined organic layers were dried over $Na_2SO_4$, filtered, and concentrated in vacuo. The residue was purified by column chromatography on $SiO_2$ (DCM:MeOH:$NH_4OH$=200:10:1 to 80:10:1) to afford the title compound (6.7 mg, 38%) as a light brown solid. $^1H$ NMR (400 MHz, DMSO-$d_6$): □□ 12.85 (2H, s), 7.97 (1H, s), 7.92 (1H, s), 7.66-7.65 (2H, m), 7.39 (1H, s), 7.37 (2H, s), 7.29 (1H, s), 6.54 (2H, d, J=8.0 Hz), 5.97-5.85 (2H, m), 4.92 (4H, s), 4.70 (2H, s), 4.58-4.51 (4H, m), 3.67 (3H, s), 3.10-3.08 (1H, m), 2.92-2.87 (1H, m), 2.10 (6H, d, J=7.6 Hz), 1.74-1.68 (2H, m), 1.66-1.52 (6H, m), 1.50-1.43 (2H, m), 1.40-1.35 (2H, m), 1.28 (6H, t, J=6.9 Hz). LC-MS: m/z=976.3 $[M+H]^+$.

Example 23: (E)-1-(4-(5-carbamoyl-2-(1-ethyl-3-methyl-1H-pyrazole-5-carboxamido)-7-((3-(1-tosylpiperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

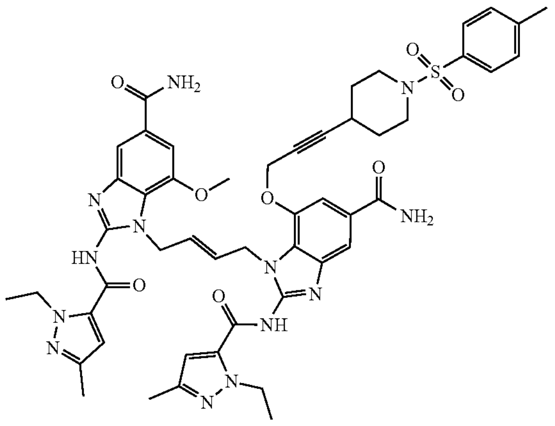 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(S(=O)(=O)c4ccc(C)cc4)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol) and TEA (0.016 mL, 0.11 mmol) in DMF (0.16 mL) was added p-TsCl (8.66 mg, 0.0450 mmol) at 0° C. The reaction mixture was stirred at room temperature for 20 min. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM:MeOH:$NH_4OH$=93:7:1) to afford the title compound (9.6 mg, 42%) as a white solid. $^1H$ NMR (400 MHz, DMSO-$d_6$): δ 12.85 (2H, s), 7.97 (1H, s), 7.90 (1H, s), 7.66 (1H, s), 7.65 (1H, s), 7.53 (1H, s), 7.51 (1H, s), 7.38 (2H, s), 7.36 (2H, s), 7.30 (1H, s), 7.26 (1H, s), 6.57 (1H, s), 6.51 (1H, s), 5.86-5.73 (2H, m), 4.85 (4H, dd, J=18.2, 4.2 Hz), 4.58-4.48 (6H, m), 3.62 (3H, s), 3.10-3.01 (2H, m), 2.37 (1H, s), 2.33 (3H, s), 2.12 (3H, s), 2.09 (3H, s), 1.71-1.62 (2H, m), 1.45-1.38 (2H, m), 1.31-1.27 (6H, m). LC-MS: m/z=998.4 $[M+H]^+$.

Example 24: (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-((3-(1-(N,N-dimethylsulfamoyl)piperidin-4-yl)prop-2-yn-1-yl)oxy)-2-(1-ethyl-3-methyl-1H-pyrazole-5-carboxamido)-1H-benzo[d]imidazole-5-carboxamide

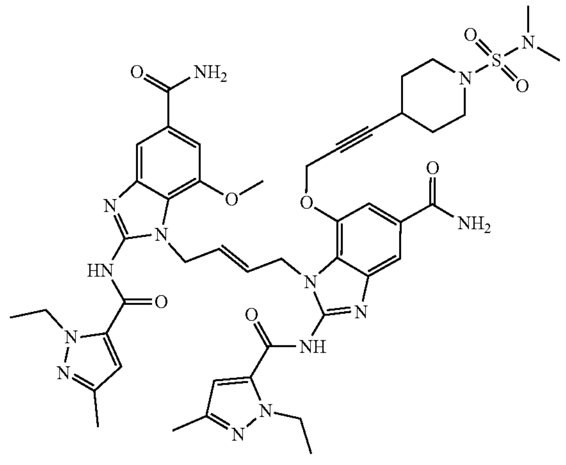 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(S(=O)(=O)N(C)C)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol) and TEA (0.016 mL, 0.11 mmol) in DMF (0.16 mL) was added dimethylsulfamoyl chloride (4.88 μL, 0.0450 mmol) at 0° C. The reaction mixture was stirred at room temperature for 1 hour. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM:MeOH:$NH_4OH$=93:7:1) to afford the title compound (8.4 mg, 39%) as a white solid. $^1H$ NMR (400 MHz, DMSO-$d_6$): δ 7.97 (1H, s), 7.91 (1H, s), 7.66 (1H, s), 7.65 (1H, s), 7.36 (3H, s), 7.28 (1H, s), 6.55 (1H, s), 6.53 (1H, s), 5.91-5.85 (2H, m), 4.92 (4H, s), 4.67 (2H, s), 4.54 (4H, d, J=6.4 Hz), 3.66 (3H, s), 3.26-3.18 (2H, m), 2.86-2.80 (2H, m), 2.65 (6H, s), 2.47-2.42 (1H, m), 2.12 (3H, s), 2.10 (3H, s), 1.68-1.62 (2H, m), 1.41-1.33 (2H, m), 1.28 (6H, t, J=7.0 Hz). LC-MS: m/z=951.2 $[M+H]^+$.

Example 25: (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-((3-(1-(N,N-diethylsulfamoyl)piperidin-4-yl)prop-2-yn-1-yl)oxy)-2-(1-ethyl-3-methyl-1H-pyrazole-5-carboxamido)-1H-benzo[d]imidazole-5-carboxamide

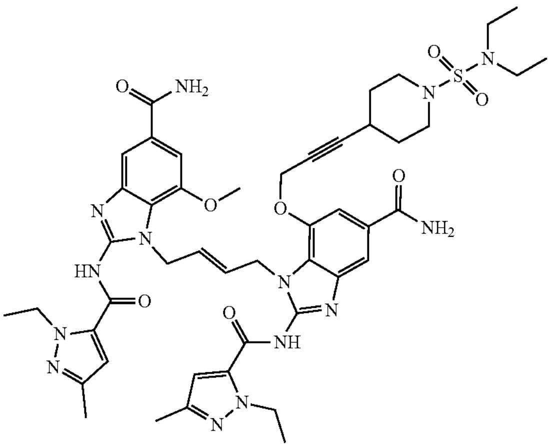 [SMILES: CCN(CC)S(=O)(=O)N1CCC(C#CCOc2cc(C(N)=O)cc3nc(NC(=O)c4cc(C)nn4CC)n(C/C=C/Cn4c(NC(=O)c5cc(C)nn5CC)nc5cc(C(N)=O)cc(OC)c54)c23)CC1]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol) and TEA (0.016 mL 0.114 mmol) in DMF (0.16 mL) was added diethylsulfamoyl chloride (5.83 μL 0.0450 mmol) dropwise at 0° C. The reaction mixture was stirred at room temperature for 3 hours. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM:MeOH:$NH_4OH$=93:7:1) to afford title compound (9.4 mg, 42%) as a white solid. $^1H$ NMR (400 MHz, DMSO-$d_6$): δ 7.98 (1H, s), 7.92 (1H, s), 7.67 (1H, s), 7.65 (1H, s), 7.37 (2H, s), 7.36 (1H, s), 7.28 (1H, s), 6.55 (1H, s), 6.53 (1H, s), 5.89-5.85 (2H, m), 4.91 (4H, s), 4.66 (2H, s), 4.53 (4H, d, J=6.0 Hz), 3.65 (3H, s), 3.10-3.04 (6H, m), 2.72 (2H, t, J=9.2 Hz), 2.46 (1H, s), 2.11 (3H, s), 2.10 (3H, s), 1.66-1.63 (2H, m), 1.42-1.37 (2H, m), 1.29-1.26 (6H, m), 1.01 (6H, t, J=7.0 Hz). LC-MS: m/z=979.3 $[M+H]^+$.

Example 26: (E)-1-(4-(5-carbamoyl-2-(1-ethyl-3-methyl-1H-pyrazole-5-carboxamido)-7-((3-(1-(pyrrolidin-1-ylsulfonyl)piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

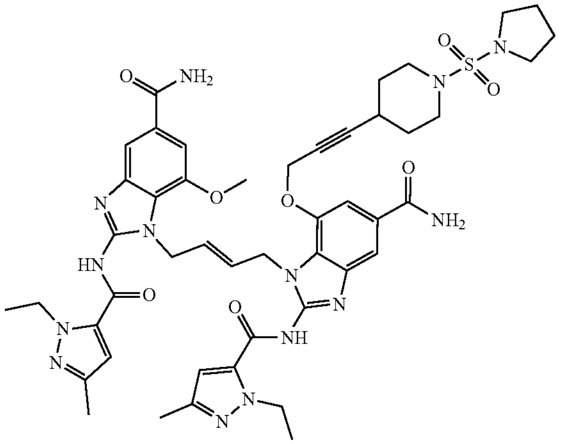 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(S(=O)(=O)N4CCCC4)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 20.0 mg, 0.0230 mmol) and TEA (0.016 mL, 0.11 mmol) in DMF (0.16 mL) was added pyrrolidine-1-sulfonyl chloride (5.21 μL, 0.0450 mmol) at 0° C. The reaction mixture was stirred at room temperature for 30 min. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM: MeOH:$NH_4OH$=93:7:1) to afford the title compound (9.5 mg, 43%) as a white solid. $^1H$ NMR (400 MHz, DMSO-$d_6$): δ 12.82 (2H, s), 7.97 (1H, s), 7.91 (1H, s), 7.67 (1H, s), 7.65 (1H, s), 7.36 (3H, s), 7.28 (1H, s), 6.55 (1H, s), 6.53 (1H, s), 5.94-5.82 (2H, m), 4.92 (4H, s), 4.67 (2H, s), 4.54 (4H, d, J=4.0 Hz), 3.66 (3H, s), 3.17-3.14 (2H, m), 3.07 (4H, t, J=6.6 Hz), 2.83-2.77 (2H, m), 2.44 (1H, s), 2.11 (3H, s), 2.10 (3H, s), 1.79-1.73 (4H, m), 1.66-1.63 (2H, m), 1.43-1.35 (2H, m), 1.28 (6H, t, J=7.2 Hz). LC-MS: m/z=977.5 $[M+H]^+$.

Example 27: (E)-1-(4-(5-carbamoyl-2-(1-ethyl-3-methyl-1H-pyrazole-5-carboxamido)-7-((3-(1-(morpholinosulfonyl)piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

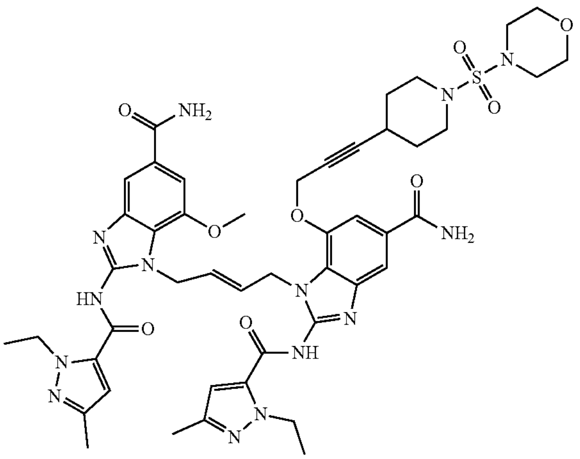 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(S(=O)(=O)N4CCOCC4)CC3)c21]

To a solution (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide (Example 4, 15.0 mg, 0.0180 mmol) in DMF (1.7 mL) was added TEA (0.0150 mL, 0.107 mmol) and morpholine-4-sulfonyl chloride (5.39 μL, 0.0440 mmol) at room temperature. The reaction mixture was stirred at room temperature for 30 min. After quenched with saturated aq. $NaHCO_3$ solution, the mixture was extracted with DCM twice. The combined organic layers were dried over $Na_2SO_4$, filtered, and concentrated in vacuo. The residue was purified by column chromatography on $SiO_2$ (DCM:MeOH:$NH_4OH$=200:10:1 to 80:10:1) to afford the title compound (6.2 mg, 35%) as a light brown solid. $^1H$ NMR (400 MHz, DMSO-$d_6$): □□ 12.85 (2H, s), 7.97 (1H, s), 7.91 (1H, s), 7.65 (2H, s), 7.36 (3H, s), 7.28 (1H, s), 6.55 (1H, s), 6.53 (1H, s), 5.91-5.87 (2H, m), 4.92 (4H, brs), 4.67 (2H, s), 4.54-4.53 (4H, m), 3.67 (3H, s), 3.55 (4H, t, J=4.6 Hz), 3.24-3.21 (2H, m), 2.99 (4H, t, J=4.6 Hz), 2.88 (2H, t, J=9.0 Hz), 2.46 (1H, s), 2.11 (6H, d, J=6.0 Hz), 1.64-1.60 (2H, m), 1.39-1.37 (2H, m), 1.28 (6H, t, J=7.2 Hz). LC-MS: m/z=993.3 $[M+H]^+$.

Example 28: tert-butyl (E)-4-((4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidin-1-yl)sulfonyl)piperazine-1-carboxylate

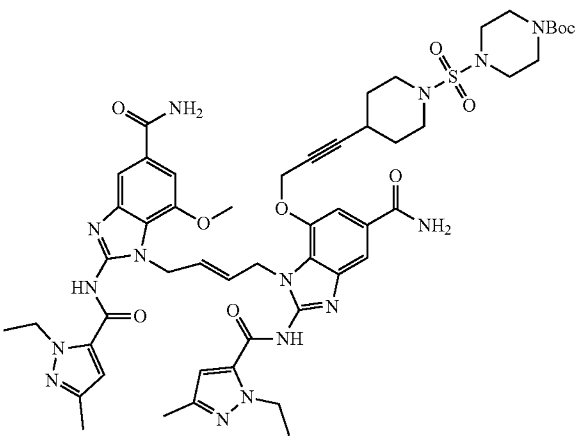 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(S(=O)(=O)N4CCN(C(=O)OC(C)(C)C)CC4)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 50.0 mg, 0.0570 mmol) and TEA (0.040 mL, 0.28 mmol) in DMF (0.41 mL) was added tert-butyl 4-(chlorosulfonyl)piperazine-1-carboxylate (Intermediate 4, 32.3 mg, 0.114 mmol) at 0° C. The reaction mixture was stirred at room temperature for 1 hour. After dilution with DCM/MeOH, the mixture was washed saturated aq. $NaHCO_3$ solution, dried over $Na_2SO_4$, filtered, and concentrated in vacuo. The residue was purified by column chromatography on $SiO_2$ (DCM:MeOH:$NH_4OH$=93:7:1) to afford the title compound (46 mg, 74%) as a light brown solid. $^1H$ NMR (400 MHz, DMSO-$d_6$): δ 12.84 (2H, brs), 7.98 (1H, s), 7.91 (1H, s), 7.66 (1H, s), 7.65 (1H, s), 7.37 (2H, s), 7.34 (1H, s), 7.27 (1H, s), 6.56 (1H, s), 6.53 (1H, s), 5.93-5.82 (2H, m), 4.91 (4H, d, J=4.0 Hz), 4.63 (2H, s), 4.53 (4H, d, J=6.0 Hz), 3.63 (3H, s), 3.28-3.23 (2H, m), 3.02 (4H, t, J=5.0 Hz), 2.83 (2H, t, J=9.6 Hz), 2.42 (1H, s), 2.12 (3H, s), 2.10 (3H, s), 1.66-1.64 (2H, m), 1.41-1.35 (11H, m), 1.28 (6H, t, J=7.0 Hz). LC-MS: m/z=1092.4 $[M+H]^+$.

Example 29: (E)-1-(4-(5-carbamoyl-2-(1-ethyl-3-methyl-1H-pyrazole-5-carboxamido)-7-((3-(1-(piperazin-1-ylsulfonyl)piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride

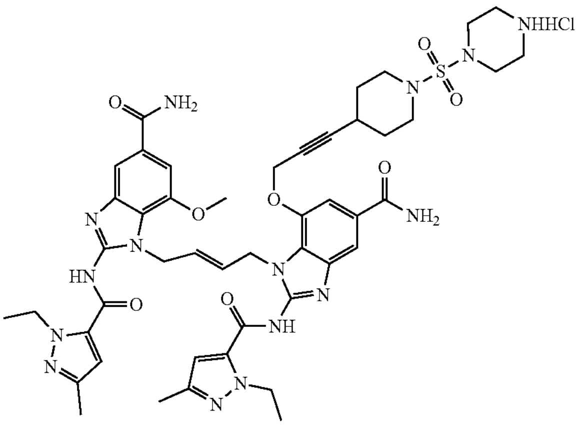

To a solution of tert-butyl (E)-4-((4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidin-1-yl)sulfonyl)piperazine-1-carboxylate (Example 28, 20.0 mg, 0.0180 mmol) in DCM (0.92 mL) was added HCl (4 M in dioxane, 0.23 mL, 0.92 mmol) at room temperature. The reaction mixture was stirred for 1.5 hours. After concentration in vacuo, a residual solid was recrystallized from $Et_2O$ and MeOH, washed with $Et_2O$ and dried under vacuum to afford the title compound (12 mg, 64%) as a white solid. $^1H$ NMR (400 MHz, DMSO-$d_6$): δ 9.00 (2H, s), 8.02 (1H, s), 7.96 (1H, s), 7.66 (2H, dd, J=3.4, 1.4 Hz), 7.39 (3H, s), 7.30 (1H, s), 6.56 (1H, s), 6.52 (1H, s), 5.94-5.82 (2H, m), 4.92 (4H, d, J=4.4 Hz), 4.70 (2H, s), 4.54-4.50 (4H, m), 3.68 (3H, s), 3.31-3.23 (6H, m), 3.14 (4H, s), 2.86 (2H, t, J=9.6 Hz), 2.43 (1H, s), 2.11 (3H, s), 2.10 (3H, s), 1.67-1.64 (2H, m), 1.43-1.35 (2H, m), 1.28 (6H, td, J=7.1, 1.2 Hz). LC-MS: m/z=992.3 $[M+H]^+$.

Example 30: tert-butyl (E)-3-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)azetidine-1-carboxylate

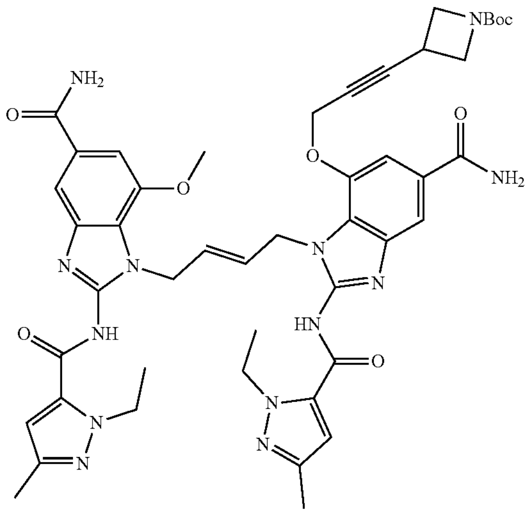 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CN(C(=O)OC(C)(C)C)C3)c21]

Step A: tert-butyl (E)-3-(3-(5-carbamoyl-2-((4-((2-methoxy-4-(methoxycarbonyl)-6-nitrophenyl)amino)but-2-en-1-yl)amino)-3-nitrophenoxy)prop-1-yn-1-yl)azetidine-1-carboxylate The title compound was prepared in a similar fashion to Example 1 (Step A) with methyl (E)-4-((4-aminobut-2-en-1-yl)amino)-3-methoxy-5-nitrobenzoate (Intermediate 1) and tert-butyl 3-(3-(5-carbamoyl-2-chloro-3-nitrophenoxy)prop-1-yn-1-yl)azetidine-1-carboxylate (Intermediate 12). The crude product was purified by column chromatography on $SiO_2$ (DCM:MeOH=99:1 to 20:1) to afford the title compound (55%) as a reddish foam. $^1$H NMR (400 MHz, DMSO-$d_6$): δ 8.17 (1H, d, J=2.0 Hz), 8.09 (1H, d, J=2.0 Hz), 7.97 (1H, d, J=1.6 Hz), 7.75 (1H, t, J=6.4 Hz), 7.58 (1H, d, J=1.6 Hz), 7.33 (2H, d, J=1.6 Hz), 5.57 (2H, s), 4.81 (2H, d, J=1.2 Hz), 4.06-4.04 (6H, m), 3.83 (3H, s), 3.79 (3H, s), 3.70-3.66 (3H, m), 3.58 (1H, s), 1.34 (9H, s). LC-MS: m/z=669.1 $[M+H]^+$.

Step B: tert-butyl (E)-3-(3-(3-amino-2-((4-((2-amino-6-methoxy-4-(methoxycarbonyl)phenyl)amino)but-2-en-1-yl)amino)-5-carbamoylphenoxy)prop-1-yn-1-yl)azetidine-1-carboxylate The title compound was prepared in a similar fashion to Example 1 (Step B) with tert-butyl (E)-3-(3-(5-carbamoyl-2-((4-((2-methoxy-4-(methoxycarbonyl)-6-nitrophenyl)amino)but-2-en-1-yl)amino)-3-nitrophenoxy)prop-1-yn-1-yl)azetidine-1-carboxylate. The crude product was used for the next reaction without purification as a white foam. LC-MS: m/z=609.02 $[M+H]^+$.

Step C: methyl (E)-2-amino-1-(4-(2-amino-7-((3-(1-(tert-butoxycarbonyl)azetidin-3-yl)prop-2-yn-1-yl)oxy)-5-carbamoyl-1H-benzo[d]imidazol-1-yl)but-2-en-1-yl)-7-methoxy-1H-benzo[d]imidazole-5-carboxylate dihydrobromide The title compound was prepared in a similar fashion to Example 1 (Step C) with tert-butyl (E)-3-(3-(3-amino-2-((4-((2-amino-6-methoxy-4-(methoxycarbonyl)phenyl)amino)but-2-en-1-yl)amino)-5-carbamoylphenoxy)prop-1-yn-1-yl)azetidine-1-carboxylate. The crude product was used for the next reaction without purification as a light brown solid. LC-MS: m/z=659.2 $[M+H]^+$.

Step D: methyl (E)-1-(4-(7-((3-(1-(tert-butoxycarbonyl)azetidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 1 (Step D) with methyl (E)-2-amino-1-(4-(2-amino-7-((3-(1-(tert-butoxycarbonyl)azetidin-3-yl)prop-2-yn-1-yl)oxy)-5-carbamoyl-1H-benzo[d]imidazol-1-yl)but-2-en-1-yl)-7-methoxy-1H-benzo[d]imidazole-5-carboxylate dihydrobromide and 1-ethyl-3-methyl-1H-pyrazole-5-carboxylic acid. The crude product was purified by column chromatography on $SiO_2$ (DCM:MeOH:$NH_4OH$=200:10:1 to 80:10:1) to afford the title compound (37% for 3 steps) as a light brown oil. $^1$H NMR (400 MHz, DMSO-$d_6$): □□ 12.86 (2H, brs), 7.91 (1H, s), 7.76 (1H, d, J=0.8 Hz), 7.66 (1H, s), 7.34 (2H, s), 7.21 (1H, s), 6.55 (1H, s), 6.47 (1H, s), 5.92-5.83 (2H, m), 4.91 (4H, d, J=3.6 Hz), 4.69 (2H, s), 4.54-4.50 (4H, m), 3.97 (2H, t, J=8.2 Hz), 3.86 (3H, s), 3.64-3.63 (1H, m), 3.61 (2H, s), 3.56 (3H, s), 2.10 (6H, d, J=4.4 Hz), 1.31 (9H, s), 1.30-1.24 (6H, m). LC-MS: m/z=931.3 $[M+H]^+$.

Step E: (E)-1-(4-(7-((3-(1-(tert-butoxycarbonyl)azetidin-3-yl)prop-2-yn-1-yl)oxy)- 5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(7-((3-(1-(tert-butoxycarbonyl)azetidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate. The crude solid product was suspended in acetone/hexanes, collected by filtration, washed with hexanes, and dried under vacuum to afford the title compound (37%) as a light brown solid. $^1$H NMR (400 MHz, DMSO-$d_6$): δ 12.83 (2H, s), 7.98 (1H, s), 7.73 (1H, s), 7.66 (1H, s), 7.36 (2H, s), 7.27 (1H, d, J=1.2 Hz), 6.54 (1H, s), 6.51 (1H, s), 5.87-5.83 (2H, m), 4.91 (4H, d, J=4.0 Hz), 4.70 (2H, s), 4.52 (4H, t, J=6.6 Hz), 3.98 (2H, t, J=8.6 Hz), 3.67-3.61 (5H, m), 2.11 (6H, s), 1.31 (9H, s), 1.29-1.25 (6H, m). LC-MS: m/z=917.3 $[M+H]^+$.

Step F: tert-butyl (E)-3-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)azetidine-1-carboxylate The title compound was prepared in a similar fashion to Example 3 with (E)-1-(4-(7-((3-(1-(tert-butoxycarbonyl)

azetidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid. The crude product was purified by column chromatography on $SiO_2$ (DCM:MeOH:$NH_4OH$=200:10:1 to 80:10:1) to afford the title compound (23%) as a white solid. $^1H$ NMR (400 MHz, DMSO-$d_6$): □□ 12.83 (2H, d, J=7.3 Hz), 7.96 (1H, s), 7.92 (1H, s), 7.66 (1H, s), 7.64 (1H, d, J=0.9 Hz), 7.39 (1H, s), 7.35 (2H, s), 7.28 (1H, s), 6.53 (2H, s), 5.93-5.82 (2H, m), 4.92 (4H, s), 4.76 (2H, s), 4.53 (4H, q, J=6.3 Hz), 3.98 (2H, t, J=8.2 Hz), 3.68 (3H, s), 3.62 (2H, t, J=7.0 Hz), 2.10 (6H, s), 1.31 (9H, s), 1.29-1.25 (6H, m). LC-MS: m/z=916.3 $[M+H]^+$.

Example 31: tert-butyl (E)-3-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)pyrrolidine-1-carboxylate

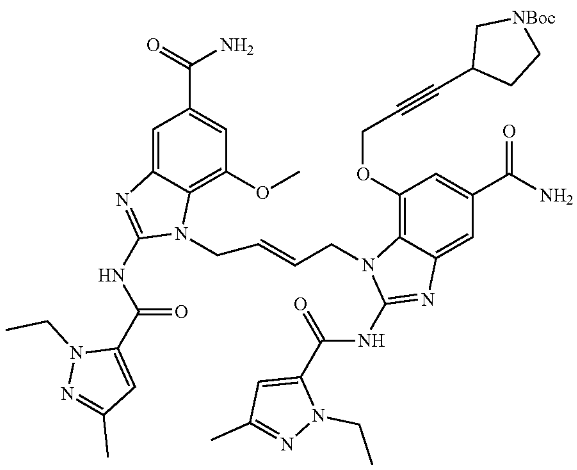 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)OC(C)(C)C)C3)c21]

Step A: tert-butyl (E)-3-(3-(5-carbamoyl-2-((4-((2-methoxy-4-(methoxycarbonyl)-6-nitrophenyl)amino)but-2-en-1-yl)amino)-3-nitrophenoxy)prop-1-yn-1-yl)pyrrolidine-1-carboxylate The title compound was prepared in a similar fashion to Example 1 (Step A) with tert-butyl 3-(3-(5-carbamoyl-2-chloro-3-nitrophenoxy)prop-1-yn-1-yl)pyrrolidine-1-carboxylate (Intermediate 13) and methyl (E)-4-((4-aminobut-2-en-1-yl)amino)-3-methoxy-5-nitrobenzoate hydrochloride (Intermediate 1). The crude product was purified by column chromatography on NH—$SiO_2$ (DCM only to DCM: MeOH=98:2) to afford the title compound (77%) as an orange solid. LC-MS: m/z=683.2 $[M+H]^+$.

Step B: tert-butyl (E)-3-(3-(3-amino-2-((4-((2-amino-6-methoxy-4-(methoxycarbonyl)phenyl)amino)but-2-en-1-yl)amino)-5-carbamoylphenoxy)prop-1-yn-1-yl)pyrrolidine-1-carboxylate The title compound was prepared in a similar fashion to Example 1 (Step B) with tert-butyl (E)-3-(3-(5-carbamoyl-2-((4-((2-methoxy-4-(methoxycarbonyl)-6-nitrophenyl)amino)but-2-en-1-yl)amino)-3-nitrophenoxy)prop-1-yn-1-yl)pyrrolidine-1-carboxylate. The crude product was used for the next reaction without purification as a light brown solid. LC-MS: m/z=623.2 $[M+H]^+$.

Step C: methyl (E)-2-amino-1-(4-(2-amino-7-((3-(1-(tert-butoxycarbonyl)pyrrolidin-3-yl)prop-2-yn-1-yl)oxy)-5-carbamoyl-1H-benzo[d]imidazol-1-yl)but-2-en-1-yl)-7-methoxy-1H-benzo[d]imidazole-5-carboxylate dihydrobromide The title compound was prepared in a similar fashion to Example 1 (Step C) with tert-butyl (E)-3-(3-(3-amino-2-((4-((2-amino-6-methoxy-4-(methoxycarbonyl)phenyl)amino)but-2-en-1-yl)amino)-5-carbamoylphenoxy)prop-1-yn-1-yl)pyrrolidine-1-carboxylate. The crude product was recrystallized from $Et_2O$/MeOH, washed with $Et_2O$ and dried under vacuum to afford the title compound (82%) as a yellow solid. LC-MS: m/z=673.2 $[M+H]^+$.

Step D: methyl (E)-1-(4-(7-((3-(1-(tert-butoxycarbonyl)pyrrolidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 1 (Step D) with methyl (E)-2-amino-1-(4-(2-amino-7-((3-(1-(tert-butoxycarbonyl)pyrrolidin-3-yl)prop-2-yn-1-yl)oxy)-5-carbamoyl-1H-benzo[d]imidazol-1-yl)but-2-en-1-yl)-7-methoxy-1H-benzo[d]imidazole-5-carboxylate dihydrobromide and 1-ethyl-3-methyl-1H-pyrazole-5-carboxylic acid. The crude product was purified by column chromatography on $SiO_2$ (DCM:MeOH:$NH_4OH$=95:5:1) to afford the title compound (31%) as a light brown solid. $^1H$ NMR (400 MHz, DMSO-$d_6$): δ 12.86 (2H, s), 7.87 (1H, s), 7.77 (1H, d, J=1.2 Hz), 7.67 (1H, s), 7.35 (1H, s), 7.31 (1H, s), 7.20 (1H, s), 6.55 (1H, s), 6.50 (1H, s), 5.91-5.80 (2H, m), 4.93-4.89 (4H, m), 4.62 (2H, s), 4.56-4.51 (4H, m), 3.86 (3H, s), 3.59 (3H, s), 3.09-2.92 (3H, m), 2.11 (6H, s), 1.99-1.91 (1H, m), 1.70-1.61 (1H, m), 1.34 (10H, d, J=4.8 Hz), 1.28 (6H, dd, J=12.2, 7.0 Hz).

Step E: (E)-1-(4-(7-((3-(1-(tert-butoxycarbonyl)pyrrolidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(7-((3-(1-(tert-butoxycarbonyl)pyrrolidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate. The crude solid product was collected by filtration, washed with water, and dried under vacuum to afford the title compound (91%) as a light brown solid. $^1H$ NMR (400 MHz, DMSO-$d_6$): δ 12.85 (2H, d, J=11.6 Hz), 7.89 (1H, s), 7.76 (1H, d, J=1.2 Hz), 7.66 (1H, s), 7.36 (1H, s), 7.34 (1H, s), 7.27 (1H, s), 6.53 (1H, s), 6.50 (1H, s), 5.93-5.82 (2H, m), 4.92 (4H, s), 4.70 (2H, s), 4.53 (4H, q, J=6.8 Hz), 3.66 (3H, s), 3.11-2.92 (3H, m), 2.10 (6H, s), 1.99-1.92 (1H, m), 1.70-1.62 (1H, m), 1.33 (10H, d, J=6.0 Hz), 1.27 (6H, td, J=7.1, 3.5 Hz).

Step F: tert-butyl (E)-3-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)pyrrolidine-1-carboxylate The title compound was prepared in a similar fashion to Example 3 with (E)-1-(4-(7-((3-(1-(tert-butoxycarbonyl)pyrrolidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid. The crude product was purified by column chromatography on NH—$SiO_2$ (DCM:MeOH=93:7) to afford the title compound (63%) as a light brown solid. $^1$H NMR (400 MHz, DMSO-$d_6$): δ 12.83 (2H, s), 7.95 (1H, s), 7.90 (1H, s), 7.66 (1H, s), 7.65 (1H, s), 7.35 (3H, s), 7.27 (1H, s), 6.53 (2H, s), 5.94-5.80 (2H, m), 4.91 (4H, s), 4.69 (2H, s), 4.52 (4H, q, J=6.4 Hz), 3.66 (3H, s), 3.24-3.15 (1H, m), 3.11-3.08 (1H, m), 3.05-3.01 (1H, m), 2.95-2.90 (1H, m), 2.10 (6H, d, J=2.0 Hz), 1.98-1.89 (1H, m), 1.71-1.64 (1H, m), 1.34 (10H, d, J=6.0 Hz), 1.27 (6H, td, J=7.1, 1.9 Hz). LC-MS: m/z=930.3 [M+H]$^+$.

Example 32: tert-butyl (E)-3-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate

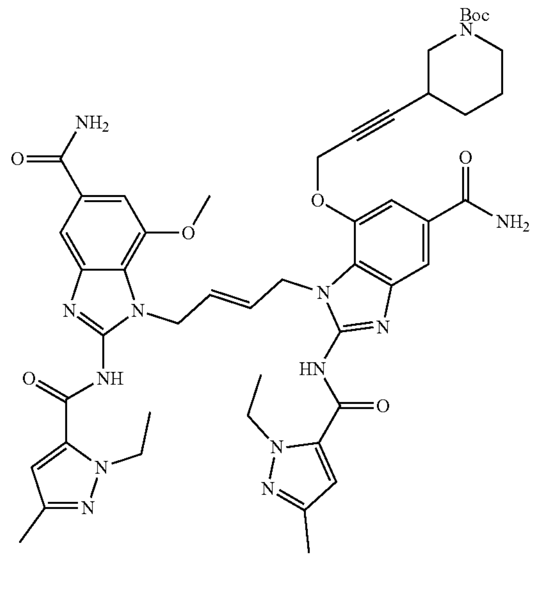 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCCN(C(=O)OC(C)(C)C)C3)c21]

Step A: tert-butyl (E)-3-(3-(5-carbamoyl-2-((4-((2-methoxy-4-(methoxycarbonyl)-6-nitrophenyl)amino)but-2-en-1-yl)amino)-3-nitrophenoxy)prop-1-yn-1-yl)piperidine-1-carboxylate The title compound was prepared in a similar fashion to Example 1 (Step A) with methyl (E)-4-((4-aminobut-2-en-1-yl)amino)-3-methoxy-5-nitrobenzoate (Intermediate 1) and tert-butyl 3-(3-(5-carbamoyl-2-chloro-3-nitrophenoxy)prop-1-yn-1-yl)piperidine-1-carboxylate (Intermediate 14). The crude product was purified by column chromatography on $SiO_2$ (DCM:MeOH:$NH_4OH$=200:10:1) to afford the title compound (>99%) as a reddish foam. LC-MS: m/z=697.2 [M+H]$^+$.

Step B: tert-butyl (E)-3-(3-(3-amino-2-((4-((2-amino-6-methoxy-4-(methoxycarbonyl)phenyl)amino)but-2-en-1-yl)amino)-5-carbamoylphenoxy)prop-1-yn-1-yl)piperidine-1-carboxylate The title compound was prepared in a similar fashion to Example 1 (Step B) with tert-butyl (E)-3-(3-(5-carbamoyl-2-((4-((2-methoxy-4-(methoxycarbonyl)-6-nitrophenyl)amino)but-2-en-1-yl)amino)-3-nitrophenoxy)prop-1-yn-1-yl)piperidine-1-carboxylate. The crude product was used for the next reaction without purification as a light brown foam. LC-MS: m/z=637.3 [M+H]$^+$.

Step C: methyl (E)-2-amino-1-(4-(2-amino-7-((3-(1-(tert-butoxycarbonyl)piperidin-3-yl)prop-2-yn-1-yl)oxy)-5-carbamoyl-1H-benzo[d]imidazol-1-yl)but-2-en-1-yl)-7-methoxy-1H-benzo[d]imidazole-5-carboxylate dihydrobromide The title compound was prepared in a similar fashion to Example 1 (Step C) with tert-butyl (E)-3-(3-(3-amino-2-((4-((2-amino-6-methoxy-4-(methoxycarbonyl)phenyl)amino)but-2-en-1-yl)amino)-5-carbamoylphenoxy)prop-1-yn-1-yl)piperidine-1-carboxylate. The crude product was used for the next reaction without purification as a light brown solid. LC-MS: m/z=687.3 [M+H]$^+$.

Step D: methyl (E)-1-(4-(7-((3-(1-(tert-butoxycarbonyl)piperidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 1 (Step D) with methyl (E)-2-amino-1-(4-(2-amino-7-((3-(1-(tert-butoxycarbonyl)piperidin-3-yl)prop-2-yn-1-yl)oxy)-5-carbamoyl-1H-benzo[d]imidazol-1-yl)but-2-en-1-yl)-7-methoxy-1H-benzo[d]imidazole-5-carboxylate dihydrobromide and 1-ethyl-3-methyl-1H-pyrazole-5-carboxylic acid. The crude product was purified by column chromatography on $SiO_2$ (DCM:MeOH:$NH_4OH$=200:10:1 to 80:10:1) to afford the title compound as a light brown oil. LC-MS: m/z=959.4 [M+H]$^+$.

Step E: (E)-1-(4-(7-((3-(1-(tert-butoxycarbonyl)piperidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(7-((3-(1-(tert-butoxycarbonyl)piperidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2 -(1-ethyl-3-methyl-1H-pyrazole-5-carboxamido)-7-methoxy-1H-benzo[d]imidazole-5-carboxylate. The crude solid product was suspended in acetone/hexanes, washed with hexanes and dried under vacuum to afford the title compound as a light brown solid. LC-MS: m/z=945.3 [M+H]+.

Step F: tert-butyl (E)-3-(3-((5-carbamoyl-1-(4-(5-carbamoyl-2-(1-ethyl-3-methyl-1H-pyrazole-5-carboxamido)-7-methoxy-1H-benzo[d]imidazol-1-yl) but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate The title compound was prepared in a similar fashion to Example 3 with (E)-1-(4-(7-((3-(1-(tert-butoxycarbonyl)piperidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid. The crude product was purified by column chromatography on $SiO_2$ (DCM:MeOH:$NH_4OH$=200:10:1 to 80:10:1) to afford the title compound (0.1% for 6 steps) as a white solid. $^1$HNMR (400 MHz, DMSO-$d_6$): □□ 12.85 (2H, s), 7.97 (1H, s), 7.92 (1H, s), 7.65 (2H, d, J=6.0 Hz), 7.35 (3H, d, J=7.6 Hz), 7.27 (1H, s), 6.53 (2H, d, J=8.0 Hz), 5.91-5.82 (2H, m), 4.92 (4H, s), 4.65 (2H, s), 4.53 (4H, d, J=6.4 Hz), 3.64 (3H, s), 3.49-3.40 (1H, m), 2.89 (2H, t, J=10.2 Hz), 2.34-2.33 (1H, m), 2.11-2.10 (6H, m), 1.70-1.67 (1H, m), 1.44-1.43 (1H, m), 1.33 (9H, s), 1.27 (7H, t, J=6.8 Hz), 1.19-1.17 (1H, m). LC-MS: m/z=944.3 [M+H]+.

Example 33: (E)-1-(4-(5-carbamoyl-2-(1-ethyl-3-methyl-1H-pyrazole-5-carboxamido)-7-((4-hydroxy-4-methylpent-2-yn-1-yl)oxy)-1H-benzo[d]imidazol-1-yl)but-2-en-1-yl)-2-(1-ethyl-3-methyl-1H-pyrazole-5-carboxamido)-N,7-dimethoxy-1H-benzo[d]imidazole-5-carboxamide

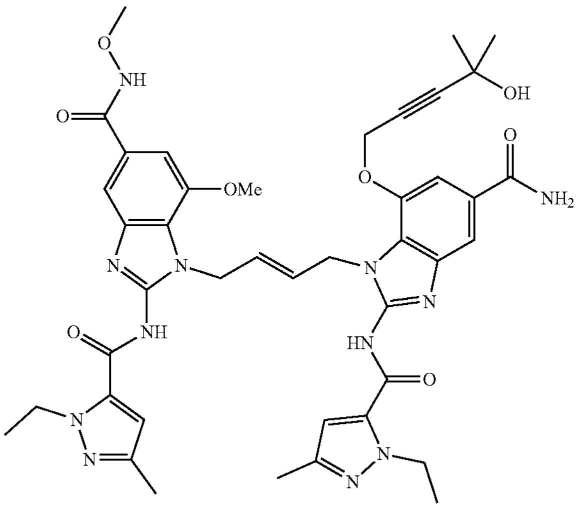 [SMILES: CCn1nc(C)cc1C(=O)Nc1nc2cc(C(=O)NOC)cc(OC)c2n1C/C=C/Cn1c(NC(=O)c2cc(C)nn2CC)nc2cc(C(N)=O)cc(OCC#CC(C)(C)O)c21]

Step A: methyl (E)-4-((4-((4-carbamoyl-2-((4-hydroxy-4-methylpent-2-yn-1-yl)oxy)-6-nitrophenyl) amino)but-2-en-1-yl)amino)-3-methoxy-5-nitrobenzoate The title compound was prepared in a similar fashion to Example 1 (Step A) with 4-chloro-3-((4-hydroxy-4-methylpent-2-yn-1-yl)oxy)-5-nitrobenzamide (Intermediate 16) and methyl (E)-4-((4-aminobut-2-en-1-yl)amino)-3-methoxy-5-nitrobenzoate hydrochloride (Intermediate 1). The crude product was purified by column chromatography on NH—$SiO_2$ (DCM:MeOH=97:3) to afford the title compound (36%) as an orange solid. $^1$H NMR (400 MHz, DMSO-$d_6$): δ 8.19 (1H, d, J=2.0 Hz), 8.10 (1H, d, J=1.6 Hz), 7.99-7.94 (2H, m), 7.77 (1H, t, J=6.0 Hz), 7.59 (1H, d, J=1.2 Hz), 7.34 (1H, d, J=1.6 Hz), 7.32 (1H, s), 5.60 (2H, q, J=4.0 Hz), 5.36 (1H, s), 4.78 (2H, s), 4.11-4.07 (4H, m), 3.83 (3H, s), 3.80 (3H, s), 1.32 (6H, s).

Step B: Methyl (E)-3-amino-4-((4-((2-amino-4-carbamoyl-6-((4-hydroxy-4-methylpent-2-yn-1-yl) oxy)phenyl)amino)but-2-en-1-yl)amino)-5-methoxy-benzoate The title compound was prepared in a similar fashion to Example 1 (Step B) with methyl (E)-4-((4-((4-carbamoyl-2-((4-hydroxy-4-methylpent-2-yn-1-yl)oxy)-6-nitrophenyl) amino)but-2-en-1-yl)amino)-3-methoxy-5-nitrobenzoate. The crude product was used for the next reaction without purification as a light brown solid. $^1$H NMR (400 MHz, DMSO-$d_6$): δ 7.53 (1H, brs), 7.01 (1H, d, J=1.6 Hz), 6.97 (1H, brs), 6.86 (1H, d, J=2.0 Hz), 6.85 (1H, d, J=2.0 Hz), 6.82 (1H, d, J=1.6 Hz), 5.68-5.66 (2H, m), 5.34 (1H, s), 4.79 (2H, s), 4.71-4.70 (4H, m), 3.76 (3H, s), 3.74 (3H, s), 3.62-3.58 (3H, m), 3.62-3.53 (3H, m), 1.34 (6H, s).

Step C: Methyl (E)-2-amino-1-(4-(2-amino-5-carbamoyl-7-((4-hydroxy-4-methylpent-2-yn-1-yl)oxy)-1H-benzo[d]imidazol-1-yl)but-2-en-1-yl)-7-methoxy-1H-benzo[d]imidazole-5-carboxylate 2HBr The title compound was prepared in a similar fashion to Example 1 (Step C) with methyl (E)-3-amino-4-((4-((2-amino-4-carbamoyl-6-((4-hydroxy-4-methylpent-2-yn-1-yl) oxy)phenyl)amino)but-2-en-1-yl)amino)-5-methoxybenzoate. The crude solid product was recrystallized from MeOH/$Et_2O$, washed with $Et_2O$ and dried under vacuum to afford the title compound (82%) as a light brown solid. $^1$H NMR (400 MHz, DMSO-$d_6$): δ 8.77-8.65 (4H, m), 8.03-7.95 (1H, m), 7.57 (1H, d, J=0.8 Hz), 7.51 (1H, s), 7.50 (1H, s), 7.48 (1H, s), 7.32 (1H, s), 5.84-5.78 (2H, m), 5.39 (1H, brs), 4.86-4.83 (6H, m), 3.87 (3H, s), 3.74 (3H, s), 1.31 (6H, s).

Step D: Methyl (E)-1-(4-(5-carbamoyl-2-(1-ethyl-3-methyl-1H-pyrazole-5-carboxamido)-7-((4-hydroxy-4-methylpent-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d] imidazole-5-carboxylate The title compound was prepared in a similar fashion to Example 1 (Step D) with methyl (E)-2-amino-1-(4-(2-amino-5-carbamoyl-7-((4-hydroxy-4-methylpent-2-yn-1-yl) oxy)-1H-benzo[d]imidazol-1-yl)but-2-en-1-yl)-7-methoxy-1H-benzo[d]imidazole-5-carboxylate 2HBr and 1-ethyl-3-methyl-1H-pyrazole-5-carboxylic acid. The residue was purified by column chromatography on $SiO_2$ (DCM: MeOH=95:5 to 90:10) to afford the title compound (66%) as a light brown solid. $^1$H NMR (400 MHz, DMSO-$d_6$): δ 7.89 (1H, brs), 7.75 (1H, s), 7.66 (1H, s), 7.40 (1H, s), 7.36 (1H, brs), 7.24 (1H, s), 6.54 (1H, s), 6.44 (1H, s), 5.89-5.83 (2H, m), 5.33 (1H, s), 4.92 (4H, d, J=5.2 Hz), 4.77 (2H, s), 4.55-4.46 (4H, m), 3.86 (3H, s), 3.65 (3H, s), 2.11 (3H, s), 2.08 (3H, s), 1.27-1.24 (12H, m).

Step E: (E)-1-(4-(5-carbamoyl-2-(1-ethyl-3-methyl-1H-pyrazole-5-carboxamido)-7-((4-hydroxy-4-methylpent-2-yn-1-yl)oxy)-1H-benzo[d]imidazol-1-yl)but-2-en-1-yl)-2-(1 -ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(5-carbamoyl-2-(1-ethyl-3-methyl-1H-pyrazole-5-carboxamido)-7-((4-hydroxy-4-methylpent-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate. The crude solid product was washed with water and dried under vacuum to afford the title compound (>99%) as a white solid. $^1$H NMR (400 MHz, DMSO-$d_6$): δ 7.90 (1H, brs), 7.74 (1H, s), 7.66 (1H, s), 7.42 (1H, s), 7.35 (1H, brs), 7.29 (1H, s), 6.52 (1H, s), 6.44 (1H, s), 5.94-5.81 (2H, m), 5.34 (1H, s), 4.93 (4H, d, J=3.6 Hz), 4.54-4.48 (4H, m), 3.70 (3H, s), 3.50 (3H, s), 2.10 (3H, s), 2.08 (3H, s), 1.27-1.22 (12H, m).

Step F: (E)-1-(4-(5-carbamoyl-2-(1-ethyl-3-methyl-1H-pyrazole-5-carboxamido)-7-((4-hydroxy-4-methylpent-2-yn-1-yl)oxy)-1H-benzo[d]imidazol-1-yl)but-2-en-1-yl)-2-(1-ethyl-3-methyl-1H-pyrazole-5-carboxamido)-N,7-dimethoxy-1H-benzo[d]imidazole-5-carboxamide The title compound was prepared in a similar fashion to Example 2 with (E)-1-(4-(5-carbamoyl-2-(1-ethyl-3-methyl-1H-pyrazole-5-carboxamido)-7-((4-hydroxy-4-methylpent-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid. The crude product was purified by prep-HPLC to afford the title compound (18%) as a white solid. $^1$H NMR (400 MHz, DMSO-$d_6$): δ 11.72 (1H, s), 7.91 (1H, brs), 7.66 (1H, s), 7.55 (1H, s), 7.41 (1H, s), 7.37 (1H, brs), 7.13 (1H, s), 6.52 (1H, s), 6.49 (1H, s), 5.90-5.82 (2H, m), 5.32 (1H, brs), 4.93-4.89 (4H, m), 4.80 (2H, s), 4.52-4.47 (4H, m), 3.72 (3H, s), 3.69 (3H, s), 2.10 (3H, s), 2.09 (3H, s), 1.27-1.25 (12H, m). LC-MS: m/z=849.3 [M+H]$^+$ Example 34: 2-(dimethylamino)ethyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)prop-1-yn-1-yl)piperidine-1-carboxylate

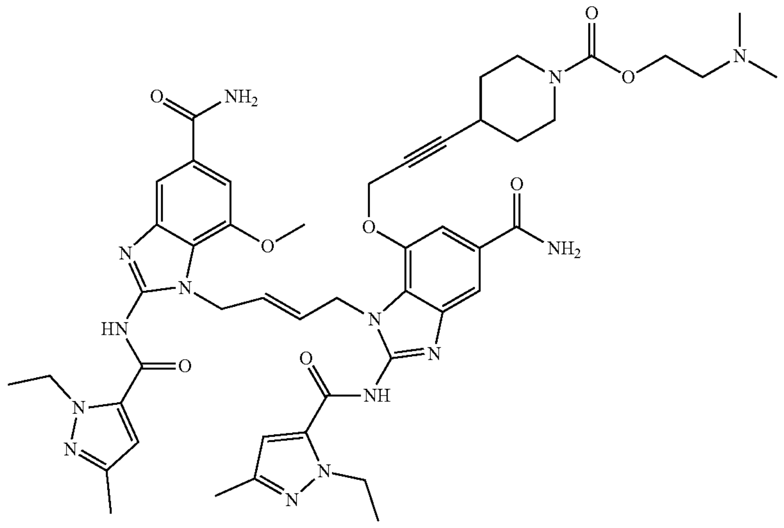 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC3CCN(C(=O)OCCN(C)C)CC3)c21]

To a solution of (E)-1-(4-(5-carbamoyl-2-(1-ethyl-3-methyl-1H-pyrazole-5-carboxamido)-7-((3-(piperidin-4-yl)prop-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 4, 25.0 mg, 0.0280 mmol) in DMF (0.28 mL) was added DIPEA (24.8 μL, 0.142 mmol) followed by 2-(dimethylamino)ethyl (4-nitrophenyl) carbonate hydrochloride (Intermediate 17, 9.08 mg, 0.0310 mmol) at room temperature. The reaction mixture was stirred at room temperature for 2 hours. After treatment with saturated aq. $NaHCO_3$ solution, a precipitated solid was collected by filtration. The solid was purified by column chromatography on $SiO_2$ (DCM:MeOH:$NH_4OH$=97:7:1) to afford the title compound (8.3 mg, 31%) as a light brown solid. $^1$H NMR (400 MHz, DMSO-$d_6$): δ 12.78 (2H, brs), 7.96 (1H, s), 7.89 (1H, s), 7.66 (2H, dd, J=4.2, 1.0 Hz), 7.37 (1H, s), 7.35 (2H, s), 7.29 (1H, s), 6.55 (1H, s), 6.53 (1H, s), 5.95-5.81 (2H, m), 4.91 (4H, s), 4.69 (2H, s), 4.53 (4H, q, J=6.8 Hz), 4.01 (2H, t, J=5.8 Hz), 3.67 (3H, s), 3.51-3.46 (2H, m), 2.98 (2H, t, J=9.8 Hz), 2.41 (2H, t, J=5.8 Hz), 2.12 (6H, s), 2.11 (3H, s), 2.10 (3H, s), 1.58-1.56 (2H, m), 1.32-1.24 (8H, m). LC-MS: m/z=959.2 [M+H]$^+$.

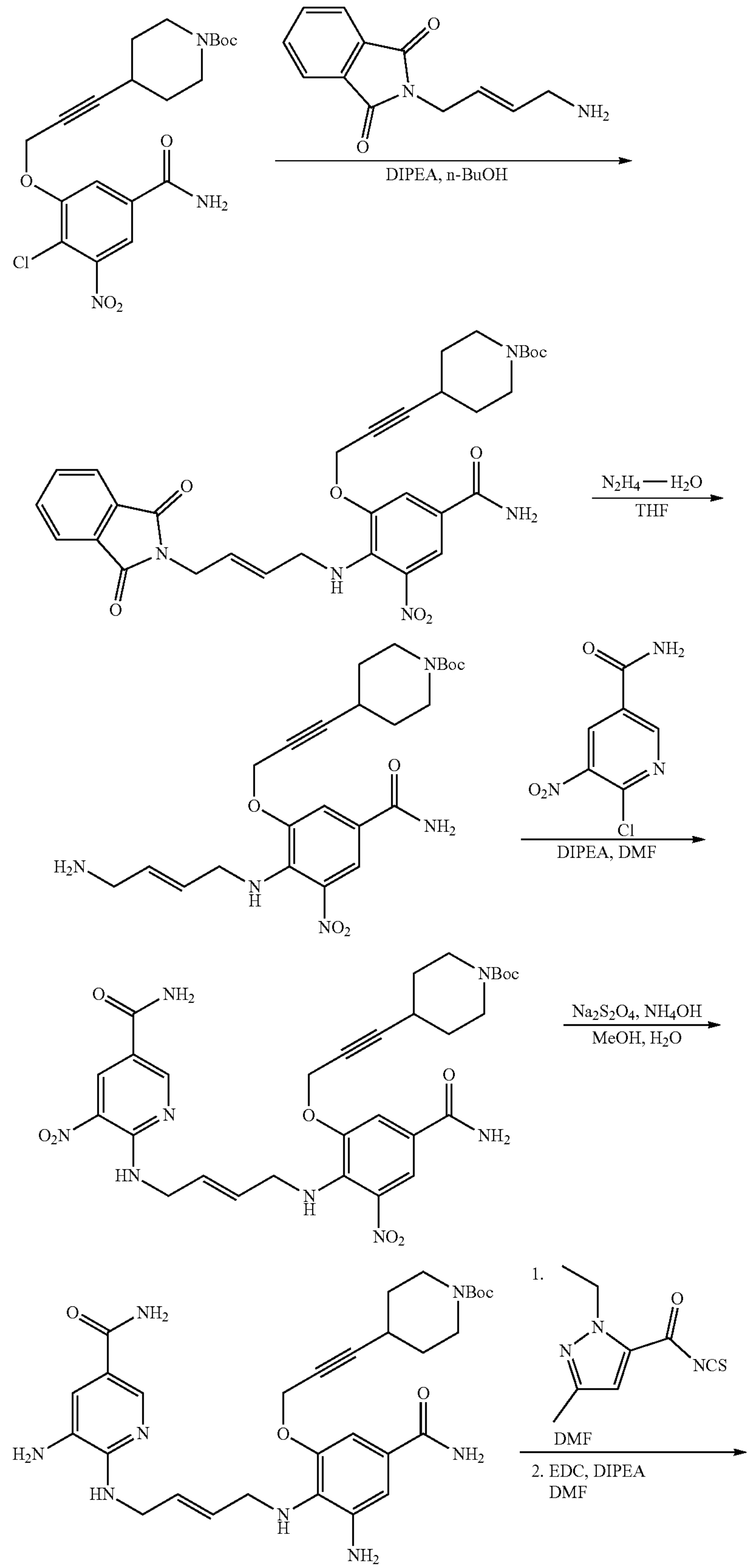
DIPEA, n-BuOH
$N_2H_4$—$H_2O$
THF
DIPEA, DMF
$Na_2S_2O_4$, $NH_4OH$
MeOH, $H_2O$
1.
DMF
2. EDC, DIPEA
DMF -continued

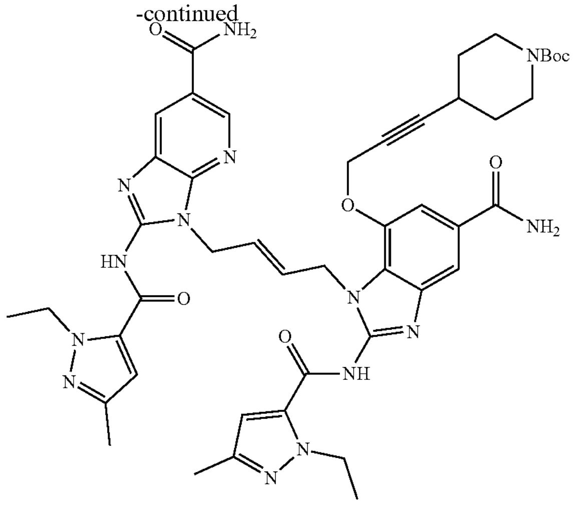

Example 35: methyl (E)-3-(4-(7-((3-(1-(tert-butoxycarbonyl)piperidin-4-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-3H-imidazo[4,5-b]pyridine-6-carboxylate

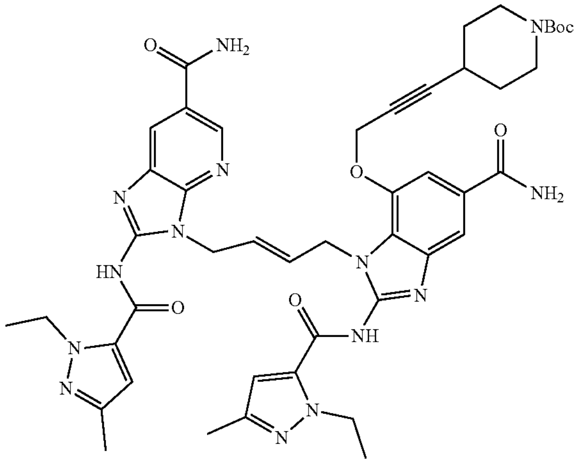 [SMILES: CCn1nc(C)cc1C(=O)Nc1nc2cc(C(N)=O)cnc2n1C/C=C/Cn1c(NC(=O)c2cc(C)nn2CC)nc2cc(C(N)=O)cc(OCC#CC3CCN(C(=O)OC(C)(C)C)CC3)c21]

Step A: tert-butyl (E)-4-(3-(5-carbamoyl-2-((4-(1,3-dioxoisoindolin-2-yl)but-2-en-1-yl)amino)-3-nitrophenoxy)prop-1-yn-1-yl)piperidine-1-carboxylate To a solution of tert-butyl 4-(3-(5-carbamoyl-2-chloro-3-nitrophenoxy)prop-1-yn-1-yl)piperidine-1-carboxylate (Intermediate 15, 1.00 g, 2.28 mmol) and (E)-2-(4-aminobut-2-en-1-yl)isoindoline-1,3-dione (Intermediate 2, 0.741 g, 3.43 mmol) in n-BuOH (11 mL) was added DIPEA (1.99 mL, 11.4 mmol) at room temperature. The reaction mixture was stirred at 140° C. overnight and then concentrated in vacuo to afford the title compound (0.320 g, 22%). $^1$H NMR (400 MHz, DMSO-$d_6$): δ 8.19 (1H, d, J=1.6 Hz), 7.95 (1H, brs), 7.88-7.82 (4H, m), 7.78 (1H, t, J=6.2 Hz), 7.65 (1H, d, J=2.0 Hz), 7.30 (1H, brs), 5.72-5.61 (2H, m), 4.84 (2H, d, J=1.2 Hz), 4.13-4.10 (4H, m), 3.46-3.39 (2H, m), 3.05 (2H, t, J=9.4 Hz), 2.62 (1H, s), 1.65-1.61 (2H, m), 1.37 (9H, s), 1.34-1.28 (2H, m).

Step B: tert-butyl (E)-4-(3-(2-((4-aminobut-2-en-1-yl)amino)-5-carbamoyl-3-nitrophenoxy)prop-1-yn-1-yl)piperidine-1-carboxylate To a solution of tert-butyl (E)-4-(3-(5-carbamoyl-2-((4-(1,3-dioxoisoindolin-2-yl)but-2-en-1-yl)amino)-3-nitrophenoxy)prop-1-yn-1-yl)piperidine-1-carboxylate (0.320 g, 0.518 mmol) in THF (2.9 mL) was added hydrazine hydrate (1.38 mL, 5.70 mmol) at room temperature. The reaction mixture was stirred at 60° C. for 1 hour. After concentration in vacuo, the residue was treated with 2 N aq. NaOH solution and then extracted with DCM twice. The combined organic layers were washed with brine, dried over $Na_2SO_4$, filtered, and concentrated in vacuo to afford the title compound (0.269 g, quant.) as a reddish foam. LC-MS: m/z=488.2 $[M+H]^+$.

Step C: tert-butyl (E)-4-(3-(5-carbamoyl-2-((4-((5-carbamoyl-3-nitropyridin-2-yl)amino)but-2-en-1-yl)amino)-3-nitrophenoxy)prop-1-yn-1-yl)piperidine-1-carboxylate To a solution of tert-butyl (E)-4-(3-(2-((4-aminobut-2-en-1-yl)amino)-5-carbamoyl-3-nitrophenoxy)prop-1-yn-1-yl)piperidine-1-carboxylate (269 mg, 0.552 mmol) in DMF (2.8 mL) was added DIPEA (0.549 mL, 3.14 mmol) and 6-chloro-5-nitronicotinamide (117 mg, 0.579 mmol). The reaction was stirred at room temperature for 1 hour. After treatment of saturated aq. $NaHCO_3$ solution, the mixture was extracted with DCM twice. The combined organic layers were washed with brine, dried over $Na_2SO_4$, filtered, and concentrated in vacuo. The residue was purified by column chromatography on $SiO_2$ (DCM only to DCM:MeOH=95:5) to afford the title compound (259 mg, 72%) as an orange solid. $^1$H NMR (400 MHz, DMSO-$d_6$): δ 8.89-8.85 (2H, m), 8.83 (1H, t, J=5.8 Hz), 8.21 (1H, d, J=1.2 Hz), 8.09 (1H, s), 7.96 (1H, s), 7.78 (1H, t, J=6.2 Hz), 7.67 (1H, d, J=2.0 Hz), 7.45 (1H, s), 7.30 (1H, s), 5.78-5.68 (2H, m), 4.86 (2H, s), 4.19 (2H, t, J=5.0 Hz), 4.14 (2H, t, J=5.4 Hz), 3.48-3.39 (2H, m), 3.09-3.05 (2H, m), 2.66-2.63 (1H, m), 1.67-1.62 (2H, m), 1.39-1.30 (11H, m).

Step D: tert-butyl (E)-4-(3-(3-amino-2-((4-((3-amino-5-carbamoylpyridin-2-yl)amino)but-2-en-1-yl)amino)-5-carbamoylphenoxy)prop-1-yn-1-yl)piperidine-1-carboxylate To a solution of tert-butyl (E)-4-(3-(5-carbamoyl-2-((4-((5-carbamoyl-3-nitropyridin-2-yl)amino)but-2-en-1-yl)amino)-3-nitrophenoxy)prop-1-yn-1-yl)piperidine-1-carboxylate (250 mg, 0.383 mmol) in MeOH (9.1 mL) was added $NH_4OH$ (2.98 mL, 19.2 mmol) followed by a solution of sodium hydrosulfite (800 mg, 4.60 mmol) in water (3.7 mL). The reaction mixture was stirred at room temperature for 1 hour. After concentration in vacuo, the residue was partitioned between water and EtOAc. The separated aqueous layer was extracted EtOAc. The combined organic layers were dried over $Na_2SO_4$, filtered, and concentrated in vacuo to afford the title compound (270 mg, quant.). LC-MS: m/z=593.2 $[M+H]^+$.

Step E: methyl (E)-3-(4-(7-((3-(1-(tert-butoxycarbonyl)piperidin-4-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-3H-imidazo[4,5-b]pyridine-6-carboxylate To a solution of tert-butyl (E)-4-(3-(3-amino-2-((4-((3-amino-5-carbamoylpyridin-2-yl)amino)but-2-en-1-yl)amino)-5-carbamoylphenoxy)prop-1-yn-1-yl)piperidine-1-carboxylate (248 mg, 0.418 mmol) in DMF (14 mL) was added 1-ethyl-3-methyl-1H-pyrazole-5-carbonyl isothiocyanate (Intermediate 3, 1.67 mL, 0.837 mmol) at 0° C. The mixture was stirred at room temperature for 1 hour. After addition of DIPEA (0.438 mL, 2.51 mmol) and EDC (321 mg, 1.67 mmol) in one portion, the reaction mixture was stirred at 70° C. for 1 hour and cooled to room temperature. After quenched with saturated aq. $NaHCO_3$ solution, the mixture was extracted with DCM twice. The combined organic layers were dried over $Na_2SO_4$, filtered, and concentrated in vacuo. The residual solid was suspended in EtOAc and filtered off. The filtrate was solidified from $Et_2O$/Hexanes. The solid was collected by filtration, washed with hexanes, and dried under vacuum to afford the title compound (34.0 mg, 8.8%) as a light brown solid. $^1H$ NMR (400 MHz, DMSO-$d_6$): δ 12.80 (2H, brs), 8.68 (1H, s), 8.12 (2H, s), 7.88 (1H, s), 7.65 (1H, s), 7.52 (1H, s), 7.40 (1H, s), 7.33 (1H, s), 6.52 (1H, s), 6.50 (1H, s), 5.93 (2H, s), 4.92 (2H, s), 4.78 (4H, s), 4.54-4.47 (4H, m), 3.45-3.39 (2H, m), 2.96 (2H, t, J=10.8 Hz), 2.46 (1H, s), 2.10 (3H, s), 2.09 (3H, s), 1.58-1.55 (2H, m), 1.34 (9H, s), 1.31-1.25 (8H, m). LC-MS: m/z=915.3 $[M+H]^+$.

Example 36: tert-butyl (E)-4-(4-((5-carbamoyl-2-(1-ethyl-3-methyl-1H-pyrazole-5-carboxamido)-1-(4-(2-(1-ethyl-3-methyl-1H-pyrazole-5-carboxamido)-7-methoxy-5-(methoxycarbamoyl)-1H-benzo[d]imidazol-1-yl)but-2-en-1-yl)-1H-benzo[d]imidazol-7-yl)oxy)but-2-yn-1-yl)piperazine-1-carboxylate

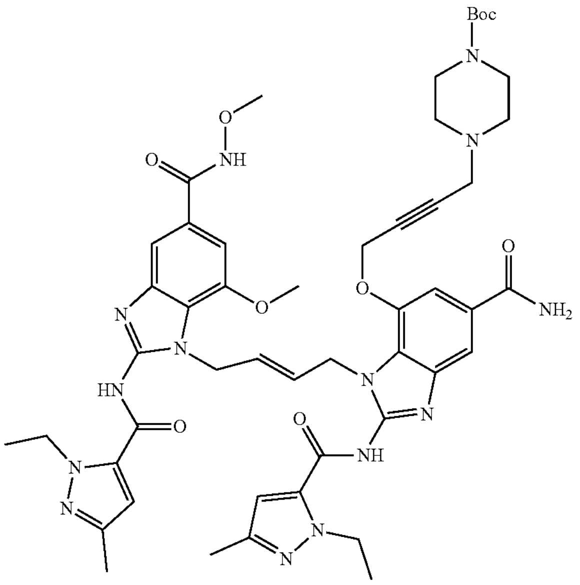 [SMILES: CCn1nc(C)cc1C(=O)Nc1nc2cc(C(=O)NOC)cc(OC)c2n1C/C=C/Cn1c(NC(=O)c2cc(C)nn2CC)nc2cc(C(N)=O)cc(OCC#CCN3CCN(C(=O)OC(C)(C)C)CC3)c21]

Step A: tert-butyl (E)-4-(4-(5-carbamoyl-2-((4-((2-methoxy-4-(methoxycarbonyl)-6-nitrophenyl)amino)but-2-en-1-yl)amino)-3-nitrophenoxy)but-2-yn-1-yl)piperazine-1-carboxylate The title compound was prepared in a similar fashion to Example 1 (Step A) with methyl (E)-4-((4-aminobut-2-en-1-yl)amino)-3-methoxy-5-nitrobenzoate hydrochloride (Intermediate 1, 0.989 g, 2.98 mmol) and tert-butyl 4-(4-(5-carbamoyl-2-chloro-3-nitrophenoxy)but-2-yn-1-yl)piperazine-1-carboxylate (Intermediate 18). The crude product was purified by column chromatography on $SiO_2$ (DCM:MeOH:$NH_4OH$=200:10:1) to afford the title compound (46%) as a reddish foam. $^1H$ NMR (400 MHz, DMSO-$d_6$): δ 8.18 (1H, d, J=1.8 Hz), 8.09 (1H, d, J=1.8 Hz), 7.96 (1H, t, J=6.4 Hz), 7.76 (1H, t, J=6.2 Hz), 7.60 (1H, d, J=1.8 Hz), 7.34 (1H, d, J=1.8 Hz), 7.31 (1H, s), 5.60-5.57 (2H, m), 4.84 (2H, s), 4.09-4.08 (4H, m), 3.84 (3H, s), 3.81 (3H, s), 3.30 (3Hm, s), 3.25 (4H, s), 2.31 (4H, s), 1.37 (9H, s). LC-MS: m/z=712.2 $[M+H]^+$.

Step B: tert-butyl (E)-4-(4-(3-amino-2-((4-((2-amino-6-methoxy-4-(methoxycarbonyl)phenyl)amino)but-2-en-1-yl)amino)-5-carbamoylphenoxy)but-2-yn-1-yl)piperazine-1-carboxylate The title compound was prepared in a similar fashion to Example 1 (Step B) with tert-butyl (E)-4-(4-(5-carbamoyl-2-((4-((2-methoxy-4-(methoxycarbonyl)-6-nitrophenyl)amino)but-2-en-1-yl)amino)-3-nitrophenoxy)but-2-yn-1-yl)piperazine-1-carboxylate. The crude product was used for the next reaction without purification as a light brown foam. LC-MS: m/z=652.2 $[M+H]^+$.

Step C: methyl (E)-2-amino-1-(4-(2-amino-7-((4-(4-(tert-butoxycarbonyl)piperazin-1-yl)but-2-yn-1-yl)oxy)-5-carbamoyl-1H-benzo[d]imidazol-1-yl)but-2-en-1-yl)-7-methoxy-1H-benzo[d]imidazole-5-carboxylate dihydrobromide The title compound was prepared in a similar fashion to Example 1 (Step C) with tert-butyl (E)-4-(4-(3-amino-2-((4-((2-amino-6-methoxy-4-(methoxycarbonyl)phenyl)amino)but-2-en-1-yl)amino)-5-carbamoylphenoxy)but-2-yn-1-yl)piperazine-1-carboxylate. The crude product was used for the next reaction without purification as a light brown solid. LC-MS: m/z=740.3 $[M+H]^+$.

Step D: methyl (E)-1-(4-(7-((4-(4-(tert-butoxycarbonyl)piperazin-1-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 1 (Step D) with methyl (E)-2-amino-1-(4-(2-amino-7-((4-(4-(tert-butoxycarbonyl) piperazin-1-yl)but-2-yn-1-yl)oxy)-5-carbamoyl-1H-benzo[d]imidazol-1-yl)but-2-en-1-yl)-7-methoxy-1H-benzo[d]imidazole-5-carboxylate dihydrobromide and 1-ethyl-3-methyl-1H-pyrazole-5-carboxylic acid. The crude product was purified by column chromatography on $SiO_2$ (DCM:MeOH:$NH_4OH$=200:10:1 to 80:10:1) to afford the title compound (27% for 4 steps) as a brown oil. LC-MS: m/z=974.3 $[M+H]^+$.

Step E: (E)-1-(4-(7-((4-(4-(tert-butoxycarbonyl)piperazin-1-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(7-((4-(4-(tert-butoxycarbonyl)piperazin-1-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate. The crude solid product was suspended in acetone, collected by filtration, washed with acetone, and dried under vacuum to afford the title compound as a white solid. LC-MS: m/z=960.4 $[M+H]^+$.

Step F: tert-butyl (E)-4-(4-((5-carbamoyl-2-(1-ethyl-3-methyl-1H-pyrazole-5-carboxamido)-1-(4-(2-(1-ethyl-3-methyl-1H-pyrazole-5-carboxamido)-7-methoxy-5-(methoxycarbamoyl)-1H-benzo[d]imidazol-1-yl)but-2-en-1-yl)-1H-benzo[d]imidazol-7-yl)oxy)but-2-yn-1-yl)piperazine-1-carboxylate The title compound was prepared in a similar fashion to Example 2 with (E)-1-(4-(7-((4-(4-(tert-butoxycarbonyl)piperazin-1-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid. The crude product was purified by column chromatography on $SiO_2$ (DCM:MeOH:$NH_4OH$=200:10:1 to 80:10:1) to afford the title compound (14% for 2 steps) as a white solid. $^1H$ NMR (400 MHz, DMSO-$d_6$): □□ 12.83 (2H, s), 11.73 (1H, s), 7.90 (1H, s), 7.67 (1H, s), 7.56 (1H, s), 7.37 (2H, s), 7.13 (1H, s), 6.53 (2H, s), 5.89-5.82 (2H, m), 4.90 (4H, d, J=3.2 Hz), 4.75 (2H, s), 4.53 (4H, q, J=6.8 Hz), 3.73 (3H, s), 3.68 (3H, s), 3.20 (4H, t, J=4.0 Hz), 3.17 (2H, s), 2.23 (4H, s), 2.10 (6H, d, J=2.0 Hz), 1.33 (9H, s), 1.28 (6H, t, J=6.8 Hz). LC-MS: m/z=989.4 $[M+H]^+$.

Example 37: tert-butyl 4-(4-(2-chloro-5-(methoxycarbonyl)-3-nitrophenoxy)but-2-yn-1-yl)piperazine-1-carboxylate

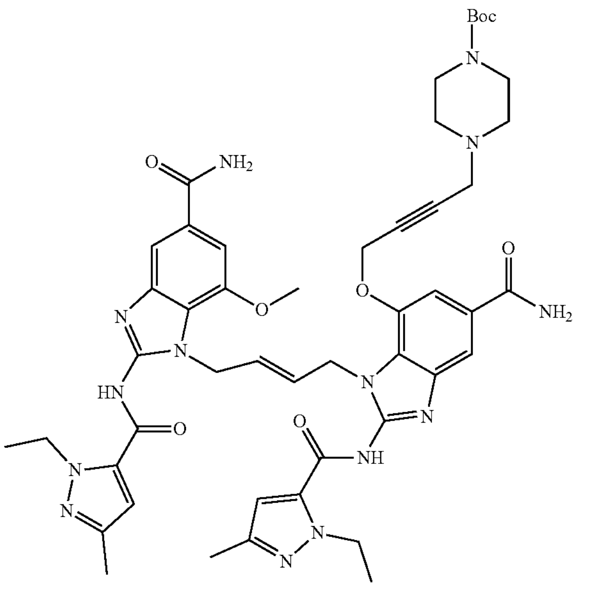 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCN3CCN(C(=O)OC(C)(C)C)CC3)c21]

The title compound was prepared in a similar fashion to Example 3 with (E)-1-(4-(7-((4-(4-(tert-butoxycarbonyl)piperazin-1-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid (Example 36, Step E). The crude product was purified by column chromatography on $SiO_2$ (DCM:MeOH:$NH_4OH$=200:10:1 to 80:10:1) to afford the title compound (8%) as a white solid. $^1H$ NMR (400 MHz, DMSO-$d_6$): □□ 7.97 (1H, s), 7.92 (1H, s), 7.67 (1H, s), 7.65 (1H, s), 7.38 (1H, s), 7.35 (2H, s), 7.29 (1H, s), 6.52 (2H, d, J=3.2 Hz), 5.89-5.79 (2H, m), 4.91 (4H, d, J=3.2 Hz), 4.76 (2H, s), 4.52 (4H, q, J=6.4 Hz), 3.70 (3H, s), 3.19-3.17 (6H, m), 2.23-2.21 (4H, m), 2.09 (6H, d, J=2.4 Hz), 1.33 (9H, s), 1.27 (6H, t, J=6.8 Hz). LC-MS: m/z=959.3 $[M+H]^+$.

Example 38: (E)-1-(4-(5-carbamoyl-2-(1-ethyl-3-methyl-1H-pyrazole-5-carboxamido)-7-((4-(4-(isopropoxycarbonyl)piperazin-1-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid

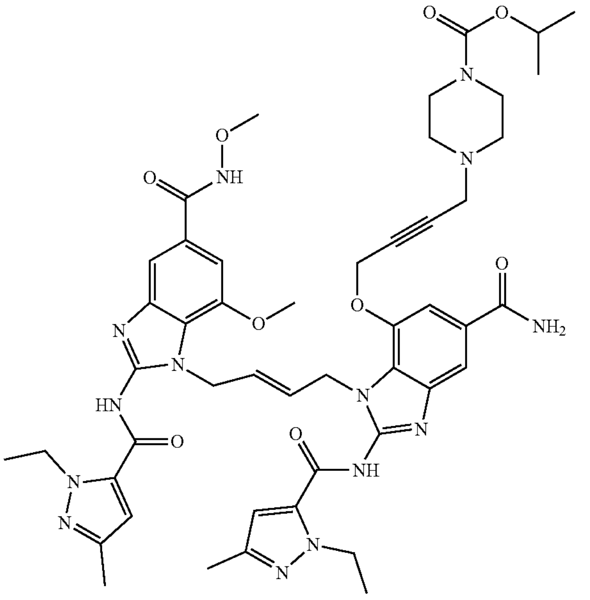 [SMILES: CCn1nc(C)cc1C(=O)Nc1nc2cc(C(=O)NOC)cc(OC)c2n1C/C=C/Cn1c(NC(=O)c2cc(C)nn2CC)nc2cc(C(N)=O)cc(OCC#CCN3CCN(C(=O)OC(C)C)CC3)c21]

Step A: isopropyl (E)-4-(4-(2-((4-((tert-butoxycarbonyl)amino)but-2-en-1-yl)amino)-5-carbamoyl-3-nitrophenoxy)but-2-yn-1-yl)piperazine-1-carboxylate To a solution of isopropyl 4-(4-(5-carbamoyl-2-chloro-3-nitrophenoxy)but-2-yn-1-yl)piperazine-1-carboxylate (Intermediate 19, 600 mg, 1.39 mmol) in DMSO (6.0 mL) was added DIPEA (1.40 mL, 8.04 mmol) and tert-butyl (E)-(4-aminobut-2-en-1-yl)carbamate (520 mg, 2.79 mmol) at room temperature. The reaction mixture was stirred at 120° C. for 3 hours in a sealed tube. After concentration in vacuo, the residue was dissolved in DCM and washed with saturated aq. $NaHCO_3$. The separated organic layer was washed with brine, dried over $Na_2SO_4$, filtered, and concentrated in vacuo. The residue was purified by column chromatography on NH—$SiO_2$ (DCM:MeOH=20:1) to give the title compound as a brown oil. LC-MS: m/z=589.2 $[M+H]^+$.

Step B: isopropyl (E)-4-(4-(2-((4-aminobut-2-en-1-yl)amino)-5-carbamoyl-3-nitrophenoxy)but-2-yn-1-yl)piperazine-1-carboxylate To a solution of isopropyl (E)-4-(4-(2-((4-((tert-butoxycarbonyl)amino)but-2-en-1 -yl)amino)-5-carbamoyl-3-nitrophenoxy)but-2-yn-1-yl)piperazine-1-carboxylate (800 mg, 1.36 mmol) in MeOH (11 mL) was added HCl (4 M in dioxane, 1.70 mL, 6.80 mmol) at 0° C. The reaction mixture was stirred at room temperature for 3 hours. After concentration in vacuo, the residue was diluted with EtOAc and basified with 2 N aq. NaOH until pH 9. The mixture was extracted with EtOAc twice. The combined organic layers were washed with brine, dried over $Na_2SO_4$, filtered, and concentrated in vacuo to give the title compound (582 mg, crude). LC-MS: m/z=489.2 $[M+H]^+$.

Step C: isopropyl (E)-4-(4-(5-carbamoyl-2-((4-((2-methoxy-4-(methoxycarbonyl)-6-nitrophenyl)amino)but-2-en-1-yl)amino)-3-nitrophenoxy)but-2-yn-1-yl)piperazine-1-carboxylate A mixture of isopropyl (E)-4-(4-(2-((4-aminobut-2-en-1-yl)amino)-5-carbamoyl-3-nitrophenoxy)but-2-yn-1-yl)piperazine-1-carboxylate (582 mg, 1.19 mmol), methyl 4-chloro-3-methoxy-5-nitrobenzoate (585 mg, 2.38 mmol) and DIPEA (1.00 mL, 5.74 mmol) in DMF (5.80 mL) was stirred at 100° C. for 3 hours in a sealed tube. After quenched with saturated aq. $NaHCO_3$ solution, the mixture was extracted with DCM twice. The combined organic layers were washed with brine, dried over $Na_2SO_4$, filtered, and concentrated in vacuo. The residue was purified by column chromatography on NH—$SiO_2$ (DCM:MeOH=50:1) to give the title compound (513 mg, 52% for 3 steps) as an orange solid. $^1H$ NMR (400 MHz, $CDCl_3$): δ 8.42 (1H, s), 8.13 (1H, s), 7.59 (1H, s), 7.43 (1H, s), 5.74 (2H, brs), 4.89 (1H, t, J=6.0 Hz), 4.78 (2H, s), 4.26 (4H, s), 3.91 (3H, s), 3.85 (3H, s), 3.44 (4H, s), 3.34 (2H, s), 2.40 (4H, s), 1.23 (6H, d, J=6.0 Hz).

Step D: isopropyl (E)-4-(4-(3-amino-2-((4-((2-amino-6-methoxy-4-(methoxycarbonyl)phenyl)amino)but-2-en-1-yl)amino)-5-carbamoylphenoxy)but-2-yn-1-yl)piperazine-1-carboxylate The title compound was prepared in a similar fashion to Example 1 (Step B) with isopropyl (E)-4-(4-(5-carbamoyl-2-((4-((2-methoxy-4-(methoxycarbonyl)-6-nitro-phenyl)amino)but-2-en-1-yl)amino)-3-nitrophenoxy)but-2-yn-1-yl)piperazine-1-carboxylate. The crude product was used for the next reaction without purification. LC-MS: m/z=638.2 $[M+H]^+$ Step E: methyl (E)-2-amino-1-(4-(2-amino-5-carbamoyl-7-((4-(4-(isopropoxycarbonyl)piperazin-1-yl)but-2-yn-1-yl)oxy)-1H-benzo[d]imidazol-1-yl)but-2-en-1-yl)-7-methoxy-1H-benzo[d]imidazole-5-carboxylate dihydrobromide The title compound was prepared in a similar fashion to Example 1 (Step C) with isopropyl (E)-4-(4-(3-amino-2-((4-((2-amino-6-methoxy-4-(methoxy-carbonyl)phenyl)amino)but-2-en-1-yl)amino)-5-carbamoylphenoxy)but-2-yn-1-yl)piperazine-1-carboxylate. The crude solid product was recrystallized from $Et_2O$/MeOH to give the title compound as a yellow solid. LC-MS: m/z=688.2 $[M+H]^+$.

Step F: methyl (E)-1-(4-(5-carbamoyl-2-(1-ethyl-3-methyl-1H-pyrazole-5-carboxamido)-7-((4-(4-(isopropoxycarbonyl)piperazin-1-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 1 (Step D) with methyl (E)-2-amino-1-(4-(2-amino-5-carbamoyl-7-((4-(4-(isopropoxycarbonyl)piperazin-1-yl)but-2-yn-1-yl)oxy)-1H-benzo[d]imidazol-1-yl) but-2-en-1-yl)-7-methoxy-1H-benzo[d]-imidazole-5-carboxylate dihydrobromide and 1-ethyl-3-methyl-1H-pyrazole-5-carboxylic acid. The crude product was purified by column chromatography on $SiO_2$ (DCM:MeOH:TEA=100:10:1) to give the title compound as a pale yellow solid. LC-MS: m/z=960.1 $[M+H]^+$.

Step G: (E)-1-(4-(5-carbamoyl-2-(1-ethyl-3-methyl-1H-pyrazole-5-carboxamido)-7-((4-(4-(isopropoxycarbonyl)piperazin-1-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(5-carbamoyl-2-(1-ethyl-3-methyl-1H-pyrazole-5-carboxamido)-7-((4-(4-(isopropoxycarbonyl)piperazin-1-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo [d]imidazole-5-carboxylate. The crude product was used for the next reaction without purification. LC-MS: m/z=946.1 $[M+H]^+$.

Step H: (E)-1-(4-(5-carbamoyl-2-(1-ethyl-3-methyl-1H-pyrazole-5-carboxamido)-7-((4-(4-(isopropoxycarbonyl)piperazin-1-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 2 with (E)-1-(4-(5-carbamoyl-2-(1-ethyl-3-methyl-1H-pyrazole-5-carboxamido)-7-((4-(4-(isopropoxycarbonyl)piperazin-1-yl)but-2-yn-1-yl)oxy)-1H-benzo[d]-imidazol-1-yl)but-2-en-1-yl)-2-(1-ethyl-3-methyl-1H-pyrazole-5-carboxamido)-7-methoxy-1H-benzo[d] imidazole-5-carboxylic acid. The crude product was purified by preparative TLC (NH—$SiO_2$) (DCM:MeOH=10:1) to give the title compound (6% for 5 steps) as a yellow solid. $^1H$ NMR (400 MHz, DMSO-$d_6$): δ 7.88 (1H, s), 7.64 (1H, s), 7.54 (1H, s), 7.34 (2H, brs), 7.10 (1H, s), 6.49 (2H, s), 5.90-5.79 (2H, m), 4.88-4.87 (5H, m), 4.74-4.72 (2H, m), 4.55-4.49 (4H, m), 3.72 (3H, s), 3.66 (3H, s), 3.57-3.56 (2H, m), 3.17 (2H, brs), 2.25-2.23 (4H, m), 2.09 (6H, s), 1.26-1.25 (6H, m), 1.11 (6H, d, J=6.4 Hz). LC-MS: m/z=975.2 $[M+H]^+$.

Example 39: (E)-1-(4-(5-carbamoyl-2-(1-ethyl-3-methyl-1H-pyrazole-5-carboxamido)-7-((4-(4-isobutyrylpiperazin-1-yl)but-2-yn-1-yl)oxy)-1H-benzo[d] imidazol-1-yl)but-2-en-1-yl)-2-(1-ethyl-3-methyl-1H-pyrazole-5-carboxamido)-N,7-dimethoxy-1H-benzo[d]imidazole-5-carboxamide

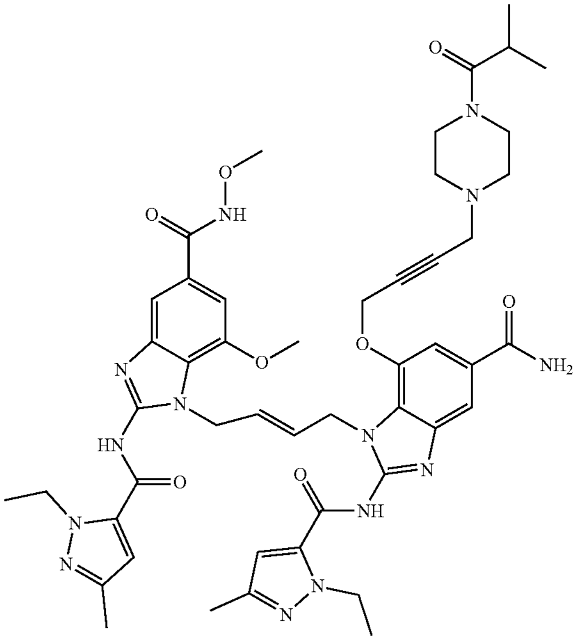 [SMILES: CCn1nc(C)cc1C(=O)Nc1nc2cc(C(=O)NOC)cc(OC)c2n1C/C=C/Cn1c(NC(=O)c2cc(C)nn2CC)nc2cc(C(N)=O)cc(OCC#CCN3CCN(C(=O)C(C)C)CC3)c21]

Step A: methyl (E)-4-((4-((4-carbamoyl-2-((4-(4-isobutyrylpiperazin-1-yl)but-2-yn-1-yl)oxy)-6-nitrophenyl)amino)but-2-en-1-yl)amino)-3-methoxy-5-nitrobenzoate (9) (K00803-022)

The title compound was prepared in a similar fashion to Example 1 (Step A) with methyl (E)-4-((4-aminobut-2-en-1-yl)amino)-3-methoxy-5-nitro benzoate hydrochloride (Intermediate 1) and 4-chloro-3-((4-(4-isobutyrylpiperazin-1-yl)but-2-yn-1-yl)oxy)-5-nitrobenzamide (Intermediate 20). The crude product was purified by column chromatography on $SiO_2$ (DCM:MeOH:$NH_4OH$=200:10:1) to afford the title compound (36%) as a reddish foam. $^1H$ NMR (400 MHz, DMSO-$d_6$): δ 8.18 (1H, d, J=1.6 Hz), 8.10 (1H, d, J=2.0 Hz), 7.97 (1H, t, J=6.8 Hz), 7.76 (1H, t, J=6.0 Hz), 7.60 (1H, d, J=2.0 Hz), 7.35 (1H, d, J=1.6 Hz), 5.59 (2H, dd, J=5.6, 4.4 Hz), 4.85 (2H, s), 4.09-4.08 (4H, m), 3.83 (3H, s), 3.81 (3H, s), 3.41 (6H, s), 2.84-2.76 (1H, m), 2.37 (2H, s), 2.32-2.31 (2H, m), 0.95 (6H, d, J=6.4 Hz). LC-MS: m/z=682.2 $[M+H]^+$.

Step B: methyl (E)-3-amino-4-((4-((2-amino-4-carbamoyl-6-((4-(4-isobutyrylpiperazin-1-yl)but-2-yn-1-yl)oxy)phenyl)amino)but-2-en-1-yl)amino)-5-methoxybenzoate The title compound was prepared in a similar fashion to Example 1 (Step B) with methyl (E)-4-((4-((4-carbamoyl-2-((4-(4-isobutyrylpiperazin-1-yl)but-2-yn-1-yl)oxy)-6-nitrophenyl)amino)but-2-en-1-yl)amino)-3-methoxy-5-nitrobenzoate. The crude product was used for the next reaction without purification as a light brown foam. LC-MS: m/z=622.3 [M+H]$^+$.

Step C: methyl (E)-2-amino-1-(4-(2-amino-5-carbamoyl-7-((4-(4-isobutyrylpiperazin-1-yl)but-2-yn-1-yl)oxy)-1H-benzo[d]imidazol-1-yl)but-2-en-1-yl)-7-methoxy-1H-benzo[d]imidazole-5-carboxylate dihydrobromide The title compound was prepared in a similar fashion to Example 1 (Step C) with methyl (E)-3-amino-4-((4-((2-amino-4-carbamoyl-6-((4-(4-isobutyrylpiperazin-1-yl)but-2-yn-1-yl)oxy)phenyl)amino)but-2-en-1-yl)amino)-5-methoxybenzoate. The crude product was used for the next reaction without purification as a light brown solid. LC-MS: m/z=672.2 [M+H]$^+$.

Step D: methyl (E)-1-(4-(5-carbamoyl-2-(1-ethyl-3-methyl-1H-pyrazole-5-carboxamido)-7-((4-(4-isobutyrylpiperazin-1-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 1 (Step D) with methyl (E)-2-amino-1-(4-(2-amino-5-carbamoyl-7-((4-(4-isobutyrylpiperazin-1-yl)but-2-yn-1-yl)oxy)-1H-benzo[d]imidazol-1-yl)but-2-en-1-yl)-7-methoxy-1H-benzo[d]imidazole-5-carboxylate dihydrobromide and 1-ethyl-3-methyl-1H-pyrazole-5-carboxylic acid. The crude product was purified by column chromatography on $SiO_2$ (DCM:MeOH:$NH_4OH$=200:10:1 to 80:10:1) to afford the title compound as a brown oil. LC-MS: m/z=944.2 [M+H]$^+$.

Step E: (E)-1-(4-(5-carbamoyl-2-(1-ethyl-3-methyl-1H-pyrazole-5-carboxamido)-7-((4-(4-isobutyrylpiperazin-1-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(5-carbamoyl-2-(1-ethyl-3-methyl-1H-pyrazole-5-carboxamido)-7-((4-(4-isobutyrylpiperazin-1-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate. The crude product was used for the next reaction without purification as a light brown solid. LC-MS: m/z=930.4 [M+H]$^+$.

Step F: (E)-1-(4-(5-carbamoyl-2-(1-ethyl-3-methyl-1H-pyrazole-5-carboxamido)-7-((4-(4-isobutyrylpiperazin-1-yl)but-2-yn-1-yl)oxy)-1H-benzo[d]imidazol-1-yl)but-2-en-1-yl)-2-(1-ethyl-3-methyl-1H-pyrazole-5-carboxamido)-N,7-dimethoxy-1H-benzo[d]imidazole-5-carboxamide The title compound was prepared in a similar fashion to Example 2 with (E)-1-(4-(5-carbamoyl-2-(1-ethyl-3-methyl-1H-pyrazole-5-carboxamido)-7-((4-(4-isobutyrylpiperazin-1-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid. The crude product was purified by column chromatography on $SiO_2$ (DCM:MeOH:$NH_4OH$=200:10:1 to 80:10:1) to afford the title compound (4% for 6 steps) as a white solid. $^1$H NMR (400 MHz, DMSO-$d_6$): □□ 7.90 (1H, s), 7.67 (1H, s), 7.57 (1H, s), 7.38 (2H, s), 7.15 (1H, s), 6.54 (2H, s), 5.90-5.83 (2H, m), 4.89 (4H, s), 4.75 (2H, s), 4.54 (4H, q, J=6.8 Hz), 3.73 (3H, s), 3.69 (3H, s), 3.19 (2H, s), 2.66 (1H, q, J=6.4 Hz), 2.23 (4H, s), 2.10 (6H, d, J=2.4 Hz), 1.28 (6H, t, J=6.8 Hz), 0.89 (6H, d, J=6.8 Hz). LC-MS: m/z=959.3 [M+H]$^+$.

Example 40: (E)-1-(4-(5-carbamoyl-2-(1-ethyl-3-methyl-1H-pyrazole-5-carboxamido)-7-((4-morpholinobut-2-yn-1-yl)oxy)-1H-benzo[d]imidazol-1-yl)but-2-en-1-yl)-2-(1-ethyl-3-methyl-1H-pyrazole-5-carboxamido)-N,7-dimethoxy-1H-benzo[d]imidazole-5-carboxamide

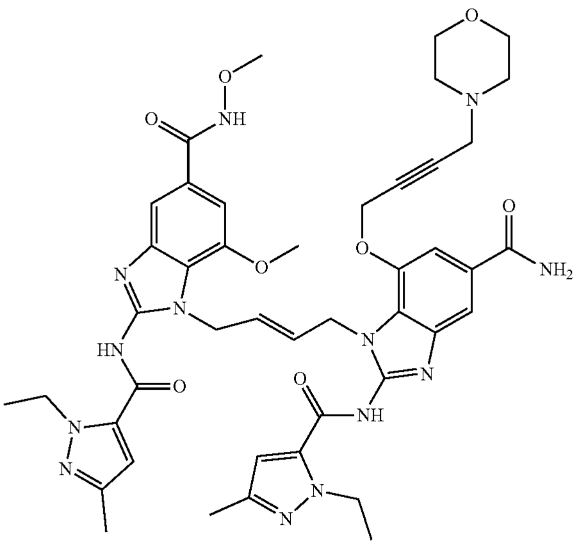 [SMILES: CCn1nc(C)cc1C(=O)Nc1nc2cc(C(=O)NOC)cc(OC)c2n1C/C=C/Cn1c(NC(=O)c2cc(C)nn2CC)nc2cc(C(N)=O)cc(OCC#CCN3CCOCC3)c21]

Step A: methyl (E)-4-((4-((4-carbamoyl-2-((4-morpholinobut-2-yn-1-yl)oxy)-6-nitrophenyl)amino)but-2-en-1-yl)amino)-3-methoxy-5-nitrobenzoate The title compound was prepared in a similar fashion to Example 1 (Step A) with methyl (E)-4-((4-aminobut-2-en-1-yl)amino)-3-methoxy-5-nitrobenzoate hydrochloride (Intermediate 1) and 4-chloro-3-((4-morpholinobut-2-yn-1-yl)oxy)-5-nitrobenzamide (Intermediate 21). The crude product was purified by column chromatography on NH—$SiO_2$ (DCM:MeOH=97:3) followed by on $SiO_2$ (DCM:MeOH:$NH_4OH$=95:5:0.1) to afford the title compound (30%) as an orange solid. $^1$H NMR (400 MHz, DMSO-$d_6$): δ 8.15 (1H, d, J=2.0 Hz), 8.06 (1H, d, J=2.0 Hz), 7.95-7.90 (2H, m), 7.72 (1H, t, J=6.0 Hz), 7.58 (1H, s), 7.31 (1H, s), 7.29 (1H, brs), 5.56 (2H, s), 4.82 (2H, s), 4.06 (4H, s), 3.79 (3H, s), 3.77 (3H, s), 3.47 (4H, d, J= 4.4 Hz), 3.23 (2H, s), 2.30 (4H, s).

Step B: methyl (E)-3-amino-4-((4-((2-amino-4-carbamoyl-6-((4-morpholinobut-2-yn-1-yl)oxy)phenyl)amino)but-2-en-1-yl)amino)-5-methoxybenzoate The title compound was prepared in a similar fashion to Example 1 (Step B) with methyl (E)-4-((4-((4-carbamoyl-2-((4-morpholinobut-2-yn-1-yl)oxy)-6-nitrophenyl)amino)

but-2-en-1-yl)amino)-3-methoxy-5-nitrobenzoate. The crude product was used for the next reaction without purification as a light brown solid. LC-MS: m/z=553.2 $[M+H]^+$.

Step C: methyl (E)-2-amino-1-(4-(2-amino-5-carbamoyl-7-((4-morpholinobut-2-yn-1-yl)oxy)-1H-benzo[d]imidazol-1-yl)but-2-en-1-yl)-7-methoxy-1H-benzo[d]imidazole-5-carboxylate dihydrobromide The title compound was prepared in a similar fashion to Example 1 (Step C) with methyl (E)-3-amino-4-((4-((2-amino-4-carbamoyl-6-((4-morpholinobut-2-yn-1-yl)oxy)phenyl)amino)but-2-en-1-yl)amino)-5-methoxybenzoate. The crude product was purified by recrystallization from $Et_2O$/MeOH, collected by filtration, washed with $Et_2O$ and dried under vacuum to afford the title compound (95%) as a light brown solid. LC-MS: m/z=603.1 $[M+H]^+$.

Step D: methyl (E)-1-(4-(5-carbamoyl-2-(1-ethyl-3-methyl-1H-pyrazole-5-carboxamido)-7-((4-morpholinobut-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 1 (Step D) with methyl (E)-2-((12-bromanyl)-14-azanyl)-1-(4-(2-((12-bromanyl)-14-azanyl)-5-carbamoyl-7-((4-morpholinobut-2-yn-1-yl)oxy)-1H-benzo[d]imidazol-1-yl)but-2-en-1-yl)-7-methoxy-1H-benzo[d]imidazole-5-carboxylate and 1-ethyl-3-methyl-1H-pyrazole-5-carboxylic acid. The crude product was purified by column chromatography on $SiO_2$ (DCM:MeOH:$NH_4OH$=95:5:0.1) to afford the title compound (11%) as a brown solid. LC-MS: m/z=875.2 $[M+H]^+$.

Step E: (E)-1-(4-(5-carbamoyl-2-(1-ethyl-3-methyl-1H-pyrazole-5-carboxamido)-7-((4-morpholinobut-2-yn-1-yl)oxy)-1H-benzo[d]imidazol-1-yl)but-2-en-1-yl)-2-(1-ethyl-3 -methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(5-carbamoyl-2-(1-ethyl-3-methyl-1H-pyrazole-5-carboxamido)-7-((4-morpholinobut-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate. The crude product was used for the next reaction without purification as a light brown solid. LC-MS: m/z=861.3 $[M+H]^+$.

Step F: (E)-1-(4-(5-carbamoyl-2-(1-ethyl-3-methyl-1H-pyrazole-5-carboxamido)-7-((4-morpholinobut-2-yn-1-yl)oxy)-1H-benzo[d]imidazol-1-yl)but-2-en-1-yl)-2-(1-ethyl-3-methyl-1H-pyrazole-5-carboxamido)-N,7-dimethoxy-1H-benzo[d]imidazole-5-carboxamide The title compound was prepared in a similar fashion to Example 2 with (E)-1-(4-(5-carbamoyl-2-(1-ethyl-3-methyl-1H-pyrazole-5-carboxamido)-7-((4-morpholinobut-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid. The crude product was purified by column chromatography on $SiO_2$ (DCM:MeOH:$NH_4OH$=93:7:0.1 to 90:10:0.1) followed by recrystallization from Hexanes/acetone to afford the title compound (4%) as a white solid. $^1H$ NMR (400 MHz, DMSO-$d_6$): δ 12.79 (2H, brs), 11.73 (1H, brs), 7.90 (1H, s), 7.66 (1H, s), 7.56 (1H, s), 7.40 (1H, s), 7.37 (1H, s), 7.13 (1H, s), 6.53 (2H, s), 5.88-5.84 (2H, m), 4.91 (4H, s), 4.78 (2H, s), 4.52 (4H, q, J=6.8 Hz), 3.73 (3H, s), 3.68 (3H, s), 3.48-3.45 (4H, m), 3.13 (2H, s), 2.27 (4H, s), 2.10 (6H, s), 1.29-1.23 (6H, m). LC-MS: m/z=890.3 $[M+H]^+$.

Example 41: tert-butyl (E)-4-(5-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-2-methylpent-3-yn-2-yl)piperazine-1-carboxylate

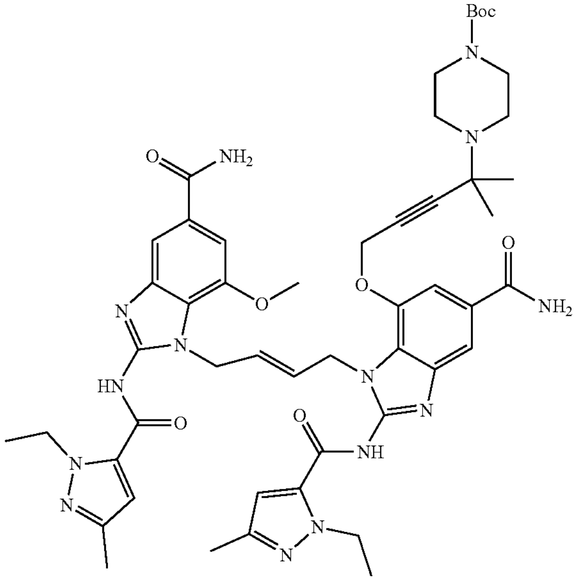 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CC(C)(C)N3CCN(C(=O)OC(C)(C)C)CC3)c21]

Step A: tert-butyl (E)-4-(5-(5-carbamoyl-2-((4-((2-methoxy-4-(methoxycarbonyl)-6-nitrophenyl)amino)but-2-en-1-yl)amino)-3-nitrophenoxy)-2-methylpent-3-yn-2-yl)piperazine-1-carboxylate The title compound was prepared in a similar fashion to Example 1 (Step A) with tert-butyl 4-(5-(5-carbamoyl-2-chloro-3-nitrophenoxy)-2-methylpent-3-yn-2-yl)piperazine-1-carboxylate (Intermediate 1) and methyl (E)-4-((4-aminobut-2-en-1-yl)amino)-3-methoxy-5-nitrobenzoate hydrochloride (Intermediate 22). The crude product was purified by column chromatography on NH—$SiO_2$ (DCM only to DCM:MeOH=98:2) to afford the title compound (>99%) as an orange solid. LC-MS: m/z=740.3 $[M+H]^+$.

Step B: tert-butyl (E)-4-(5-(3-amino-2-((4-((2-amino-6-methoxy-4-(methoxycarbonyl)phenyl)amino)but-2-en-1-yl)amino)-5-carbamoylphenoxy)-2-methylpent-3-yn-2-yl)piperazine-1-carboxylate The title compound was prepared in a similar fashion to Example 1 (Step B) with tert-butyl (E)-4-(5-(5-carbamoyl-2-((4-((2-methoxy-4-(methoxycarbonyl)-6-nitrophenyl)

amino)but-2-en-1-yl)amino)-3-nitrophenoxy)-2-methylpent-3-yn-2-yl)piperazine-1-carboxylate. The crude product was used for the next reaction without purification as a light brown solid. LC-MS: m/z=680.3 $[M+H]^+$.

Step C: methyl (E)-2-amino-1-(4-(2-amino-7-((4-(4-(tert-butoxycarbonyl)piperazin-1-yl)-4-methylpent-2-yn-1-yl)oxy)-5-carbamoyl-1H-benzo[d]imidazol-1-yl)but-2-en-1-yl)-7-methoxy-1H-benzo[d]imidazole-5-carboxylate The title compound was prepared in a similar fashion to Example 1 (Step C) with tert-butyl (E)-4-(5-(3-amino-2-((4-((2-amino-6-methoxy-4-(methoxycarbonyl)phenyl)amino)but-2-en-1-yl)amino)-5-carbamoylphenoxy)-2-methylpent-3-yn-2-yl)piperazine-1-carboxylate. The crude product was used for the next reaction without purification as a light brown solid. LC-MS: m/z=730.3 $[M+H]^+$.

Step D: methyl (E)-1-(4-(7-((4-(4-(tert-butoxycarbonyl)piperazin-1-yl)-4-methylpent-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 1 (Step D) with methyl (E)-2-((12-bromanyl)-14-azanyl)-1-(4-(2-((12-bromanyl)-14-azanyl)-7-((4-(4-(tert-butoxycarbonyl)piperazin-1-yl)-4-methylpent-2-yn-1-yl)oxy)-5-carbamoyl-1H-benzo[d]imidazol-1-yl)but-2-en-1-yl)-7-methoxy-1H-benzo[d]imidazole-5-carboxylate and 1-ethyl-3-methyl-1H-pyrazole-5-carboxylic acid. The crude product was purified by column chromatography on $SiO_2$ (DCM:MeOH:$NH_4OH$=95:5:0.1) to afford the title compound (7% for 4 steps) as a brown solid. $^1H$ NMR (400 MHz, DMSO-$d_6$): δ 12.85 (2H, s), 7.88 (1H, s), 7.76 (1H, d, J=1.2 Hz), 7.67 (1H, s), 7.36 (2H, s), 7.23 (1H, d, J=1.6 Hz), 6.56 (1H, s), 6.47 (1H, s), 5.88-5.79 (2H, m), 4.90 (4H, d, J=4.8 Hz), 4.74 (2H, s), 4.56-4.49 (4H, m), 3.86 (3H, s), 3.65 (3H, s), 3.17 (4H, s), 2.31 (4H, s), 2.11 (3H, s), 2.09 (3H, s), 1.32 (9H, s), 1.28 (6H, q, J=7.1 Hz), 1.19 (6H, s).

Step E: (E)-1-(4-(7-((4-(4-(tert-butoxycarbonyl)piperazin-1-yl)-4-methylpent-2-yn-1-yl)oxy)-5-carbamoyl-2-(1-ethyl-3-methyl-1H-pyrazole-5-carboxamido)-1H-benzo[ d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(7-((4-(4-(tert-butoxycarbonyl)piperazin-1-yl)-4-methylpent-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate. The crude product was used for the next reaction without purification as a light brown solid. $^1H$ NMR (400 MHz, DMSO-$d_6$): δ 12.87 (1H, s), 12.85 (1H, s), 7.90 (1H, s), 7.76 (1H, d, J=0.8 Hz), 7.67 (1H, s), 7.40 (1H, s), 7.36 (1H, s), 7.29 (1H, d, J=0.8 Hz), 6.54 (1H, s), 6.47 (1H, s), 5.94-5.80 (2H, m), 4.91 (4H, s), 4.79 (2H, s), 4.58-4.49 (4H, m), 3.70 (3H, s), 3.16 (4H, s), 2.31 (4H, s), 2.10 (3H, s), 2.08 (3H, s), 1.32 (9H, s), 1.30-1.25 (6H, m), 1.18 (6H, s).

Step F: tert-butyl (E)-4-(5-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-2-methylpent-3-yn-2-yl)piperazine-1-carboxylate The title compound was prepared in a similar fashion to Example 3 with (E)-1-(4-(7-((4-(4-(tert-butoxycarbonyl)piperazin-1-yl)-4-methylpent-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-H-benzo[d]imidazole-5-carboxylic acid. The crude product was purified by column chromatography on NH—$SiO_2$ (DCM:MeOH=93:7) to afford the title compound (61% for 2 steps) as a white solid. $^1H$ NMR (400 MHz, DMSO-$d_6$): δ 12.83 (2H, s), 7.97 (1H, s), 7.91 (1H, s), 7.67 (1H, s), 7.65 (1H, s), 7.40 (1H, s), 7.36 (2H, s), 7.29 (1H, d, J=0.8 Hz), 6.53 (1H, s), 6.52 (1H, s), 5.97-5.81 (2H, m), 4.91 (4H, s), 4.78 (2H, s), 4.53 (4H, d, J=6.8 Hz), 3.70 (3H, s), 3.17 (4H, s), 2.31 (4H, s), 2.10 (3H, s), 2.09 (3H, s), 1.32 (9H, s), 1.27 (6H, td, J=6.1, 4.5 Hz), 1.18 (6H, s). LC-MS: m/z=987.5 $[M+H]^+$.

Example 42: tert-butyl (E)-4-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidine-1-carboxylate

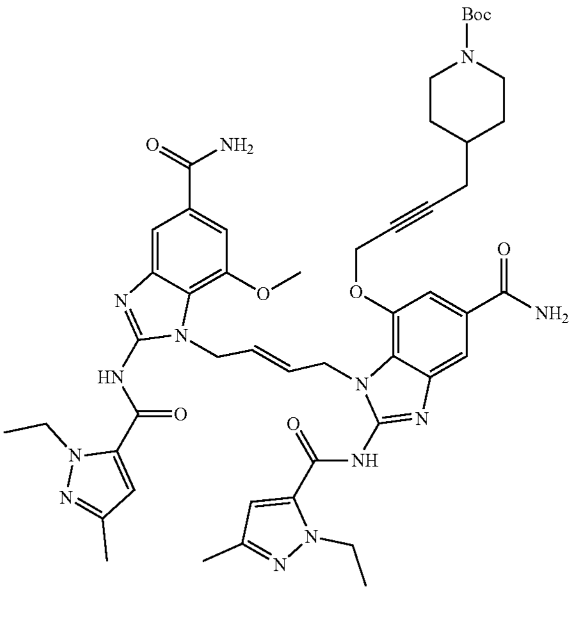 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCC3CCN(C(=O)OC(C)(C)C)CC3)c21]

Step A: tert-butyl (E)-4-(4-(5-carbamoyl-2-((4-(1,3-dioxoisoindolin-2-yl)but-2-en-1-yl)amino)-3-nitrophenoxy)but-2-yn-1-yl)piperidine-1-carboxylate A mixture of isopropyl 4-(4-(5-carbamoyl-2-chloro-3-nitrophenoxy)but-2-yn-1-yl)piperazine-1-carboxylate (Intermediate 23, 650 mg, 1.43 mmol), tert-butyl (E)-(4-aminobut-2-en-1-yl)carbamate (Intermediate 2, 467 mg, 2.15 mmol) and DIPEA (1.30 mL, 7.46 mmol) in n-BuOH (6.5 mL) was subjected to microwave irradiation at 120° C. for 3 hours. The reaction mixture was concentrated in vacuo to give the title compound (909 mg, crude) as a brown oil. LC-MS: m/z=632.2 $[M+H]^+$.

Step B: tert-butyl (E)-4-(4-(2-((4-aminobut-2-en-1-yl)amino)-5-carbamoyl-3-nitrophenoxy)but-2-yn-1-yl)piperidine-1-carboxylate A mixture of tert-butyl (E)-4-(4-(5-carbamoyl-2-((4-(1,3-dioxoisoindolin-2-yl)but-2-en-1-yl)amino)-3-nitrophenoxy) but-2-yn-1-yl)piperidine-1-carboxylate (1.60 g, 2.53 mmol) and hydrazine monohydrate (6.80 mL, 28.0 mmol) in THF (14.0 mL) was stirred at 60° C. for 1 hour. After concentration in vacuo, the residue was diluted with 2 N aq. NaOH and then extracted with DCM. The separated organic layer was washed with brine, dried over $Na_2SO_4$, filtered, and concentrated in vacuo to give the title compound (1.20 g, crude) as a reddish foam. LC-MS: m/z=502.2 $[M+H]^+$.

Step C: tert-butyl (E)-4-(4-(5-carbamoyl-2-((4-((2-methoxy-4-(methoxycarbonyl)-6-nitrophenyl)amino) but-2-en-1-yl)amino)-3-nitrophenoxy)but-2-yn-1-yl) piperidine-1-carboxylate A mixture of tert-butyl (E)-4-(4-(2-((4-aminobut-2-en-1-yl)amino)-5-carbamoyl-3-nitrophenoxy)but-2-yn-1-yl)piperidine-1-carboxylate (1.20 g, 2.39 mmol), methyl 4-chloro-3-methoxy-5-nitrobenzoate (1.18 g, 4.80 mmol) and DIPEA (2.10 mL, 12.06 mmol) in DMF (11 mL) was stirred at 100° C. for 2 hours. After quenched with saturated aq. $NaHCO_3$ solution, the mixture was extracted with DCM twice. The combined organic layers were washed with brine, dried over $Na_2SO_4$, filtered, and concentrated in vacuo. The residue was purified by column chromatography on NH—$SiO_2$ (DCM:MeOH=50:1) to give the title compound (770 mg, 43% for 3 steps) as an orange foam. $^1$H NMR (400 MHz, $CDCl_3$): δ 8.42 (1H, d, J=1.6 Hz), 8.12 (1H, d, J=2.0 Hz), 8.10-8.09 (2H, m), 7.59 (1H, d, J=2.0 Hz), 7.42 (1H, d, J=2.0 Hz), 5.80-5.67 (2H, m), 4.73 (2H, d, J=2.0 Hz), 4.29-4.24 (4H, m), 3.91 (3H, s), 3.84 (3H, s), 3.60 (2H, brs), 3.17-3.10 (2H, m), 2.60 (1H, brs), 1.76-1.71 (2H, m), 1.55-1.50 (2H, m), 1.44 (9H, s).

Step D: tert-butyl (E)-4-(4-(3-amino-2-((4-((2-amino-6-methoxy-4-(methoxycarbonyl)phenyl) amino)but-2-en-1-yl)amino)-5-carbamoylphenoxy) but-2-yn-1-yl)piperidine-1-carboxylate The title compound was prepared in a similar fashion to Example 1 (Step B) with tert-butyl (E)-4-(4-(5-carbamoyl-2-((4-((2-methoxy-4-(methoxycarbonyl)-6-nitro-phenyl) amino)but-2-en-1-yl)amino)-3-nitrophenoxy)but-2-yn-1-yl) piperidine-1-carboxylate. The crude product was used for the next reaction without purification as a pale brown foam. LC-MS: m/z=651.2 $[M+H]^+$.

Step E: methyl (E)-1-(4-(7-((4-(1-(tert-butoxycarbonyl)piperidin-4-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7 -methoxy-1H-benzo[d]imidazole-5-carboxylate The title compound was prepared in a similar fashion to Example 35 (Step E) with tert-butyl (E)-4-(4-(3-amino-2-((4-((2-amino-6-methoxy-4-(methoxycarbonyl)phenyl) amino)but-2-en-1-yl)amino)-5-carbamoylphenoxy)but-2-yn-1-yl)piperidine-1-carboxylate and 1-ethyl-3-methyl-1H-pyrazole-5-carbonyl isothiocyanate (Intermediate 3). The crude product was purified by column chromatography on NH—$SiO_2$ (DCM:MeOH=50:1 to 20:1) to give the title compound (49% for 3 steps) as a yellow solid. $^1$H NMR (400 MHz, DMSO-$d_6$): δ 7.88-7.78 (2H, m), 7.65 (1H, brs), 7.37-7.21 (3H, m), 6.56-6.51 (2H, m), 5.89-5.82 (2H, m), 4.91 (4H, brs), 4.59 (2H, brs), 4.54 (4H, brs), 3.86 (3H, s), 3.82 (2H, brs), 3.58 (3H, s), 2.10-2.08 (8H, m), 1.99 (2H, brs), 1.49-1.46 (2H, m), 1.34 (9H, s), 1.28-1.25 (7H, m), 0.92-0.86 (2H, m). LC-MS: m/z=973.3 $[M+H]^+$.

Step F: (E)-1-(4-(7-((4-(1-(tert-butoxycarbonyl)piperidin-4-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(7-((4-(1-(tert-butoxycarbonyl)piperidin-4-yl)but-2-yn-1-yl)oxy)-5-carbamoyl-2-(1-ethyl-3-methyl-1H-pyrazole-5-carboxamido)-1H-benzo[d]-imidazol-1-yl)but-2-en-1-yl)-2-(1-ethyl-3-methyl-1H-pyrazole-5-carboxamido)-7-methoxy-1H-benzo [d]imidazole-5-carboxylate. The crude product was used for the next reaction without purification. LC-MS: m/z=959.5 $[M+H]^+$.

Step G: tert-butyl (E)-4-(4-((5-carbamoyl-1-(4-(5-carbamoyl-2-(1-ethyl-3-methyl-1H-pyrazole-5-carboxamido)-7-methoxy-1H-benzo[d]imidazol-1-yl) but-2-en-1-yl)-2-(1-ethyl-3-methyl-1H-pyrazole-5-carboxamido)-1H-benzo[d]imidazol-7-yl)oxy)but-2-yn-1-yl)piperidine-1-carboxylate The title compound was prepared in a similar fashion to Example 3 with (E)-1-(4-(7-((4-(1-(tert-butoxycarbonyl)piperidin-4-yl)but-2-yn-1-yl)oxy)-5-carbamoyl-2-(1-ethyl-3-methyl-1H-pyrazole-5-carboxamido)-1H-benzo[d]-imidazol-1-yl)but-2-en-1-yl)-2-(1-ethyl-3-methyl- 1H-pyrazole-5-carboxamido)-7-methoxy-1H-benzo[d]imidazole-5-carboxylic acid. The crude product was purified by crystallization from Hexanes/acetone to give the title compound (54% for 2 steps) as a pale yellow solid. $^1$H NMR (400 MHz, DMSO-$d_6$): δ 7.96-7.90 (2H, m), 7.64 (2H, brs), 7.36-7.28 (4H, m), 6.54-6.52 (2H, m), 5.94-5.83 (2H, m), 4.91 (4H, brs), 4.67 (2H, brs), 4.54 (4H, brs), 3.82 (2H, brs), 3.68 (3H, s), 2.10-2.08 (7H, m), 1.99 (2H, brs), 1.49-1.46 (2H, m), 1.33 (9H, s), 1.28-1.25 (8H, m), 0.92-0.86 (2H, m). LC-MS: m/z=958.5 $[M+H]^+$.

Example 43: (E)-1-(4-(5-carbamoyl-2-(1-ethyl-3-methyl-1H-pyrazole-5-carboxamido)-7-((4-(piperidin-4-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride

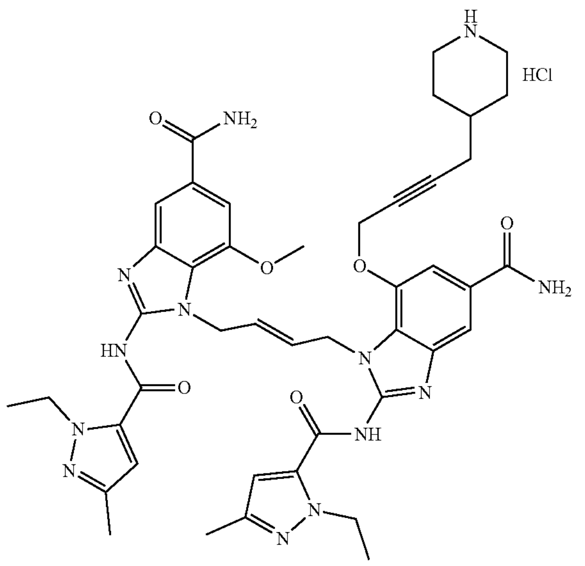 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCC3CCNCC3)c21 ; Cl]

To a solution of tert-butyl (E)-4-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidine-1-carboxylate (Example 42, 220 mg, 0.230 mmol) in DCM (10 mL) was added HCl (4 M in dioxane 0.800 mL, 3.20 mmol) at 0° C. The reaction mixture was stirred at room temperature for 1 hour. After concentration in vacuo, the residue was purified by crystallization from $Et_2O$/MeOH to give the title compound (190 mg, 93%) as a pale yellow solid. $^1H$ NMR (400 MHz, DMSO-$d_6$): δ 8.78-8.76 (1H, m), 8.39-8.37 (1H, m), 8.01-7.99 (2H, m), 7.65 (1H, d, J=0.8 Hz), 7.64 (1H, d, J=0.8 Hz), 7.41-7.38 (3H, m), 7.30 (1H, s), 6.55 (1H, s), 6.53 (1H, s), 5.92-5.81 (2H, m), 4.91-4.90 (4H, m), 4.71 (2H, s), 4.54-4.51 (4H, m), 3.69 (3H, s), 3.18-3.15 (2H, m), 2.70-2.67 (2H, m), 2.10-2.09 (6H, m), 2.06-2.04 (2H, m), 1.70-1.67 (2H, m), 1.29-1.25 (8H, m). LC-MS: m/z=858.2 $[M+H]^+$.

Example 44: cyclopropyl (E)-4-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidine-1-carboxylate

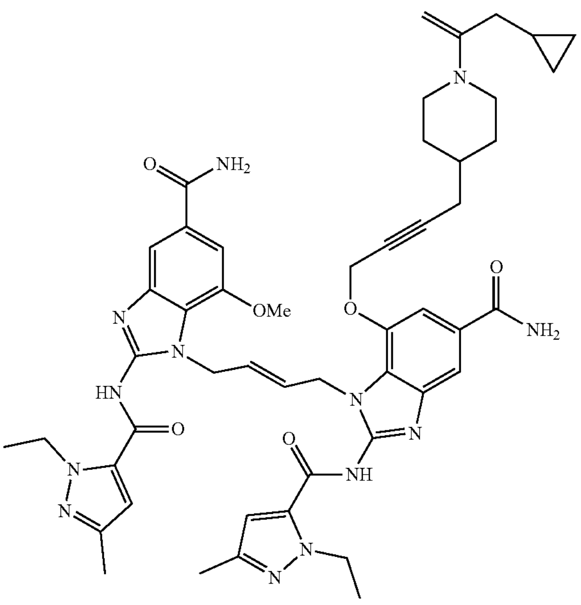 [SMILES: C=C(CC1CC1)N1CCC(CC#CCOc2cc(C(N)=O)cc3nc(NC(=O)c4cc(C)nn4CC)n(C/C=C/Cn4c(NC(=O)c5cc(C)nn5CC)nc5cc(C(N)=O)cc(OC)c54)c23)CC1]

The title compound was prepared in a similar fashion to Example 6 with (E)-1-(4-(5-carbamoyl-2-(1-ethyl-3-methyl-1H-pyrazole-5-carboxamido)-7-((4-(piperidin-4-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 43) and cyclopropyl (4-nitrophenyl) carbonate (Intermediate 7). The crude product was purified by crystallization form Hexanes/DCM followed by column chromatography on $SiO_2$ (DCM only to DCM:MeOH:$NH_4OH$=100:10:1 to 80:10:1) to give the title compound (6%) as a white solid. $^1H$ NMR (400 MHz, DMSO-$d_6$): δ 7.99 (1H, s), 7.93 (1H, s), 7.65-7.64 (2H, m), 7.39-7.38 (2H, m), 7.35 (1H, s), 7.28 (1H, s), 6.55 (1H, s), 6.51 (1H, s), 5.92-5.83 (2H, m), 4.90 (4H, s), 4.66 (2H, s), 4.58-4.50 (4H, m), 3.93-3.83 (2H, m), 3.67 (3H, s), 2.10-2.08 (7H, s), 1.97 (2H, brs), 1.47 (2H, brs), 1.32-1.22 (8H, m), 0.89 (2H, brs), 0.60-0.52 (5H, m). LC-MS: m/z=942.4 $[M+H]^+$.

Example 45: 2-hydroxyethyl (E)-4-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidine-1-carboxylate

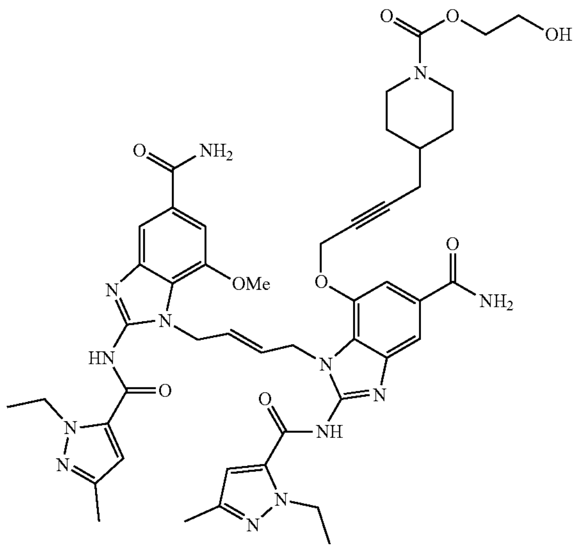 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCC3CCN(C(=O)OCCO)CC3)c21]

Step A: 2-((tert-butyldimethylsilyl)oxy)ethyl (E)-4-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidine-1-carboxylate The title compound was prepared in a similar fashion to Example 10 (Step A) with (E)-1-(4-(5-carbamoyl-2-(1-ethyl-3-methyl-1H-pyrazole-5-carboxamido)-7-((4-(piperidin-4-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 43) and 2-((tert-butyldimethylsilyl)oxy)ethyl (4-nitrophenyl) carbonate (Intermediate 10). The crude product was purified by crystallization from Hexanes/$Et_2O$ followed by column chromatography on $SiO_2$ (DCM only to DCM:MeOH:$NH_4OH$=100:10:1 to 80:10:1) to give the title compound (45%) as a white solid. $^1H$ NMR (400 MHz, DMSO-$d_6$): δ 7.97 (1H, s), 7.91 (1H, s), 7.65-7.64 (2H, m), 7.36-7.33 (2H, m), 7.27 (1H, s), 6.54 (1H, s), 6.52 (1H, s), 5.95-5.83 (2H, m), 4.90-4.89 (4H, m), 4.64 (2H, s), 4.53-4.52 (4H, m), 3.98-3.96 (2H, m), 3.87-3.84 (2H, m), 3.69-3.67 (2H, m), 3.65 (3H, s), 3.50 (1H, s), 2.10-2.08 (7H, s), 1.98 (2H, brs), 1.52-1.49 (2H, m), 1.29-1.26 (7H, m), 1.22 (2H, s), 0.79 (9H, s), −0.02 (6H, s).

Step B: 2-hydroxyethyl (E)-4-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidine-1-carboxylate The title compound was prepared in a similar fashion to Example 10 (Step B) with 2-((tert-butyldimethylsilyl)oxy)ethyl (E)-4-(4-((5-carbamoyl-1-(4-(5-carbamoyl-2-(1-ethyl-3-methyl-1H-pyrazole-5-carboxamido)-7-methoxy-1H-benzo[d]-imidazol-1-yl)but-2-en-1-yl)-2-(1-ethyl-3-methyl-1H-pyrazole-5-carboxamido)-1H-benzo-[d]imidazol-7-yl)oxy)but-2-yn-1-yl)piperidine-1-carboxylate. The crude product was purified by crystallization from $Et_2O$/MeOH to give the title compound (95%) as a white solid. $^1H$ NMR (400 MHz, DMSO-$d_6$): δ 7.98 (1H, s), 7.92 (1H, s), 7.66-7.65 (2H, m), 7.38-7.36 (2H, m), 7.28 (1H, s), 6.56 (1H, s), 6.52 (1H, s), 5.95-5.82 (2H, m), 4.91-4.90 (4H, m), 4.66 (2H, s), 4.56-4.51 (4H, m), 3.94-3.87 (4H, m), 3.67 (3H, s), 2.32 (1H, s), 2.11-2.09 (7H, s), 2.00-1.98 (2H, m), 1.52-1.48 (2H, m), 1.33-1.23 (7H, m), 0.96-0.86 (2H, m). LC-MS: m/z=946.3 $[M+H]^+$.

Example 46: tert-butyl (E)-4-(4-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidine-1-carbonyl)piperidine-1-carboxylate

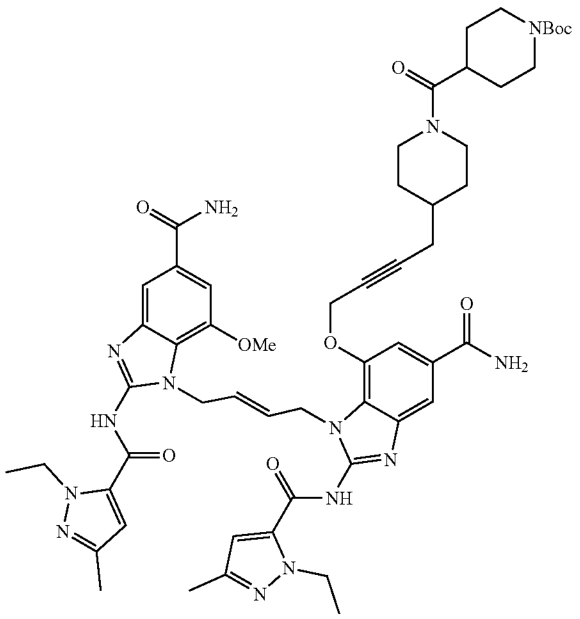 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCC3CCN(C(=O)C4CCN(C(=O)OC(C)(C)C)CC4)CC3)c21]

The title compound was prepared in a similar fashion to Example 12 with (E)-1-(4-(5-carbamoyl-2-(1-ethyl-3-methyl-1H-pyrazole-5-carboxamido)-7-((4-(piperidin-4-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 43) and 1-(tert-butoxycarbonyl)piperidine-4-carboxylic acid. The crude product was purified by column chromatography on $SiO_2$ (DCM only to DCM:MeOH:$NH_4OH$=100:10:1 to 70:10:1) to give the title compound (29%) as a pale yellow solid. $^1H$ NMR (400 MHz, DMSO-$d_6$): δ 8.00-7.93 (2H, m), 7.65-7.64 (2H, m), 7.40-7.29 (4H, m), 6.55 (1H, s), 6.52 (1H, s), 5.95-5.83 (2H, m), 4.91-4.90 (4H, m), 4.66 (2H, brs), 4.57-4.50 (4H, m), 4.27-4.24 (1H, m), 3.68 (3H, s), 2.10-2.08 (7H, m), 1.98 (2H, brs), 1.37 (9H, s), 1.30-1.22 (18H, m), 1.17 (4H, brs). LC-MS: m/z=1069.3 $[M+H]^+$.

Example 47. tert-butyl (E)-4-(4-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidine-1-carbonyl)piperazine-1-carboxylate

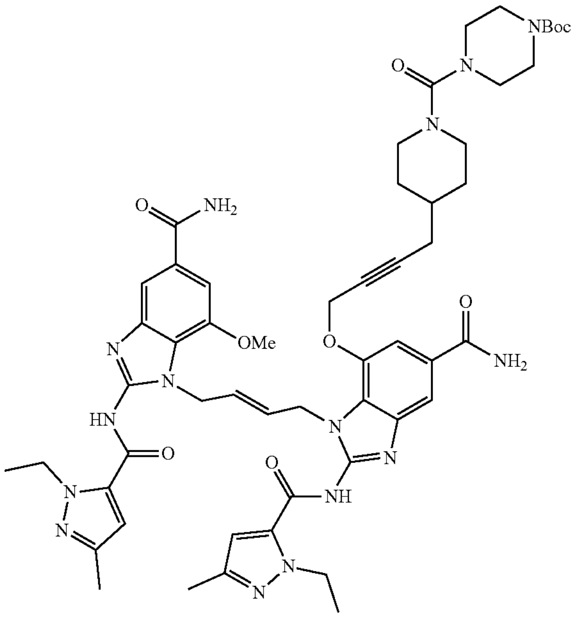 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCC3CCN(C(=O)N4CCN(C(=O)OC(C)(C)C)CC4)CC3)c21]

The title compound was prepared in a similar fashion to Example 16 with (E)-1-(4-(5-carbamoyl-2-(1-ethyl-3-methyl-1H-pyrazole-5-carboxamido)-7-((4-(piperidin-4-yl) but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 43) and 1-(tert-butyl) 4-(4-nitrophenyl) piperazine-1,4-dicarboxylate (Intermediate 6). The crude product was purified by crystallization form Hexanes/DCM followed by column chromatography on $SiO_2$ (DCM only to DCM:MeOH:$NH_4OH$=100:10:1 to 80:10:1) to give the title compound (6%) as a white solid. $^1H$ NMR (400 MHz, DMSO-$d_6$): δ 7.98-7.91 (2H, m), 7.65-7.64 (2H, m), 7.36-7.29 (4H, m), 6.54 (1H, s), 6.52 (1H, s), 5.91-5.83 (2H, m), 4.91 (4H, brs), 4.67 (2H, brs), 4.53-4.52 (4H, m), 3.68 (3H, s), 3.50-3.43 (6H, m), 3.26 (4H, brs), 2.98 (4H, brs), 2.10-2.08 (7H, m), 1.98-1.97 (2H, m), 1.48-1.45 (2H, m), 1.38 (9H, s), 1.29-1.25 (8H, m). LC-MS: m/z=1070.3 $[M+H]^+$.

Example 48: (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-((4-(1-(cyclopropylsulfonyl)piperidin-4-yl)but-2-yn-1-yl) oxy)-2-(1-ethyl-3-methyl-1H-pyrazole-5-carboxamido)-1H-benzo[d]imidazole-5-carboxamide

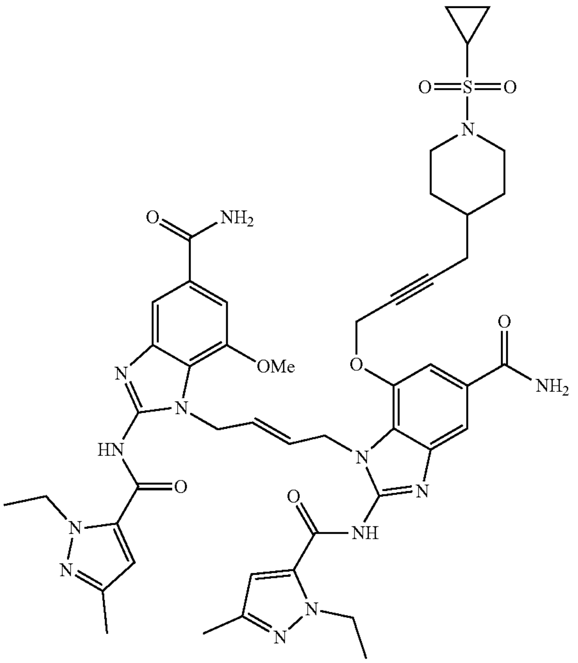 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCC3CCN(S(=O)(=O)C4CC4)CC3)c21]

The title compound was prepared in a similar fashion to Example 21 with (E)-1-(4-(5-carbamoyl-2-(1-ethyl-3-methyl-1H-pyrazole-5-carboxamido)-7-((4-(piperidin-4-yl) but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 43) and cyclopropanesulfonyl chloride. The crude product was purified by crystallization form Hexanes/DCM followed by column chromatography on $SiO_2$ (DCM:MeOH=20:1 to DCM:MeOH:$NH_4OH$=80:10:1) to give the title compound (19%) as a pale yellow solid. $^1H$ NMR (400 MHz, DMSO-$d_6$): δ 8.01-7.93 (2H, m), 7.66-7.64 (2H, m), 7.39-7.31 (4H, m), 6.56 (1H, s), 6.53 (1H, s), 5.94-5.88 (2H, m), 4.91 (4H, brs), 4.70 (2H, brs), 4.55-4.53 (4H, m), 3.71 (3H, s), 2.10-2.08 (7H, m), 1.97-1.96 (2H, m), 1.55-1.53 (2H, m), 1.30-1.26 (7H, m). LC-MS: m/z=962.2 $[M+H]^+$.

Example 49: tert-butyl (E)-4-((4-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidin-1-yl)sulfonyl)piperazine-1-carboxylate

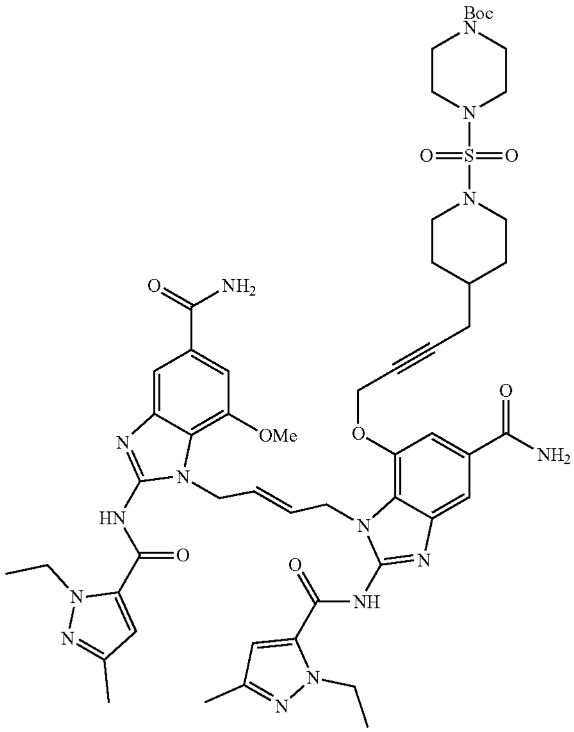 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCC3CCN(S(=O)(=O)N4CCN(C(=O)OC(C)(C)C)CC4)CC3)c21]

The title compound was prepared in a similar fashion to Example 28 with (E)-1-(4-(5-carbamoyl-2-(1-ethyl-3-methyl-1H-pyrazole-5-carboxamido)-7-((4-(piperidin-4-yl)but-2-yn-1-yl)oxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide hydrochloride (Example 43) and tert-butyl 4-(chlorosulfonyl)piperazine-1-carboxylate (Intermediate 4). The crude product was purified by crystallization form Hexanes/DCM followed by column chromatography on $SiO_2$ (DCM only to DCM:MeOH:$NH_4OH$=100:10:1 to 80:10:1) to give the title compound (44%) as a pale yellow solid. $^1H$ NMR (400 MHz, DMSO-$d_6$): δ 7.98-7.92 (2H, m), 7.65-7.64 (2H, m), 7.36-7.28 (4H, m), 6.55 (1H, s), 6.52 (1H, s), 5.89-5.86 (2H, m), 4.90 (4H, brs), 4.65 (2H, brs), 4.53-4.52 (4H, m), 3.67 (3H, s), 3.02 (4H, brs), 2.65-2.59 (2H, m), 2.11-2.09 (7H, m), 2.01-1.99 (2H, m), 1.56-1.53 (2H, m), 1.39 (9H, s), 1.29-1.25 (8H, m), 1.22 (4H, brs), 1.06-1.00 (2H, m). LC-MS: m/z=1106.2 $[M+H]^+$.

Example 50: tert-butyl (E)-3-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)azetidine-1-carboxylate

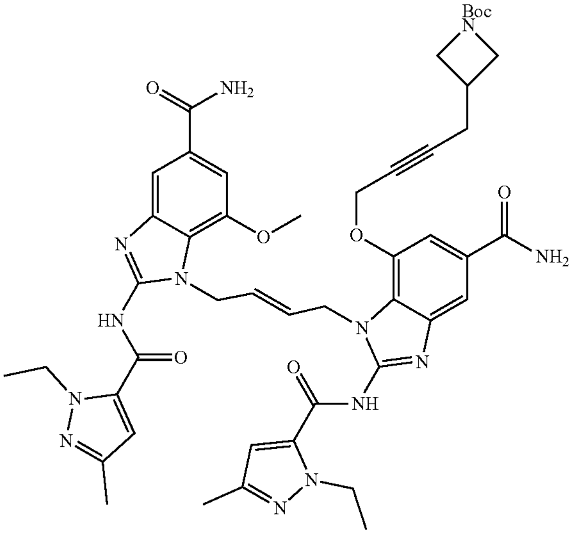 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCC3CN(C(=O)OC(C)(C)C)C3)c21]

Step A: tert-butyl (E)-3-(4-(5-carbamoyl-2-((4-((2-methoxy-4-(methoxycarbonyl)-6-nitrophenyl)amino)but-2-en-1-yl)amino)-3-nitrophenoxy)but-2-yn-1-yl)azetidine-1-carboxylate The title compound was prepared in a similar fashion to Example 1 (Step A) with tert-butyl 3-(4-(5-carbamoyl-2-chloro-3-nitrophenoxy)but-2-yn-1-yl)azetidine-1-carboxylate (Intermediate 24) and methyl (E)-4-((4-aminobut-2-en-1-yl)amino)-3-methoxy-5-nitrobenzoate (Intermediate 1).

The crude product was purified by column chromatography on $SiO_2$ (DCM:MeOH:$NH_4OH$=200:10:1) to afford the title compound (49%) as a reddish foam. $^1H$ NMR (400 MHz, DMSO-$d_6$): δ 8.15 (1H, d, J=1.6 Hz), 8.06 (1H, d, J=1.6 Hz), 7.93 (1H, t, J=6.4 Hz), 7.73 (1H, t, J=6.0 Hz), 7.53 (1H, d, J=1.6 Hz), 7.31 (1H, d, J=1.6 Hz), 5.56-5.47 (2H, m), 4.72 (2H, s), 4.06-4.06 (4H, m), 3.79 (5H, s), 3.77 (3H, s), 1.30 (9H, s). LC-MS: m/z=683.2 $[M+H]^+$.

Step B: tert-butyl (E)-3-(4-(3-amino-2-((4-((2-amino-6-methoxy-4-(methoxycarbonyl)phenyl)amino)but-2-en-1-yl)amino)-5-carbamoylphenoxy)but-2-yn-1 -yl)azetidine-1-carboxylate The title compound was prepared in a similar fashion to Example 1 (Step B) with tert-butyl (E)-3-(4-(5-carbamoyl-2-((4-((2-methoxy-4-(methoxycarbonyl)-6-nitrophenyl)amino)but-2-en-1-yl)amino)-3-nitrophenoxy)but-2-yn-1-yl)azetidine-1-carboxylate. The crude product was used for the next reaction without purification as a light brown foam. LC-MS: m/z=623.2 $[M+H]^+$.

Step C: methyl (E)-1-(4-(7-((3-(1-(tert-butoxycarbonyl)piperidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 35 (Step E) with tert-butyl (E)-3-(4-(3-amino-2-((4-((2-amino-6-methoxy-4-(methoxycarbonyl)phenyl)amino)but-2-en-1-yl)amino)-5-carbamoylphenoxy)but-2-yn-1-yl)azetidine-1-carboxylate and 1-ethyl-3-methyl-1H-pyrazole-5-carbonyl isothiocyanate in dioxane (Intermediate 3). The crude solid product was suspended in EtOAc and a solid was filtered off. The filtrate was solidified from $Et_2O$/Hexanes, collected by filtration, washed with hexanes, and dried under vacuum to afford the title compound (18%, for 2 steps) as a light brown solid. $^1H$ NMR (400 MHz, DMSO-$d_6$): δ 12.90 (1H, s), 12.84 (1H, s), 7.86 (1H, s), 7.77 (1H, d, J=1.6 Hz), 7.67 (1H, d, J=0.8 Hz), 7.35 (1H, s), 7.28 (1H, s), 7.19 (1H, d, J=1.2 Hz), 6.56 (1H, s), 6.50 (1H, s), 5.87-5.84 (2H, m), 4.91 (4H, t, J=6.4 Hz), 4.57-4.53 (6H, m), 3.87 (3H, s), 3.75-3.71 (2H, m), 3.59 (3H, s), 3.40-3.35 (2H, m), 2.33-2.31 (2H, m), 2.12 (6H, d, J=2.4 Hz), 1.31 (9H, s), 1.30-1.27 (6H, m). LC-MS: m/z=945.3 $[M+H]^+$.

Step D: (E)-1-(4-(7-((4-(1-(tert-butoxycarbonyl)azetidin-3-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(7-((4-(1-(tert-butoxycarbonyl)azetidin-3-yl)but-2-yn-1-yl)oxy)-5-carbamoyl-2 -(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate. The crude solid product was suspended in acetone/Hexanes, collected by filtration, washed with hexanes and dried under vacuum to afford the title compound (87%) as a white solid. $^1H$ NMR (400 MHz, DMSO-$d_6$): δ 12.84 (2H, s), 7.92 (1H, s), 7.74 (1H, d, J=1.2 Hz), 7.67 (1H, s), 7.32 (2H, s), 7.26 (1H, d, J=0.8 Hz), 6.52 (2H, d, J=6.8 Hz), 5.87-5.85 (2H, m), 4.91 (4H, s), 4.62 (2H, s), 4.53 (4H, q, J=6.8 Hz), 3.73 (2H, t, J=8.6 Hz), 3.63 (3H, s), 2.33 (2H, d, J=6.9 Hz), 2.11 (6H, s), 1.31 (9H, s), 1.28 (6H, t, J=7.2 Hz). LC-MS: m/z=931.3 $[M+H]^+$.

Step E: tert-butyl (E)-3-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)azetidine-1-carboxylate The title compound was prepared in a similar fashion to Example 3 with (E)-1-(4-(7-((4-(1-(tert-butoxycarbonyl)azetidin-3-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid. The crude solid compound was suspended in water and collected by filtration. The crude solid was purified by recrystallization from acetone/$Et_2O$, collected by filtration, and dried under vacuum to afford the title compound (62%) as a white solid. $^1H$ NMR (400 MHz, DMSO-$d_6$): □□ 12.79 (2H, s), 7.92 (1H, s), 7.86 (1H, s), 7.62 (2H, d, J=5.2 Hz), 7.30 (3H, s), 7.24 (1H, s), 6.49 (2H, d, J=4.0 Hz), 5.85-5.82 (2H, m), 4.87 (4H, s), 4.62 (2H, s), 4.49 (4H, d, J=6.8 Hz), 3.70 (2H, t, J=8.2 Hz), 3.63 (3H, s), 3.37-3.35 (2H, m), 2.29-2.28 (2H, m), 2.06 (6H, d, J=3.2 Hz), 1.27 (9H, s), 1.24 (6H, t, J=7.3 Hz). LC-MS: m/z=930.3 $[M+H]^+$.

Example 51: tert-butyl (E)-3-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)pyrrolidine-1-carboxylate

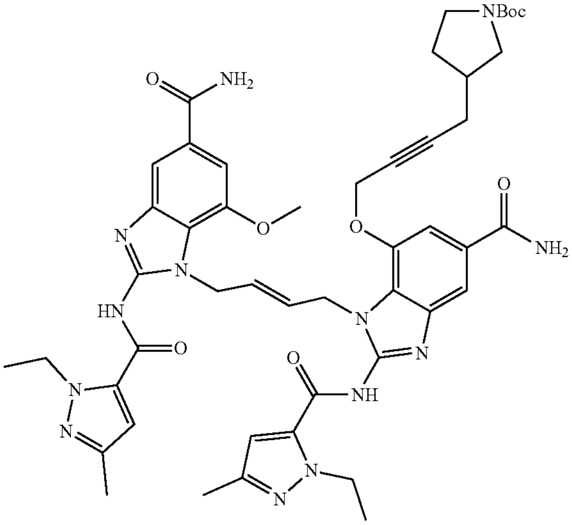 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCC3CCN(C(=O)OC(C)(C)C)C3)c21]

Step A: tert-butyl (E)-3-(4-(5-carbamoyl-2-((4-((2-methoxy-4-(methoxycarbonyl)-6-nitrophenyl)amino)but-2-en-1-yl)amino)-3-nitrophenoxy)but-2-yn-1-yl)pyrrolidine-1-carboxylate The title compound was prepared in a similar fashion to Example 1 (Step A) with tert-butyl 3-(4-(5-carbamoyl-2-chloro-3-nitrophenoxy)but-2-yn-1-yl)pyrrolidine-1-carboxylate (Intermediate 25) and methyl (E)-4-((4-aminobut-2-en-1-yl)amino)-3-methoxy-5-nitrobenzoate hydrochloride (Intermediate 1). The crude product was purified by column chromatography on NH—$SiO_2$ (DCM only to DCM: MeOH=98:2) to afford the title compound (83%) as an orange solid. LC-MS: m/z=697.2 $[M+H]^+$.

Step B: tert-butyl (E)-3-(4-(3-amino-2-((4-((2-amino-6-methoxy-4-(methoxycarbonyl)phenyl)amino)but-2-en-1-yl)amino)-5-carbamoylphenoxy)but-2-yn-1-yl)pyrrolidine-1-carboxylate The title compound was prepared in a similar fashion to Example 1 (Step B) with tert-butyl (E)-3-(4-(5-carbamoyl-2-((4-((2-methoxy-4-(methoxycarbonyl)-6-nitrophenyl)amino)but-2-en-1-yl)amino)-3-nitrophenoxy)but-2-yn-1-yl)pyrrolidine-1-carboxylate. The crude product was used for the next reaction without purification as a light brown solid. LC-MS: m/z=637.2 $[M+H]^+$.

Step C: methyl 2-((amino-13-bromanylidene) amino)-1-((2E)-4-(2-((amino-13-bromanylidene) amino)-7-((4-(1-(tert-butoxycarbonyl)pyrrolidin-3-yl)but-2-yn-1-yl)oxy)-5-carbamoyl-1H-benzo[d] imidazol-1-yl)but-2-en-1-yl)-7-methoxy-1H-benzo [d]imidazole-5-carboxylate The title compound was prepared in a similar fashion to Example 1 (Step C) with tert-butyl (E)-3-(4-(3-amino-2-((4-((2-amino-6-methoxy-4-(methoxycarbonyl)phenyl)amino) but-2-en-1-yl)amino)-5-carbamoylphenoxy)but-2-yn-1-yl) pyrrolidine-1-carboxylate. The crude solid product was recrystallized from $Et_2O$/MeOH, collected by filtration, washed with $Et_2O$ and dried under vacuum to afford the title compound (52%) as a yellow solid. LC-MS: m/z=687.2 $[M+H]^+$.

Step D: methyl (E)-1-(4-(7-((4-(1-(tert-butoxycarbonyl)pyrrolidin-3-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 1 (Step D) with methyl (E)-2-amino-1-(4-(2-amino-7-((4-(1-(tert-butoxycarbonyl)pyrrolidin-3-yl)but-2-yn-1-yl)oxy)-5-carbamoyl-1H-benzo[d]imidazol-1-yl)but-2-en-1-yl)-7-methoxy-1H-benzo[d]imidazole-5-carboxylate dihydrobromide and 1-ethyl-3-methyl-1H-pyrazole-5-carboxylic acid. The crude product was purified by column chromatography on $SiO_2$ (DCM:MeOH:$NH_4OH$=95:5:1) to afford the title compound (15%) as a purple solid. $^1H$ NMR (400 MHz, DMSO-$d_6$): δ 12.89 (1H, s), 12.83 (1H, s), 7.86 (1H, s), 7.76 (1H, s), 7.67 (1H, s), 7.35 (1H, s), 7.28 (1H, d, J=12.0 Hz), 7.17 (1H, d, J=16.8 Hz), 6.55 (1H, s), 6.51 (1H, s), 5.93-5.79 (2H, m), 4.91 (4H, d, J=4.0 Hz), 4.57-4.50 (6H, m), 3.86 (3H, s), 3.59 and 3.52 (3H, s+s), 3.29-3.24 (1H, m), 3.20-3.13 (1H, m), 3.06-2.98 (1H, m), 2.76-2.73 (1H, m), 2.14 (2H, s), 2.10 (7H, s), 1.74-1.73 (1H, m), 1.35 (10H, d, J=2.8 Hz), 1.29 (6H, td, J=7.1, 2.5 Hz).

Step E: (E)-1-(4-(7-((4-(1-(tert-butoxycarbonyl) pyrrolidin-3-yl)but-2-yn-1-yl)oxy)- 5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(7-((4-(1-(tert-butoxycarbonyl)pyrrolidin-3-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo [d]imidazole-5-carboxylate. The crude solid product was washed with water and dried under vacuum to afford the title compound (69%) as a purple solid. $^1H$ NMR (400 MHz, DMSO-$d_6$): δ 12.83 (2H, d, J=10.8 Hz), 7.87 (1H, s), 7.72 (1H, s), 7.62 (1H, s), 7.32-7.29 (2H, m), 7.22 (1H, d, J=12.0 Hz), 6.50 (1H, s), 6.47 (1H, s), 5.88-5.78 (2H, m), 4.88 (4H, s), 4.62-4.56 (2H, m), 4.50 (4H, d, J=6.8 Hz), 3.62-3.56 (3H, s+s), 3.03-2.93 (1H, m), 2.71 (1H, t, J=8.8 Hz), 2.11 (2H, s), 2.06 (7H, s), 1.70 (1H, brs), 1.30 (10H, s), 1.24 (6H, t, J=7.0 Hz).

Step F: tert-butyl (E)-3-(4-((5-carbamoyl-1-(4-(5-carbamoyl-2-(1-ethyl-3-methyl-1H-pyrazole-5-carboxamido)-7-methoxy-1H-benzo[d]imidazol-1-yl) but-2-en-1-yl)-2-(1-ethyl-3-methyl-1H-pyrazole-5-carboxamido)-1H-benzo[d]imidazol-7-yl)oxy)but-2-yn-1-yl)pyrrolidine-1-carboxylate The title compound was prepared in a similar fashion to Example 3 with (E)-1-(4-(7-((4-(1-(tert-butoxycarbonyl) pyrrolidin-3-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid. The crude product was purified by column chromatography on NH—$SiO_2$ (DCM:MeOH=93:7) to afford the title compound (31%) as a reddish brown solid. $^1H$ NMR (400 MHz, DMSO-$d_6$): δ 12.83 (2H, s), 7.93 (1H, s), 7.87 (1H, s), 7.67 (1H, s), 7.65 (1H, s), 7.30-7.24 (4H, m), 6.51 (2H, s), 5.93-5.79 (2H, m), 4.90 (4H, s), 4.64 (2H, d, J=22.0 Hz), 4.56-4.53 (4H, m), 3.67-3.62 (3H, s+s), 3.25-3.17 (1H, m), 3.05 (1H, t, J=8.0 Hz), 2.77 (1H, t, J=8.8 Hz), 2.16 (2H, s), 2.10 (7H, s), 1.75 (1H, brs), 1.34 (10H, s), 1.27 (6H, t, J=6.4 Hz). LC-MS: m/z=944.3 $[M+H]^+$.

Example 52: tert-butyl (E)-3-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidine-1-carboxylate

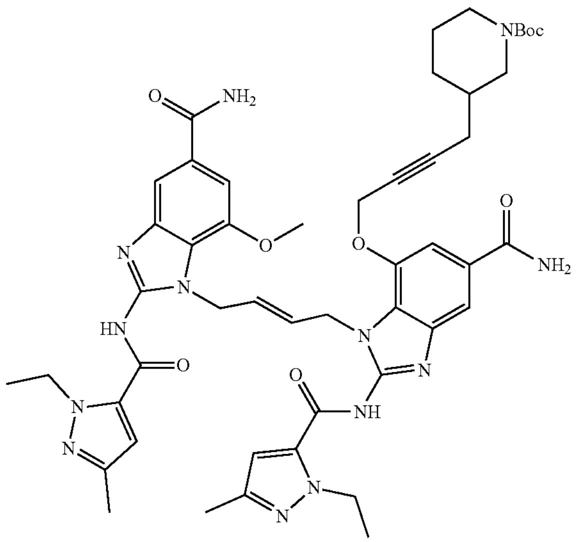 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCC#CCC3CCCN(C(=O)OC(C)(C)C)C3)c21]

Step A: tert-butyl (E)-3-(4-(5-carbamoyl-2-((4-((2-methoxy-4-(methoxycarbonyl)-6-nitrophenyl)amino) but-2-en-1-yl)amino)-3-nitrophenoxy)but-2-yn-1-yl) piperidine-1-carboxylate The title compound was prepared in a similar fashion to Example 1 (Step A) with tert-butyl 3-(4-(5-carbamoyl-2-chloro-3-nitrophenoxy)but-2-yn-1-yl)piperidine-1-carboxylate (Intermediate 26) and methyl (E)-4-((4-aminobut-2-en-1-yl)amino)-3-methoxy-5-nitrobenzoate (Intermediate 1). The crude product was purified by column chromatography on $SiO_2$ (DCM only to DCM:MeOH:$NH_4OH$=200:10:1) to afford the title compound (41%) as a reddish foam. $^1$H NMR (400 MHz, DMSO-$d_6$): δ 8.15 (1H, d, J=2.0 Hz), 8.07 (1H, d, J=2.0 Hz), 7.94 (1H, t, J=6.2 Hz), 7.72 (1H, t, J=5.6 Hz), 7.56 (1H, d, J=1.6 Hz), 7.32 (1H, d, J=1.6 Hz), 5.56-5.55 (2H, m), 4.75 (2H, s), 4.06 (4H, s), 3.79 (3H, s), 3.77 (3H, s), 3.67 (1H, d, J=12.8 Hz), 2.63-2.57 (1H, m), 2.12 (2H, t, J=5.6 Hz), 1.66-1.64 (1H, m), 1.48-1.44 (2H, m), 1.32 (9H, s), 1.19 (1H, s). LC-MS: m/z=711.2 $[M+H]^+$.

Step B: tert-butyl (E)-3-(4-(3-amino-2-((4-((2-amino-6-methoxy-4-(methoxycarbonyl)phenyl)amino)but-2-en-1-yl)amino)-5-carbamoylphenoxy)but-2-yn-1-yl)piperidine-1-carboxylate The title compound was prepared in a similar fashion to Example 1 (Step B) with tert-butyl (E)-3-(4-(5-carbamoyl-2-((4-((2-methoxy-4-(methoxycarbonyl)-6-nitrophenyl)amino)but-2-en-1-yl)amino)-3-nitrophenoxy)but-2-yn-1-yl)piperidine-1-carboxylate. The crude product was used for the next reaction without purification as a light brown foam. LC-MS: m/z=651.2 $[M+H]^+$.

Step C: methyl (E)-1-(4-(7-((3-(1-(tert-butoxycarbonyl)piperidin-3-yl)prop-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate The title compound was prepared in a similar fashion to Example 35 (Step E) with tert-butyl (E)-3-(4-(3-amino-2-((4-((2-amino-6-methoxy-4-(methoxycarbonyl)phenyl)amino)but-2-en-1-yl)amino)-5-carbamoylphenoxy)but-2-yn-1-yl)piperidine-1-carboxylate and 1-ethyl-3-methyl-1H-pyrazole-5-carbonyl isothiocyanate (Intermediate 3). The crude product was purified by column chromatography on $SiO_2$ (DCM:MeOH:$NH_4OH$=200:10:1) to afford the title compound (54% for 2 steps) as a light brown solid. $^1$H NMR (400 MHz, DMSO-$d_6$): δ 12.86 (1H, s), 12.80 (1H, s), 7.84 (1H, s), 7.74 (1H, s), 7.63 (1H, s), 7.32 (1H, s), 7.27 (1H, s), 7.18 (1H, s), 6.52 (1H, s), 6.46 (1H, s), 5.82-5.81 (2H, m), 4.89 (4H, d, J=14.8 Hz), 4.56-4.49 (6H, m), 3.83 (3H, s), 3.65-3.62 (1H, m), 3.55 (3H, s), 2.07 (6H, s), 1.97-1.93 (2H, m), 1.45-1.60 (1H, m), 1.37 (2H, s), 1.29 (9H, s), 1.24 (6H, t, J=6.6 Hz), 1.19 (1H, s). LC-MS: m/z=973.4 $[M+H]^+$.

Step D: (E)-1-(4-(7-((4-(1-(tert-butoxycarbonyl)piperidin-3-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid The title compound was prepared in a similar fashion to Example 1 (Step E) with methyl (E)-1-(4-(7-((4-(1-(tert-butoxycarbonyl)piperidin-3-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylate. The crude solid product was suspended in acetone/Hexanes, collected by filtration, washed with hexanes, and dried under vacuum to afford the title compound (93%) as a white solid. $^1$H NMR (400 MHz, DMSO-$d_6$): δ 12.83 (2H, s), 7.94 (1H, s), 7.74 (1H, d, J=1.2 Hz), 7.67 (1H, s), 7.33 (2H, s), 7.27 (1H, d, J=0.8 Hz), 6.53 (2H, d, J=5.2 Hz), 5.87-5.82 (2H, m), 4.92 (4H, d, J=16.0 Hz), 4.63 (2H, s), 4.54 (4H, q, J=6.8 Hz), 3.67 (1H, d, J=14.6 Hz), 3.62 (3H, s), 2.12 (6H, d, J=2.8 Hz), 1.99-1.97 (2H, m), 1.57-1.57 (1H, m), 1.41 (1H, d, J=12.8 Hz), 1.32 (10H, s), 1.28 (7H, td, J=7.1, 1.3 Hz). LC-MS: m/z=959.3 $[M+H]^+$.

Step E: tert-butyl (E)-3-(4-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)but-2-yn-1-yl)piperidine-1-carboxylate The title compound was prepared in a similar fashion to Example 3 with (E)-1-(4-(7-((4-(1-(tert-butoxycarbonyl)piperidin-3-yl)but-2-yn-1-yl)oxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxylic acid. The crude solid product was suspended in water and collected by filtration. The solid was purified by recrystallization from acetone/$Et_2O$, collected by filtration and dried under vacuum to afford the title compound (70%) as a light brown solid. $^1$H NMR (400 MHz, DMSO-$d_6$): □□ 12.84 (2H, s), 7.96 (1H, s), 7.90 (1H, s), 7.67-7.65 (2H, m), 7.36 (3H, s), 7.29 (1H, s), 6.53 (2H, d, J=3.6 Hz), 5.89-5.86 (2H, m), 4.93 (4H, d, J=19.2 Hz), 4.67 (2H, s), 4.54 (4H, q, J=7.0 Hz), 3.67 (4H, s), 2.10 (6H, d, J=4.8 Hz), 1.99-1.97 (2H, m), 1.57 (1H, s), 1.42-1.40 (1H, m), 1.32 (9H, s), 1.28 (7H, t, J=7.2 Hz), 1.23 (1H, s). LC-MS: m/z=958.3 $[M+H]^+$.

Biological Activity

| Example No | ISG reporter activity in THP1-Dual cell |
|---|---|
| 1 | C |
| 2 | C |
| 3 | A |
| 4 | B |
| 5 | A |
| 6 | A |
| 7 | A |
| 8 | A |
| 9 | B |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | C |
| 34 | A |
| 35 | A |
| 36 | B |
| 37 | A |
| 38 | C |
| 39 | C |

-continued

| Example No | ISG reporter activity in THP1-Dual cell |
|---|---|
| 40 | B |
| 41 | A |
| 42 | A |
| 43 | B |
| 44 | A |
| 45 | A |
| 46 | A |
| 47 | A |
| 48 | A |
| 49 | A |
| 50 | A |
| 51 | A |
| 52 | A |

A: below 50 nM,
B: 50~500 nM,
C: above 500 nM

Cell Lines and Reagents

THP1-Blue cells (cat. no. thp-isg) were purchased from InvivoGen (Sandiago, USA). Penicillin—streptomycin (cat. no. L0022-100), Fetal Bovine Serum (FBS) (cat. no. S1480-500) and Roswell Park Memorial Institute (RPMI) 1640 media (cat. L0498-500) were purchased from biowest (Nuaille, France). Zeocin (cat. no. ant-zn-OS) and Normocin (cat. no. ant-nr-1) were purchased from InvivoGen (Sandiago, USA). QUANTI-Blue™ (cat. no. rep-qbs) was purchased from InvivoGen. THP1-Blue cells were cultured in RPMI 1640 medium with 10% heat-inactivated FBS, 100 µg/ml Normocin, 100 µg/ml Zeocin and 100 U/ml-100 µg/ml penicillin-streptomycin. The cells were incubated at 37° C. in a humidified atmosphere of 5% $CO_2$.

ISG Reporter Assay

THP1-Blue cells were seeded at $5\times10^4$ cells/well (90 µl/well). 10 µl of compounds were added to the cells and incubated for 24 hours. 20 µl of cell culture supernatant was dispensed new 96-well plate (cat. no. 30096) with 180 µl of QUANTI-Blue™ solution and incubated for 15 minutes at 37° C. The absorbance was measured by Varioskan Lux (Thermofisher Scientific, USA) at 655 nm.

What is claimed is:

1. A compound of the formulas I:

I

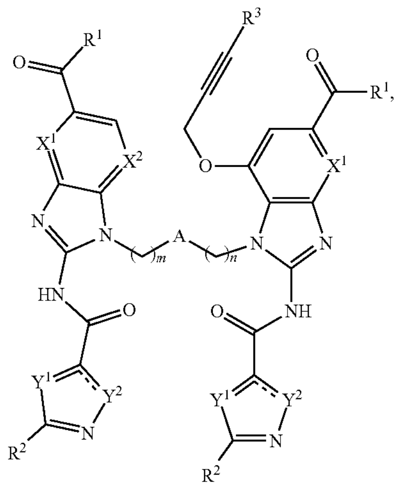

wherein, each $R^1$ is independently $NH_2$, OH, $NHOR^4$ or $NHR^4$;

each $R^2$ is independently hydrogen, halogen, $CF_3$, —$(C_1$-$C_6)$alkyl, —$O(C_1$-$C_6)$alkyl, acyl, amino, substituted amino, cyano, acyloxy or aryloxy;

$R^3$ is hydrogen, halogen, $CF_3$, acyl, amino, substituted amino, —$(C_1$-$C_6)$alkyl, —$(C_1$-$C_6)$haloalkyl, —$(C_3$-$C_6)$cycloalkyl, —$(C_1$-$C_6)$alkoxy, —$(C_1$-$C_6)$hydroxyalkyl, $hetCyc^1$, $hetCyc^2$, —$(C_1$-$C_3)$alkyl[$hetCyc^1$], —$(C_1$-$C_3)$alkyl[$hetCyc^2$], —$(C_1$-$C_3)$alkyl[$hetAr^2$], —$(C_1$-$C_3)$alkyl[$hetAr^3$], cyano, nitro, alkoxy, acyloxy or aryloxy;

$R^4$ is H, trifluoromethyl, —$(C_1$-$C_6)$alkyl, —$(C_2$-$C_6)$alkenyl, —$(C_2$-$C_6)$alkynyl, —$(C_1$-$C_3)$alkyl[$(C_3$-$C_6)$cycloalkyl], —$(C_1$-$C_6)$fluoroalkyl, —$(C_1$-$C_6)$difluoroalkyl, —$(C_1$-$C_6)$trifluoroalkyl, —$(C_1$-$C_6)$alkylamine, —$(C_1$-$C_6)$hydroxyalkyl, —$(C_2$-$C_6)$dihydroxyalkyl, [$(C_1$-$C_6)$alkoxy]$(C_1$-$C_6)$alkyl- or [$(C_1$-$C_6)$alkoxy]-[$(C_1$-$C_6)$alkoxy]-$(C_1$-$C_6)$alkyl-;

each $X^1$ and $X^2$ are independently N or $CR^5$;

$R^5$ is hydrogen, halogen, OH, $CF_3$, acyl, amino, substituted amino, —$(C_1$-$C_6)$alkyl, substituted $(C_1$-$C_6)$alkyl, —$(C_1$-$C_6)$haloalkyl, cyano, nitro, alkoxy, acyloxy, aryloxy, —$O(C_1$-$C_6)$alkyl, —$O(C_1$-$C_6)$hydroxyalkyl, —$O(C_2$-$C_6)$alkenyl[$(C_4$-$C_6)$hydoxy], —$O(C_2$-$C_6)$alkynyl[$(C_4$-$C_6)$hydoxy], —$O(C_2$-$C_6)$alkynyl[$hetCyc^1$], —$O(C_1$-$C_6)$alkyl[$(C_1$-$C_6)$alkoxy], —$O(C_2$-$C_6)$alkenyl[$(C_1$-$C_6)$alkoxy], —$O(C_2$-$C_6)$alkynyl[$(C_1$-$C_6)$alkoxy], —$O(C_1$-$C_6)$alkyl[$(C_3$-$C_6)$cycloalkyl], —$O(C_1$-$C_3)$alkyl[$hetCyc^1$], —$O(C_1$-$C_3)$alkyl[$hetCyc^2$] or —$O(C_2$-$C_6)$alkynyl[$hetCyc^1$];

$hetCyc^1$ is a 4-6 membered heterocyclic ring containing 1-2 heteroatoms selected from nitrogen, oxygen or sulfur, wherein said heterocyclic ring is optionally substituted with a substituent selected from —$(C_1$-$C_6)$alkyl, —$(C_1$-$C_6)$alkoxy, OH, halogen, —$C(O)R^6$, —$CO_2R^6$, —$C(O)NR^6R^7$, —$S(O)_2NR^6R^7$, or —$S(O)_2R^6$;

$hetCyc^2$ is a bridged 8-membered heterocyclic ring having a ring nitrogen atom and optionally having a ring oxygen atom;

$R^6$ is H, —$(C_1$-$C_6)$alkyl, —$(C_1$-$C_6)$fluoroalkyl, —$(C_1$-$C_6)$difluoroalkyl, —$(C_1$-$C_6)$trifluoroalkyl, —$(C_1$-$C_6$ alkyl)-$NR^7R^8$, —$(C_1$-$C_6)$hydroxyalkyl, —$(C_2$-$C_6)$dihydroxyalkyl, [$(C_1$-$C_6)$alkoxy]$(C_1$-$C_6)$alkyl-, [$(C_1$-$C_6)$alkoxy]-[$(C_1$-$C_6)$alkoxy]-$(C_1$-$C_6)$alkyl-, $hetCyc^1$, $Ar^1$, $hetAr^2$ or $hetAr^3$;

$R^7$ is H or —$(C_1$-$C_6)$alkyl;

or $NR^6R^7$ forms a 4-6 membered ring with one or more heteroatoms selected from N and O, wherein said ring is optionally substituted with one or more substituents independently selected from —$(C_1$-$C_6)$alkyl, OH, $NH_2$, —$(C_1$-$C_6)$hydroxyalkyl, —$(C_1$-$C_6)$alkylamine, —$CO_2R^8$, and —$(C_1$-$C_3)$alkyl$CO_2R^8$;

$R^8$ is H, —$(C_1$-$C_3)$alkyl or —$(C_1$-$C_3)$hydroxyalkyl;

$Ar^1$ is phenyl optionally substituted with one or more substituents independently selected from $(C_1$-$C_6)$alkoxy, halogen, $(C_1$-$C_6)$alkyl and $CF_3$;

$hetAr^2$ is pyridyl optionally substituted with one or more substituents independently selected from halogen, $CF_3$, $(C_1$-$C_6)$alkyl and $(C_1$-$C_6)$alkoxy;

$hetAr^3$ is a 5-membered heteroaryl having 2-3 ring heteroatoms independently selected from N, O and S and optionally substituted with $(C_1$-$C_6)$alkyl and OH;

$Y^1$ and $Y^2$ are each independently N, O, S, $CR^9$, $NR^0$;

$R^9$ is hydrogen, halogen, $CF_3$, —$(C_1$-$C_6)$alkyl or —$O(C_1$-$C_6)$alkyl;

$R^{10}$ is hydrogen, —$(C_1$-$C_6)$alkyl or acyl;

A is —CH═CH—, —C≡C—, —$CH_2$—, —$CR^{11}R^{12}$—, —$C(O)NR^{13}$—, —$C(O)NHOR^{14}$—, —$NR^{13}C(O)$—,

—$NR^{13}CO_2$—, —$NR^{13}C(O)NR^{13}$—, —$NR^{13}$—, —($C_3$-$C_7$)cycloalkyl-, —O—, —S—, —S(O)— or —$S(O)_2$—, optionally substituted -phenyl-, optionally substituted -(5-6 membered heteroaryl)- or optionally substituted -(5-6 membered heterocycloalkyl)-;

$R^{11}$ is selected from the group consisting of F, $CF_3$, ($C_1$-$C_6$)alkyl, substituted ($C_1$-$C_6$)alkyl, cyano;

$R^{12}$ is H, F, $CF_3$, ($C_1$-$C_6$)alkyl;

or $R^{11}$ and $R^{12}$ together with the atom to which they are attached form a 3 to 7 membered carbocyclic or heterocyclic ring;

$R^{13}$ is hydrogen, ($C_1$-$C_6$)Calkyl, ($C_1$-$C_6$)Cfluoroalkyl, ($C_1$-$C_6$)difluoroalkyl or ($C_1$-$C_6$)trifluoroalkyl;

$R^{14}$ is ($C_1$-$C_6$)alkyl, ($C_1$-$C_6$)fluoroalkyl, ($C_1$-$C_6$)difluoroalkyl, ($C_1$-$C_6$)trifluoroalkyl or [($C_1$-$C_6$)alkoxy]($C_1$-$C_6$) alkyl-;

m is 0, 1, 2 or 3; and n is 0, 1, 2 or 3.

2. The compound of claim 1, wherein formula I include compounds of the Formula II-a, II-b, and II-c:

II-a

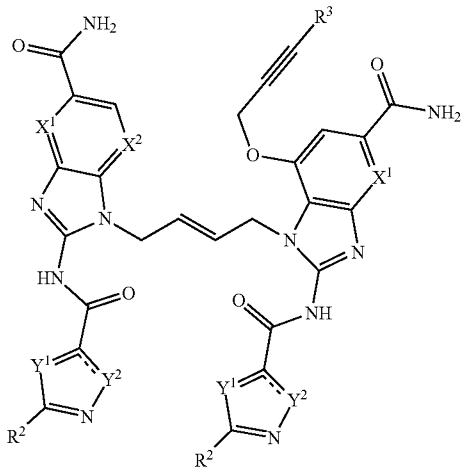

II-b

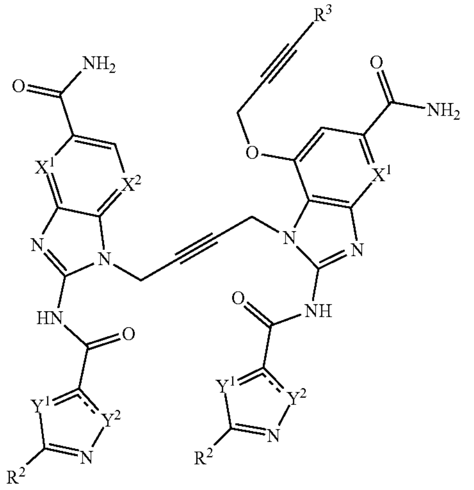

-continued

II-c

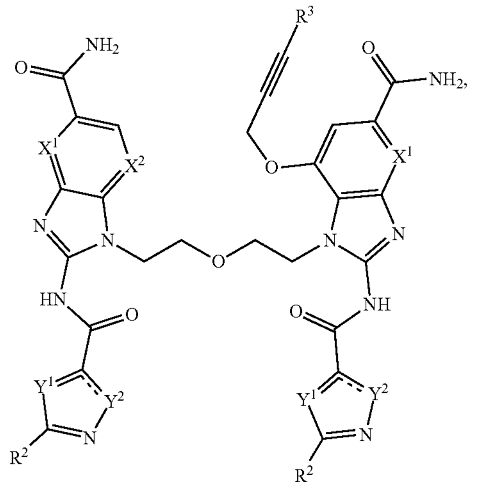

wherein each $R^2$ is independently hydrogen, halogen, $CF_3$, —($C_1$-$C_6$)alkyl, —O($C_1$-$C_6$)alkyl, acyl, amino, substituted amino, cyano, acyloxy or aryloxy;

$R^3$ is hydrogen, halogen, $CF_3$, acyl, amino, substituted amino, —($C_1$-$C_6$)alkyl, —($C_1$-$C_6$)haloalkyl, —($C_3$-$C_6$) cycloalkyl, —($C_1$-$C_6$)alkoxy, —($C_1$-$C_6$)hydroxyalkyl, $hetCyc^1$, $hetCyc^2$, —($C_1$-$C_3$)alkyl[$hetCyc^1$], —($C_1$-$C_3$) alkyl[$hetCyc^2$], —($C_1$-$C_3$)alkyl[$hetAr^2$], —($C_1$-$C_3$)alkyl[$hetAr^3$], cyano, nitro, alkoxy, acyloxy or aryloxy;

$hetCyc^1$ is a 4-6 membered heterocyclic ring containing 1-2 heteroatoms selected from nitrogen, oxygen or sulfur, wherein said heterocyclic ring is optionally substituted with a substituent selected from —($C_1$-$C_6$) alkyl, —($C_1$-$C_6$)alkoxy, OH, halogen, —$C(O)R^6$, —$CO_2R^6$, —$C(O)NR^6R^7$, —$S(O)_2NR^6R^7$, or —$S(O)_2$ $R^6$;

$hetCyc^2$ is a bridged 8-membered heterocyclic ring having a ring nitrogen atom and optionally having a ring oxygen atom;

each $X^1$ and $X^2$ are independently N or $CR^5$;

$R^5$ is hydrogen, halogen, OH, $CF_3$, acyl, amino, substituted amino, —($C_1$-$C_6$)alkyl, substituted ($C_1$-$C_6$)alkyl, —($C_1$-$C_6$)haloalkyl, cyano, nitro, alkoxy, acyloxy, aryloxy, —O($C_1$-$C_6$)alkyl, —O($C_1$-$C_6$)hydroxyalkyl, —O($C_2$-$C_6$)alkenyl[($C_4$-$C_6$)hydoxy], —O($C_2$-$C_6$)alkynyl[($C_4$-$C_6$)hydoxy], —O($C_2$-$C_6$)alkynyl[$hetCyc^1$], —O($C_1$-$C_6$)alkyl[($C_1$-$C_6$)alkoxy], —O($C_2$-$C_6$)alkenyl [($C_1$-$C_6$)alkoxy], —O($C_2$-$C_6$)alkynyl[($C_1$-$C_6$)alkoxy], —O($C_1$-$C_6$)alkyl[($C_3$-$C_6$)cycloalkyl], —O($C_1$-$C_3$)alkyl[$hetCyc^1$], —O($C_1$-$C_3$)alkyl[$hetCyc^2$] or —O($C_2$-$C_6$)alkynyl[$hetCyc^1$];

$R^6$ is H, —($C_1$-$C_6$)alkyl, —($C_1$-$C_6$)fluoroalkyl, —($C_1$-$C_6$) difluoroalkyl, —($C_1$-$C_6$)trifluoroalkyl, —($C_1$-$C_6$ alkyl)-$NR^7R^8$, —($C_1$-$C_6$)hydroxyalkyl, —($C_2$-$C_6$)dihydroxyalkyl, [($C_1$-$C_6$)alkoxy]($C_1$-$C_6$)alkyl-, [($C_1$-$C_6$) alkoxy]-[($C_1$-$C_6$)alkoxy]-($C_1$-$C_6$)alkyl-, $hetCyc^1$, $Ar^1$, $hetAr^2$ or $hetAr^3$;

$R^7$ is H or —($C_1$-$C_6$)alkyl;

or $NR^6R^7$ forms a 4-6 membered ring with one or more heteroatoms selected from N and O, wherein said ring is optionally substituted with one or more substituents independently selected from —($C_1$-$C_6$)alkyl, OH, $NH_2$, —($C_1$-$C_6$)hydroxyalkyl, —($C_1$-$C_6$)alkylamine, —$CO_2R^8$, and —($C_1$-$C_3$)alkyl$CO_2R^8$;

$R^8$ is H, —($C_1$-$C_3$)alkyl or —($C_1$-$C_3$)hydroxyalkyl;

$Ar^1$ is phenyl optionally substituted with one or more substituents independently selected from ($C_1$-$C_6$) alkoxy, halogen, ($C_1$-$C_6$)alkyl and $CF_3$;

$hetAr^2$ is pyridyl optionally substituted with one or more substituents independently selected from halogen, $CF_3$, ($C_1$-$C_6$)alkyl and ($C_1$-$C_6$)alkoxy;

$hetAr^3$ is a 5-membered heteroaryl having 2-3 ring heteroatoms independently selected from N, O and S and optionally substituted with ($C_1$-$C_6$)alkyl and OH;

$Y^1$ and $Y^2$ are each independently N, O, S, $CR^9$, $NR^{10}$;

$R^9$ is hydrogen, halogen, $CF_3$, —($C_1$-$C_6$)alkyl or —O($C_1$-$C_6$)alkyl; and $R^{10}$ is hydrogen, —($C_1$-$C_6$)alkyl or acyl.

3. The compound of claim 1, wherein formula I include compounds of the Formula III-a, III-b, III-c, and III-d:

III-a

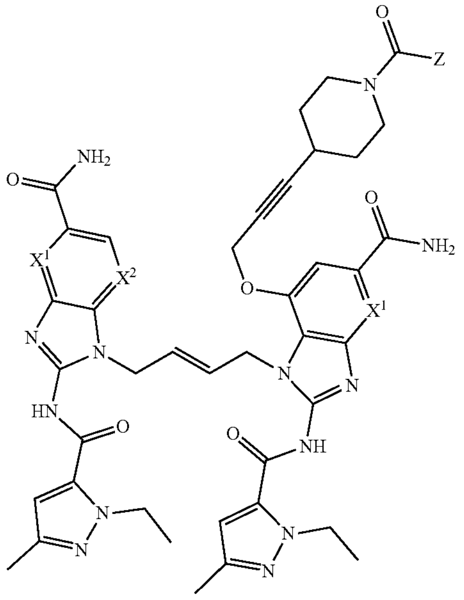

III-b

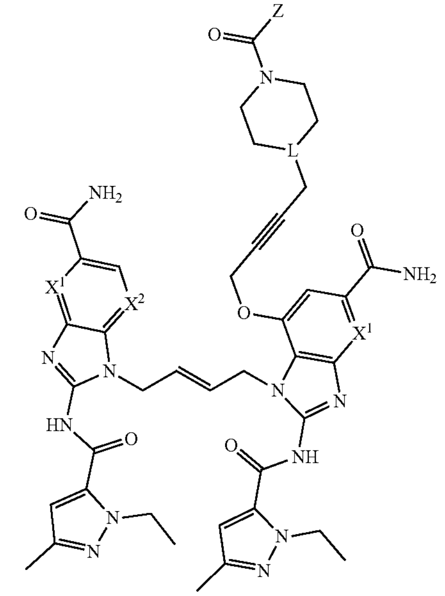

-continued

III-c

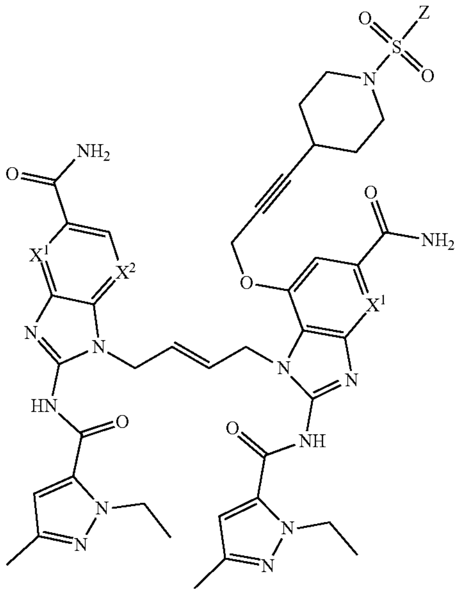

III-d

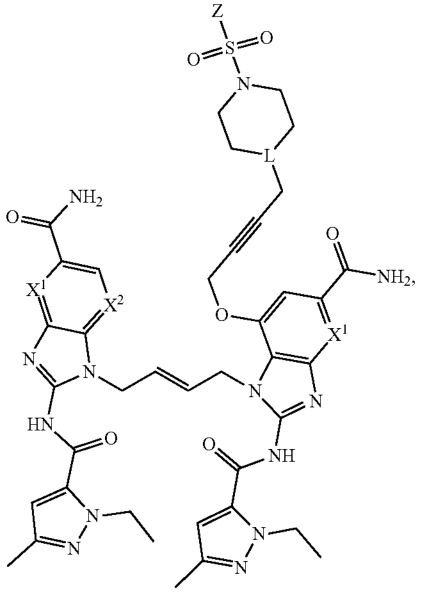

wherein Z is —$R^6$, —$OR^6$, —$NR^6R^7$, —($C_1$-$C_6$)alkyl, —($C_1$-$C_6$)fluoroalkyl, —($C_1$-$C_6$)difluoroalkyl, —($C_1$-$C_6$)trifluoroalkyl, —($C_1$-$C_6$ alkyl)-$NR^7R^8$, —($C_1$-$C_6$) hydroxyalkyl, —($C_2$-$C_6$)dihydroxyalkyl, [($C_1$-$C_6$) alkoxy]($C_1$-$C_6$)alkyl- or [($C_1$-$C_6$)alkoxy]-[($C_1$-$C_6$) alkoxy]-($C_1$-$C_6$)alkyl-;

L is CH or N;

each $X^1$ and $X^2$ are independently N or $CR^5$;

$R^5$ is hydrogen, halogen, OH, $CF_3$, acyl, amino, substituted amino, —($C_1$-$C_6$)alkyl, substituted ($C_1$-$C_6$)alkyl, —($C_1$-$C_6$)haloalkyl, cyano, nitro, alkoxy, acyloxy, aryloxy, —O($C_1$-$C_6$)alkyl, —O($C_1$-$C_6$)hydroxyalkyl, —O($C_2$-$C_6$)alkenyl[($C_4$-$C_6$)hydoxy], —O($C_2$-$C_6$)alkynyl[($C_4$-$C_6$)hydoxy], —O($C_2$-$C_6$)alkynyl[$hetCyc^1$], —O($C_1$-$C_6$)alkyl[($C_1$-$C_6$)alkoxy], —O($C_2$-$C_6$)alkenyl [($C_1$-$C_6$)alkoxy], —O($C_2$-$C_6$)alkynyl[($C_1$-$C_6$)alkoxy], —O($C_1$-$C_6$)alkyl[($C_3$-$C_6$)cycloalkyl], —O($C_1$-$C_3$)alkyl[$hetCyc^1$], —O($C_1$-$C_3$)alkyl[$hetCyc^2$] or —O($C_2$-$C_6$)alkynyl[$hetCyc^1$];

$R^6$ is H, —$(C_1\text{-}C_6)$alkyl, —$(C_1\text{-}C_6)$fluoroalkyl, —$(C_1\text{-}C_6)$difluoroalkyl, —$(C_1\text{-}C_6)$trifluoroalkyl, —$(C_1\text{-}C_6$ alkyl)-$NR^7R^8$, —$(C_1\text{-}C_6)$hydroxyalkyl, —$(C_2\text{-}C_6)$dihydroxyalkyl, $[(C_1\text{-}C_6)$alkoxy$](C_1\text{-}C_6)$alkyl-, $[(C_1\text{-}C_6)$alkoxy$]$-$[(C_1\text{-}C_6)$alkoxy$]$-$(C_1\text{-}C_6)$alkyl-, hetCyc$^1$, Ar$^1$, hetAr$^2$ or hetAr$^3$;

$R^7$ is H or —$(C_1\text{-}C_6)$alkyl;

or $NR^6R^7$ forms a 4-6 membered ring with one or more heteroatoms selected from N and O, wherein said ring is optionally substituted with one or more substituents independently selected from —$(C_1\text{-}C_6)$alkyl, OH, $NH_2$, —$(C_1\text{-}C_6)$hydroxyalkyl, —$(C_1\text{-}C_6)$alkylamine, —$CO_2R^8$, and —$(C_1\text{-}C_3)$alkyl$CO_2R^8$;

$R^8$ is H, —$(C_1\text{-}C_3)$alkyl or —$(C_1\text{-}C_3)$hydroxyalkyl;

hetCyc$^1$ is a 4-6 membered heterocyclic ring containing 1-2 heteroatoms selected from nitrogen, oxygen or sulfur, wherein said heterocyclic ring is optionally substituted with a substituent selected from —$(C_1\text{-}C_6)$alkyl, —$(C_1\text{-}C_6)$alkoxy, OH, halogen, —$C(O)R^6$, —$CO_2R^6$, —$C(O)NR^6R^7$, —$S(O)_2NR^6R^7$, or —$S(O)_2R^6$;

hetCyc$^2$ is a bridged 8-membered heterocyclic ring having a ring nitrogen atom and optionally having a ring oxygen atom;

Ar$^1$ is phenyl optionally substituted with one or more substituents independently selected from $(C_1\text{-}C_6)$alkoxy, halogen, $(C_1\text{-}C_6)$alkyl and $CF_3$;

hetAr$^2$ is pyridyl optionally substituted with one or more substituents independently selected from halogen, $CF_3$, $(C_1\text{-}C_6)$alkyl and $(C_1\text{-}C_6)$alkoxy; and hetAr$^3$ is a 5-membered heteroaryl having 2-3 ring heteroatoms independently selected from N, O and S and optionally substituted with $(C_1\text{-}C_6)$alkyl and OH.

4. A pharmaceutical composition comprising a pharmaceutically effective amount of the compound of claim 1 or a pharmaceutically acceptable salt, solvate, polymorph, ester, tautomer or prodrug thereof, and a pharmaceutically acceptable carrier.

5. A method of stimulating expression of interferon genes in a human patient, comprising administering to the patient an effective dose of the compound of claim 1 or a pharmaceutically acceptable salt thereof.

6. The method according to claim 5, wherein the administering comprises intravenous or intratumoral administration, or both.

7. The method according to claim 5, wherein the administering comprises administering the compound to the patient as an antibody-drug conjugate or in a liposomal formulation.

8. The method according to claim 5, further comprising administering an effective amount of an immune-checkpoint targeting drugs.

9. The method according to claim 8, wherein the immune-checkpoint targeting drug comprises an anti-PD1 antibody, anti-PD-L1 antibody, anti-CTLA-4 antibody or an anti-4-1BB antibody.

10. The method according to claim 5, further comprising administering an effective amount of chemotherapeutic agents.

11. The method according to claim 5, further comprising administering an effective amount of small molecule kinase targeting drugs.

12. The method according to claim 5, further comprising administering ionizing radiation or anticancer drugs.

* * * * *